(12) United States Patent
Rosenblum et al.

(10) Patent No.: US 7,238,688 B2
(45) Date of Patent: Jul. 3, 2007

(54) PIPERIDINE COMPOUNDS

(75) Inventors: Stuart B. Rosenblum, West Orange, NJ (US); Qingbei Zeng, Edison, NJ (US); Mwangi Wa Mutahi, Fords, NJ (US); Robert G. Aslanian, Rockaway, NJ (US); Pauline C. Ting, New Providence, NJ (US); Neng-Yang Shih, Warren, NJ (US); Daniel M. Solomon, Edison, NJ (US); Jianhua Cao, Edison, NJ (US); Henry A. Vaccaro, South Plainfield, NJ (US); Kevin D. McCormick, Basking Ridge, NJ (US); John J. Baldwin, Gwynedd, PA (US); Ge Li, QiXinLu (CN)

(73) Assignee: Schering Corporation, Kenilworth, NJ (US)

(*) Notice: Subject to any disclaimer, the term of this patent is extended or adjusted under 35 U.S.C. 154(b) by 135 days.

(21) Appl. No.: 10/974,329

(22) Filed: Oct. 27, 2004

(65) Prior Publication Data

US 2005/0113383 A1    May 26, 2005

Related U.S. Application Data

(62) Division of application No. 10/095,134, filed on Mar. 11, 2002, now Pat. No. 6,849,621.

(60) Provisional application No. 60/275,417, filed on Mar. 13, 2001.

(51) Int. Cl.
*A61K 31/55* (2006.01)
*C07D 243/08* (2006.01)
*C07D 241/02* (2006.01)
*C07D 401/06* (2006.01)
*C07D 403/06* (2006.01)

(52) U.S. Cl. ........... 514/217.05; 514/218; 514/252.11; 514/253.01; 514/253.1; 540/575; 540/598; 544/357; 544/360; 544/364; 544/372

(58) Field of Classification Search .......... 514/217.05, 514/218, 252.11, 253.01, 253.1; 540/575, 540/598; 544/357, 360, 364, 372
See application file for complete search history.

(56) References Cited

U.S. PATENT DOCUMENTS

| | | | |
|---|---|---|---|
| 3,401,224 A | 9/1968 | Barrett et al. | |
| 4,725,597 A | 2/1988 | Devlin et al. | |
| 5,463,074 A | 10/1995 | Shih et al. | 548/314.7 |
| 5,578,616 A | 11/1996 | Aslanian et al. | 514/341 |
| 5,633,250 A | 5/1997 | Shih | 514/218 |
| 5,807,872 A | 9/1998 | Shih | 514/326 |
| 5,869,479 A | 2/1999 | Kreutner et al. | 514/212 |
| 5,883,096 A | 3/1999 | Lowe et al. | 514/210.18 |
| 5,889,006 A | 3/1999 | Lowe et al. | 519/252.02 |
| 5,990,147 A | 11/1999 | Aslanian | 514/400 |
| 6,034,251 A | 3/2000 | Aslanian | 548/338.1 |
| 6,100,279 A | 8/2000 | Vaccaro et al. | 514/326 |
| 6,448,242 B1 | 9/2002 | Ishiwata et al. | 514/326 |
| 6,720,328 B2 | 4/2004 | Aslanian et al. | 514/275 |

FOREIGN PATENT DOCUMENTS

| | | | |
|---|---|---|---|
| AT | 261611 | * | 5/1968 |
| EP | 122488 A1 | * | 10/1984 |
| EP | 0 407 217 A1 | | 6/1990 |
| GB | 1101749 | * | 1/1968 |
| JP | 56/12359 | * | 2/1981 |
| JP | 68-12359 | | 2/1981 |
| WO | WO 95/14007 | | 5/1995 |
| WO | WO 98/05292 | | 2/1998 |
| WO | WO 98/06394 | | 2/1998 |
| WO | WO 99/24405 | | 5/1999 |
| WO | WO 99/42446 | | 8/1999 |

(Continued)

OTHER PUBLICATIONS

Hancock AA, Diehl MS, Fey TA, Bush EN, Faghih R, Miller TR, Krueger KM, Pratt JK, Cowart MD, Dickinson RW, Shapiro R, Knourek-Segel VE, Droz BA, McDowell CA, Krishna G, Brune ME, Esbenshade TA, Jacobson PB, Inflamm Res. Apr. 2005;54 Suppl 1:S27-9.*

(Continued)

*Primary Examiner*—James O. Wilson
*Assistant Examiner*—Ebenezer Sackey
(74) *Attorney, Agent, or Firm*—Henry C. Jeanette

(57) ABSTRACT

Disclosed are novel compounds of the formula $$R^1\diagdown_X\diagup N\diagdown_{(\phantom{x})_n}M^1\diagdown_Y M^2\diagdown_{(\phantom{x})_p}N\diagdown_Z R^2 \qquad (I)$$

with $(R^{12})_a$ and $(R^{13})_b$ substituents.

Also disclosed are pharmaceutical compositions comprising the compounds of Formula I.

Also disclosed are methods of treating various diseases or conditions, such as, for example, allergy, allergy-induced airway responses, and congestion (e.g., nasal congestion) using the compounds of Formula I.

Also disclosed are methods of treating various diseases or conditions, such as, for example, allergy, allergy-induced airway responses, and congestion (e.g., nasal congestion) using the compounds of Formula I in combination with a $H_1$ receptor antagonist.

26 Claims, No Drawings

FOREIGN PATENT DOCUMENTS

| WO | WO 00/00488 | 1/2000 |
|---|---|---|
| WO | WO 00/039092 | 7/2000 |
| WO | WO 02/072093 | 9/2002 |

OTHER PUBLICATIONS

Arthur A Hancock, Michael E Brune, Expert Opinion on Investigational Drugs, Mar. 2005, vol. 14, No. 3, pp. 223-241.*
Hancock AA, Bush EN, Jacobson PB, Faghih R, Esbenshade TA., Histamine H(3) antagonists in models of obesity.Inflamm Res. Mar. 2004;53 Suppl 1:S47-8.*
Philips, J.G. et al, Ann. Reports Med. Chem., vol. 31, 1998, 31-40.*
Journal of Medicinal Chemistry, 43(12), (2000), pp. 2362-2370.
Arch. Pharm. Pharm. Med. Chem 332 (1999), pp. 389-398.
Arch. Pharm. Pharm. Med. Chem 331 (1998), pp. 395-404.
Stark et al, Drugs of the Future, 21 (5) (1996) 507-520.
Philips et al, Ann. Reports Med. Chem., 31 (1998) 31-40.
Lemoucheux, et al. "Debenzylation of Tertiary Amines Using Phosgene or Triphosgene: An Efficient and Rapid Procedure for the Preparation of Carbamoyl Chlorides and Unsymmetrical Ureus. Application in Carbon-II Chemistry", J. Org. Chem. (2003) 7289-7297, vol. 68.
Lemoucheux, et al. "Debenzylation of Tertiary Amines using Phosgene or Triphosgene An Efficient and Rapid Procedure for the Preparation of Carbamayl Chlorides and Unsymmetrical Ureas: Application in Carbon-II Chemistry", J. Org. Chem. (2003) 8742, vol. 68.

* cited by examiner

PIPERIDINE COMPOUNDS

This application is a divisional of U.S. Ser. No. 10/095,134, filed Mar. 11, 2002, now U.S. 6,849,621, which claims the benefit of U.S. Provisional Application No. 60/275,417, filed Mar. 13, 2001.

BACKGROUND OF THE INVENTION

WO 95/14007 published May 26, 1995 discloses $H_3$ receptor antagonists of the imidazole type.

WO99/24405 published May 20, 1999 discloses $H_3$ receptor ligands of the imidazole type.

U.S. Pat. No. 5,869,479 issued Feb. 9, 1999 discloses compositions for the treatment of the symptoms of allergic rhinitis using a combination of at least one histamine $H_1$ receptor antagonist and at least one histamine $H_3$ receptor antagonist.

In view of the art's interest in compounds which affect $H_3$ receptors, novel compounds that are antagonists of $H_3$ receptors would be a welcome contribution to the art. This invention provides just such a contribution.

SUMMARY OF THE INVENTION

The present invention provides novel compounds of structure I.

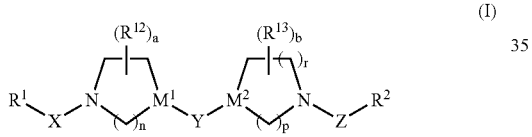

(I)

or a pharmaceutically acceptable salt or solvate thereof, wherein:

(A) $R^1$ is selected from:
(1) aryl;
(2) heteroaryl;
(3) heterocycloalkyl
(4) alkyl;
(5) —C(O)N($R^{4B}$)$_2$;
(6) cycloalkyl;
(7) arylalkyl;
(8) heteroarylheteroaryl (e.g., isoxazoylthienyl or pyridylthienyl); or
(9) a group selected from:

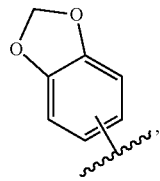

II

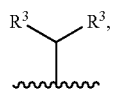

III

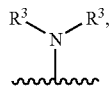

IV

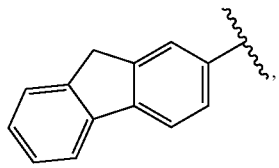

IVA

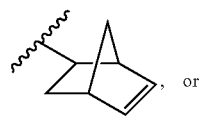

IVB

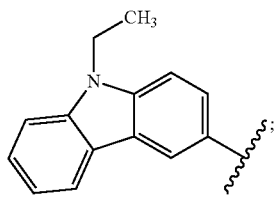

IVC

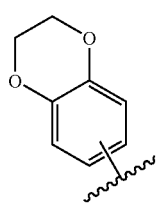, or

IVD said aryl (see (A)(1) above), heteroaryl (see (A)(2) above), aryl portion of arylalkyl (see (A)(7) above), phenyl ring of formula II (see (A)(9) above), phenyl ring of formula III (see (A)(9) above), phenyl rings of formula IVB (see (A)(9) above), or phenyl rings of formula IVD (see (A)(9) above) are optionally substituted with 1 to 3 substituents independently selected from:
(1) halogen (e.g., Br, F, or Cl, preferably F or Cl);
(2) hydroxyl (i.e., —OH);
(3) lower alkoxy (e.g., $C_1$ to $C_6$ alkoxy, preferably $C_1$ to $C_4$ alkoxy, more preferably $C_1$ to $C_2$ alkoxy, most preferably methoxy);
(4) -Oaryl (i.e., aryloxy);
(5) —$SR^{22}$;
(6) —$CF_3$;
(7) —$OCF_3$;
(8) —$OCHF_2$;

(10) phenyl;
(11) $NO_2$;
(12) —$CO_2R^4$;
(13) —$CON(R^4)_2$ wherein each $R^4$ is the same or different;
(14) —$S(O)_2R^{22}$;
(15) —$S(O)_2N(R^{20})_2$ wherein each $R^{20}$ is the same or different;
(16) —$N(R^{24})S(O)_2R^{22}$;
(17) —CN;
(18) —$CH_2OH$;
(19) —$OCH_2CH_2OR^{22}$;
(20) alkyl (e.g., $C_1$ to $C_4$, such as methyl);
(21) substituted phenyl wherein said phenyl has 1 to 3 substituents independently selected from alkyl, halogen, —CN, —$NO_2$, —$OCHF_2$, -Oalkyl;
(22) -Oalkylaryl (preferably -Oalkylphenyl or -Oalkyl-substituted phenyl, e.g., —$OCH_2$dichlorophenyl, such as —$OCH_2$-2,6-dichlorophenyl or —$OCH_2$-2-chloro-6-fluorophenyl) wherein said aryl group is optionally substituted with 1 to 3 independently selected halogens; or
(23) phenyl;
(B) X is selected from alkyl (e.g., —$(CH_2)_q$— or branched alkyl) or —$S(O)_2$—;
(C) Y represents
(1) a single bond (i.e., Y represents a direct bond from $M^1$ to $M^2$); or
(2) Y is selected from —C(O)—, —C(S)—, —$(CH_2)_q$—, or —$NR^4C(O)$—; with the provisos that:
(a) when $M^1$ is N, then Y is not —$NR^4C(O)$—; and
(b) when Y is a bond, then $M^1$ and $M^2$ are both carbon;
(D) $M^1$ and $M^2$ are independently selected from C or N;
(E) Z is selected from: $C_1$–$C_6$ alkyl, —$SO_2$—, —C(O)— or —$C(O)NR^4$—;
(F) $R^2$ is selected from:
(1) a six-membered heteroaryl ring having 1 or 2 heteroatoms independently selected from N or N—O (i.e., N-oxide), with the remaining ring atoms being carbon;
(2) a five-membered heteroaryl ring having 1 to 3 heteroatoms selected from nitrogen, oxygen, or sulfur with the remaining ring atoms being carbon; or
(3) an alkyl group, preferably a $C_1$ to $C_4$ alkyl group, more preferably methyl;
(4) an aryl group, e.g., phenyl or substituted phenyl (preferably phenyl), wherein said substituted phenyl is substituted with 1 to 3 substituents independently selected from: halogen, -Oalkyl, —$OCF_3$, —$CF_3$, —CN, —$NO_2$, —$NHC(O)CH_3$, or —$O(CH_2)_qN(R^{10A})_2$;
(5) —$N(R^{11A})_2$ wherein each $R^{11A}$ is independently selected from: H, alkyl (e.g., i-propyl) or aryl (e.g., phenyl), preferably one $R^{11A}$ is H and the other is phenyl or alkyl (e.g., i-propyl);
(6) a group of the formula:

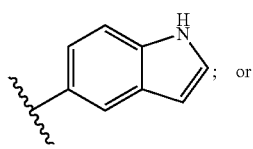; or (7) a heteroarylheteroaryl group, e.g.,

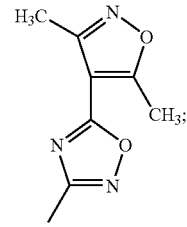

said five membered heteroaryl ring ((F)(2) above) or six-membered heteroaryl ring ((F)(1) above) is optionally substituted with 1 to 3 substituents selected from:
(a) halogen;
(b) hydroxyl;
(c) lower alkyl;
(d) lower alkoxy;
(e) —$CF_3$;
(f) —$NR^4R^5$;
(g) phenyl;
(h) —$NO_2$;
(i) —$C(O)N(R^4)_2$ (wherein each $R^4$ is the same or different);
(j) —$C(O)_2R^4$; or
(k) phenyl substituted with 1 to 3 substituents independently selected from: halogen, -Oalkyl, —$OCF_3$, —$CF_3$, —CN, —$NO_2$ or —$O(CH_2)_qN(R^{10A})_2$;
(G) $R^3$ is is selected from:
(1) aryl;
(2) heteroaryl;
(3) heterocycloalkyl
(4) alkyl; or
(5) cycloalkyl;

wherein said aryl or heteroaryl $R^3$ groups is optionally substituted with 1 to 3 substituents independently selected from:
(a) halogen (e.g., Br, F, or Cl, preferably F or Cl);
(b) hydroxyl (i.e., —OH);
(c) lower alkoxy (e.g., $C_1$ to $C_6$ alkoxy, preferably $C_1$ to $C_4$ alkoxy, more preferably $C_1$ to $C_2$ alkoxy, most preferably methoxy);
(d) -Oaryl (i.e., aryloxy);
(e) —$SR^{22}$;
(f) —$CF_3$;
(g) —$OCF_3$;
(h) —$OCHF_2$;
(i) —$NR^4R^5$;
(j) phenyl;
(k) —$NO_2$,
(l) —$CO_2R^4$;
(m) —$CON(R^4)_2$ wherein each $R^4$ is the same or different;
(n) —$S(O)_2R^{22}$;
(o) —$S(O)_2N(R^{20})_2$ wherein each $R^{20}$ is the same or different;
(p) —$N(R^{24})S(O)_2R^{22}$;
(q) —CN;
(r) —$CH_2OH$;
(s) —$OCH_2CH_2OR^{22}$; or
(t) alkyl;
(H) $R^4$ is selected from:
(1) hydrogen;
(2) $C_1$–$C_6$ alkyl;

(3) cycloalkyl;
(4) cycloalkylalkyl (e.g., cyclopropyl-CH$_2$— or cyclohexyl-CH$_2$—);
(5) heterocycloalkylalky (e.g., tetrahydrofuranyl-CH$_2$—);
(6) bridged bicyclic cycloalkyl ring, such as, for example:

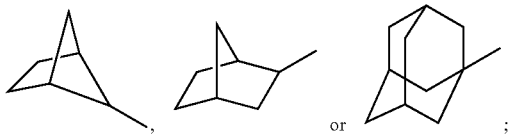

(7) aryl having a fused heterocycloalkyl ring bound to said aryl ring, preferably the heteroatoms in said heterocycloalkyl ring are two oxygen atoms, e.g., phenyl having a heterocycloalkyl ring bound to said phenyl ring, such as

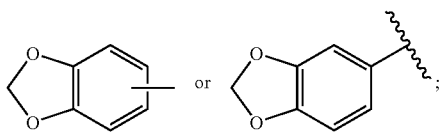

(8) aryl;
(9) arylalkyl;
(10) alkylaryl;
(11) —(CH$_2$)$_d$CH(R$^{12A}$)$_2$ wherein d is 1 to 3 (preferably 1), and each R$^{12A}$ is independently selected from phenyl or substituted phenyl, said substituted phenyl being substituted with 1 to 3 substituents independently selected from: halogen, -Oalkyl, —OCF$_3$, —CF$_3$, —CN, or —NO$_2$, e.g.,

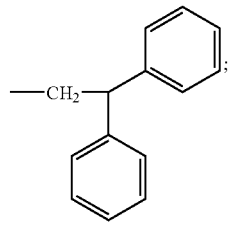

(12) heterocycloalkylheteroaryl, e.g.,

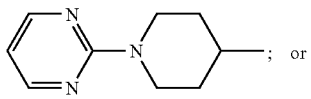

(13) —(C$_1$ to C$_6$)alkylene-O—R$^{22}$ (e.g., —C$_3$H$_6$OCH$_3$);

wherein the aryl R$^4$ group, the aryl portion of the arylalkyl R$^4$ group, or the aryl portion of the alkylaryl R$^4$ group is optionally substituted with 1 to 3 substituents independently selected from:
(a) halogen;
(b) hydroxyl;
(c) lower alkyl;
(d) lower alkoxy;
(e) —CF$_3$;
(f) —N(R$^{20}$)(R$^{24}$),
(g) phenyl;
(h) —NO$_2$;
(i) —C(O)N(R$^{20}$)$_2$ (wherein each R$^{20}$ is the same or different),
(j) —C(O)R$^{22}$;
(i) —(CH$_2$)$_k$-cycloalkyl;
(j) —(CH$_2$)$_q$-aryl; or
(k) —(CH$_2$)$_m$—OR$^{22}$;

(I) each R$^{4B}$ is independently selected from: H, heteroaryl (e.g., pyridyl), alkyl, alkenyl (e.g., allyl), a group of the formula

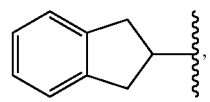

arylalkyl (e.g., benzyl), or arylalkyl wherein the aryl moiety is substitued with 1–3 substituents independently selected from: halogen (e.g. —CH$_2$-p-Clphenyl); preferably one R$^{4B}$ is H;

(J) R$^5$ is selected from: hydrogen, C$_1$–C$_6$ alkyl, —C(O)R$^{20}$ (e.g., —C(O)alkyl, such as —C(O)CH$_3$), —C(O)$_2$R$^{20}$, —C(O)N(R$^{20}$)$_2$ (wherein each R$^{20}$ is the same or different);

(K) each R$^{10A}$ is independently selected from H or C$_1$ to C$_6$ alkyl (e.g., methyl), or each R$^{10A}$, taken together with the nitrogen atom to which they are bound, forms a 4 to 7 membered heterocycloalkyl ring;

(L) R$^{12}$ is
(1) selected from alkyl, hydroxyl, alkoxy, or fluoro, provided that when R$^{12}$ is hydroxy or fluoro then R$^{12}$ is not bound to a carbon adjacent to a nitrogen; or
(2) R$^{12}$ forms an alkyl bridge from one ring carbon to another ring carbon, an example of such a bridged ring system is:

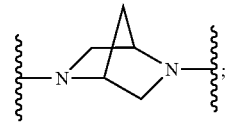

(M) R$^{13}$ is
(1) selected from alkyl, hydroxyl, alkoxy, or fluoro, provided that when R$^{13}$ is hydroxy or fluoro then R$^{13}$ is not bound to a carbon adjacent to a nitrogen; or
(2) R$^{13}$ forms an alkyl bridge from one ring carbon to another ring carbon, an example of such a bridged ring system is:

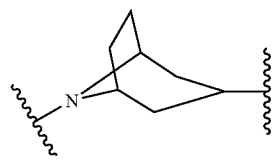

(N) R$^{20}$ is selected from hydrogen, alkyl, or aryl, wherein said aryl group is optionally substituted with from 1 to 3 groups independently selected from: halogen, —CF$_3$, —OCF$_3$, hydroxyl, or methoxy; or when two R$^{20}$ groups are present, said two $R^{20}$ groups taken together with the nitrogen to which they are bound form a five or six membered heterocyclic ring;

(O) $R^{22}$ is selected from: heterocycloalkyl (e.g., morpholinyl or pyrrolidinyl), alkyl or aryl, wherein said aryl group is optionally substituted with 1 to 3 groups independently selected from halogen, —$CF_3$, —$OCF_3$, hydroxyl, or methoxy;

(P) $R^{24}$ is selected from: hydrogen, alkyl, —$SO_2R^{22}$, or aryl, wherein said aryl group is optionally substituted with 1 to 3 groups independently selected from halogen, —$CF_3$, —$OCF_3$, hydroxyl, or methoxy;

(Q) a is 0 to 2;
(R) b is 0 to 2;
(S) k is 1 to 5;
(T) m is 2 to 5;
(U) n is 1, 2 or 3 with the proviso that when $M^1$ is N, then n is not 1;
(V) p is 1, 2 or 3 with the proviso that when $M^2$ is N, then p is not 1;
(W) q is 1 to 5; and
(X) r is 1, 2, or 3 with the proviso that when r is 2 or 3, then $M^2$ is C and p is 1.

This invention also provides a pharmaceutical composition comprising an effective amount of compound of Formula I, and a pharmaceutically acceptable carrier.

This invention further provides a method of treating: allergy, allergy-induced airway (e.g., upper airway) responses, congestion (e.g., nasal congestion), hypotension, cardiovascular disease, hypotension, diseases of the GI tract, hyper and hypo motility and acidic secretion of the gastrointestinal tract, obesity, sleeping disorders (e.g., hypersomnia, somnolence, and narcolepsy), disturbances of the central nervous system, attention deficit hyperactivity disorder ADHD), hypo and hyperactivity of the central nervous system (for example, agitation and depression), and/or other CNS disorders (such as Alzheimer's, schizophrenia, and migraine) comprising administering to a patient in need of such treatment (e.g., a mammal, such as a human being) an effective amount of a compound of Formula I.

This invention further provides a method of treating: allergy comprising administering to a patient in need of such treatment (e.g., a mammal, such as a human being) an effective amount of a compound of Formula I.

This invention further provides a method of treating: allergy-induced airway (e.g., upper airway) responses comprising administering to a patient in need of such treatment (e.g., a mammal, such as a human being) an effective amount of a compound of Formula I.

This invention further provides a method of treating: congestion (e.g., nasal congestion) comprising administering to a patient in need of such treatment (e.g., a mammal, such as a human being) an effective amount of a compound of Formula I.

This invention further provides a pharmaceutical composition comprising an effective amount of a compound of Formula I, and an effective amount of a $H_1$ receptor antagonist in combination with a pharmaceutically acceptable carrier.

This invention further provides a method of treating: allergy, allergy-induced airway (e.g., upper airway) responses, and congestion (e.g., nasal congestion) comprising administering to a patient in need of such treatment (e.g., a mammal, such as a human being) an effective amount of a compound of Formula I in combination with an effective amount of an $H_1$ receptor antagonist.

This invention further provides a method of treating: allergy comprising administering to a patient in need of such treatment (e.g., a mammal, such as a human being) an effective amount of a compound of Formula I in combination with an effective amount of an $H_1$ receptor antagonist.

This invention further provides a method of treating: allergy-induced airway (e.g., upper airway) responses comprising administering to a patient in need of such treatment (e.g., a mammal, such as a human being) an effective amount of a compound of Formula I in combination with an effective amount of an $H_1$ receptor antagonist.

This invention further provides a method of treating: congestion (e.g., nasal congestion) comprising administering to a patient in need of such treatment (e.g., a mammal, such as a human being) an effective amount of a compound of Formula I in combination with an effective amount of an $H_1$ receptor antagonist.

DETAILED DESCRIPTION OF THE INVENTION

As used herein, the following terms have the following meanings, unless indicated otherwise:

alkyl-(including the alkyl portions of alkylamino, alkylaryl, arylalkyl, alkoxy and dialkylamino)-represents straight and branched carbon chains and contains from one to twenty carbon atoms, preferably one to six carbon atoms;

alkylaryl-represents an alkyl group, as defined above, bound to an aryl group, as defined below, wherein said aryl group is bound to the compound;

aryl (including the aryl portion of alkylaryl and arylalkyl)-represents a carbocyclic group containing from 6 to 15 carbon atoms and having at least one aromatic ring (e.g., aryl is a phenyl or naphthyl ring), with all available substitutable carbon atoms of the carbocyclic group being intended as possible points of attachment, said carbocyclic group being optionally substituted with one or more (e.g., 1 to 3 ) substituents independently selected from: halo, alkyl, hydroxy, alkoxy, phenoxy, $CF_3$, amino, alkylamino, dialkylamino, —$COOR^{20}$ or —$NO_2$;

arylalkyl-represents an aryl group, as defined above, bound to an alkyl group, as defined above, wherein said alkyl group is bound to the compound;

bridged bicyclic cycloalkyl rings-represents a cycloalkyl ring, as defined below, having an alkyl (as defined above) bridge from one ring carbon to another ring carbon thereby forming a bicyclic cycloalkyl ring, e.g.,

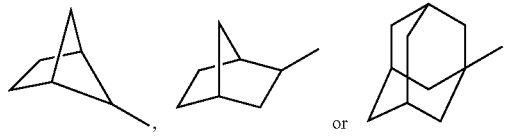

cycloalkyl-represents saturated carbocyclic rings of from 3 to 20 carbon atoms, preferably 3 to 7 carbon atoms;

halo (halogen)-represents fluoro, chloro, bromo and iodo; and heteroaryl-represents cyclic groups, having at least one heteroatom selected from O, S or N, said heteroatom interrupting a carbocyclic ring structure and having a sufficient number of delocalized pi electrons to provide aromatic character, with the aromatic heterocyclic groups preferably containing from 2 to 14 carbon atoms; examples include but are not limited to isothiazolyl, isoxazolyl, oxazolyl, furazanyl, triazolyl, thiazolyl, thienyl, furanyl (furyl), pyrrolyl, pyrazolyl, pyranyl, pyrimidinyl, pyrazinyl, pyridazinyl, pyridyl (e.g., 2-, 3-, or 4-pyridyl), pyridyl N-oxide (e.g., 2-, 3-, or 4-pyridyl N-oxide), triazinyl, pteridinyl, indolyl (benzopyrrolyl), pyridopyrazinyl, isoqinolinyl, quinolinyl, naphthyridinyl, wherein said pyridyl N-oxide can be represented as:

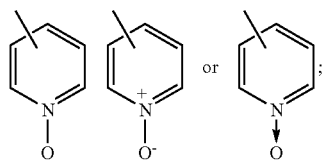

heterocycloalkyl-represents a saturated, carbocylic ring containing from 3 to 15 carbon atoms, preferably from 4 to 6 carbon atoms, which carbocyclic ring is interrupted by 1 to 3 hetero groups selected from —O—, —S—, —SO—, —SO$_2$ or —NR$^{40}$— wherein R$^{40}$ represents H, C$_1$ to C$_6$ alkyl, arylalkyl, —C(O)R$^{20}$, —C(O)OR$^{20}$, or —C(O)N(R$^{20}$)$_2$ (wherein each R$^{20}$ is independently selected); examples include but are not limited to 2- or 3-tetrahydrofuranyl, 2- or 3-tetrahydrothienyl, 2-, 3- or 4-piperidinyl, 2- or 3-pyrrolidinyl, 2- or 3-piperizinyl, 2- or 4-dioxanyl, 1,3-dioxolanyl, 1,3,5-trithianyl, pentamethylene sulfide, perhydroisoquinolinyl, decahydroquinolinyl, trimethylene oxide, azetidinyl, 1-azacycloheptanyl, 1,3-dithianyl, 1,3,5-trioxanyl, morpholinyl, thiomorpholinyl, 1,4-thioxanyl, and 1,3,5-hexahydrotriazinyl, thiazolidinyl, tetrahydropyranyl;

heterocycloalkylheteroaryl-represents a heteroaryl group as defined above bound to a heterocycloalkyl as defined above;

lower alkyl-represents an alkyl group, as defined above, that comprises 1 to 6 carbon atoms, preferably 1–4 carbon atoms;

lower alkoxy-represents an alkoxy group whose alkyl moiety comprises 1 to 6 carbon atoms, preferably 1–4 carbon atoms;

Ac-represents acetyl (i.e., CH$_3$C(O)—);

t-BOC-represents t-butyloxycarbonyl;

Ci/mmol-represents curie/mmol (a measure of specific activity);

DCC-represents dicyclohexylcarbodiimide;

DEC-represents 2-diethylaminoethyl chloride hydrochloride;

DIC-represenets diisopropylcarbodiimide;

DMF-represents dimethylformamide;

DMSO-represents dimethylsulfoxide;

EtOAc-represents ethyl acetate;

EtOH-represents ethanol;

FMOC-represents 9-fluorenylmethoxycarbonyl;

HOBT-represents 1-hydroxybenzotriazole;

Ki-represents inhibition constant for substrate/receptor complex;

LiOH-represents lithium hydroxide;

Me-represents methyl;

MeOH-represents methanol;

nM-represents nanomolar;

PyBOP—represents benzotriazole-1-yl-oxy-trispyrrolidino-phosphonium hexaflurophosphate;

TFA-represents trifluoroacetic acid;

THF-represents tetrahydrofuran;

Also, as used herein, "upper airway" usually means the upper respiratory system—i.e., the nose, throat, and associated structures.

Also, as used herein, "effective amount" generally means a therapeutically effective amount.

Lines drawn into the rings indicate that the indicated bond may be attached to any of the substitutable ring carbon atoms.

Certain compounds of the invention may exist in different isomeric (e.g., enantiomers, diastereoisomers and geometric) forms. The invention contemplates all such isomers both in pure form and in admixture, including racemic mixtures. Enol forms are also included.

The compounds of this invention are ligands for the histamine H$_3$ receptor. The compounds of this invention can also be described as antagonists of the H$_3$ receptor, or as H$_3$ antagonists.

The compounds of the invention are basic and form pharmaceutically acceptable salts with organic and inorganic acids. Examples of suitable acids for such salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous sodium hydroxide, potassium carbonate, ammonia and sodium bicarbonate. The free base forms differ from their corresponding salt forms somewhat in certain physical properties, such as solubility in polar solvents, but the salts are otherwise equivalent to their corresponding free base forms for purposes of this invention.

The compounds of Formula I can exist in unsolvated as well as solvated forms, including hydrated forms, e.g., hemi-hydrate. In general, the solvated forms, with pharmaceutically acceptable solvents such as water, ethanol and the like are equivalent to the unsolvated forms for purposes of the invention.

The compounds of this invention can be combined with an H$_1$ receptor antagonist (i.e., the compounds of this invention can be combined with an H$_1$ receptor antagonist in a pharmaceutical composition, or the compounds of this invention can be administered with H$_1$ receptor antagonist).

Numerous chemical substances are known to have histamine H$_1$ receptor antagonist activity and can therefore be used in the methods of this invention. Many H$_1$ receptor antagonist useful in the methods of this invention can be classified as ethanolamines, ethylenediamines, alkylamines, phenothiazines or piperidines. Representative H$_1$ receptor antagonists include, without limitation: astemizole, azatadine, azelastine, acrivastine, brompheniramine, cetirizine, chlorpheniramine, clemastine, cyclizine, carebastine, cyproheptadine, carbinoxamine, descarboethoxyloratadine (also known as SCH-34117), diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine and triprolidine. Other compounds can readily be evaluated to determine activity at $H_1$ receptors by known methods, including specific blockade of the contractile response to histamine of isolated guinea pig ileum. See for example, WO98/06394 published Feb. 19, 1998.

Those skilled in the art will appreciate that the $H_1$ receptor antagonist is used at its known therapeutically effective dose, or the $H_1$ receptor antagonist is used at its normally prescribed dosage.

Preferably, said $H_1$ receptor antagonist is selected from: astemizole, azatadine, azelastine, acrivastine, brompheniramine, cetirizine, chlorpheniramine, clemastine, cyclizine, carebastine, cyproheptadine, carbinoxamine, descarboethoxyloratadine, diphenhydramine, doxylamine, dimethindene, ebastine, epinastine, efletirizine, fexofenadine, hydroxyzine, ketotifen, loratadine, levocabastine, meclizine, mizolastine, mequitazine, mianserin, noberastine, norastemizole, picumast, pyrilamine, promethazine, terfenadine, tripelennamine, temelastine, trimeprazine or triprolidine.

More preferably, said $H_1$ receptor antagonist is selected from: astemizole, azatadine, azelastine, brompheniramine, cetirizine, chlorpheniramine, clemastine, carebastine, descarboethoxyloratadine, diphenhydramine, doxylamine, ebastine, fexofenadine, loratadine, levocabastine, mizolastine, norastemizole, or terfenadine.

Most preferably, said $H_1$ receptor antagonist is selected from: azatadine, brompheniramine, cetirizine, chlorpheniramine, carebastine, descarboethoxy-loratadine (also known as SCH-34117), diphenhydramine, ebastine, fexofenadine, loratadine, or norastemizole.

Even more preferably, said $H_1$ antagonist is selected from: loratadine, descarboethoxyloratadine, fexofenadine or cetirizine. Still even more preferably, said $H_1$ antagonist is loratadine or descarboethoxyloratadine.

In one preferred embodiment, said $H_1$ receptor antagonist is loratadine.

In another preferred embodiment, said $H_1$ receptor antagonist is descarboethoxyloratadine.

In still another preferred embodiment, said $H_1$ receptor antagonist is fexofenadine.

In yet another preferred embodiment, said $H_1$ receptor antagonist is cetirizine.

Preferably, in the above methods, allergy-induced airway responses are treated.

Also, preferably, in the above methods, allergy is treated.

Also, preferably, in the above methods, nasal congestion is treated.

In the methods of this invention wherein a combination of an $H_3$ antagonist of this invention (compound of Formula I) is administered with a $H_1$ antagonist, the antagonists can be administered simultaneously, consecutively (one after the other within a relatively short period of time), or sequentially (first one and then the other over a period of time). In general, when the antagonists are administered consecutively or sequentially, the $H_3$ antagonist of this invention (compound of Formula I) is administered first.

Compounds of Formula I include compounds of the formula:

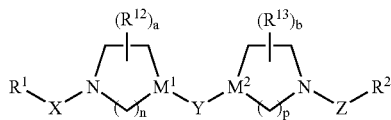

(V)

wherein $R^1$, X, n, $M^1$, $R^{12}$, a, Y, $M^2$, $R^{13}$, b, p, Z and $R^2$ are as defined for Formula I.

Compounds of Formula I also include compounds of the formula:

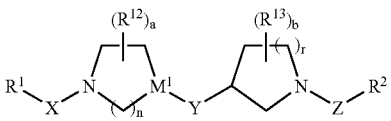

(VI)

wherein $R^1$, X, n, $M^1$, $R^{12}$, a, Y, $R^{13}$, b, r, Z and $R^2$ are as defined for Formula I.

$R^1$ is preferably selected from:
(1) substituted aryl, more preferably substituted phenyl;
(2) substituted heteroaryl, more preferably substituted isoxazolyl; or
(3) formula IVA wherein each $R^3$ is independently selected, more preferably each $R^3$ is alkyl, most preferably each $R^3$ is $C_1$ to $C_4$ alkyl, even more preferably each $R^3$ is the same moiety, and still more preferably each $R^3$ is methyl.

Preferably, when $R^1$ is a substituted phenyl group, the phenyl group has 1 to 3 substituents and the substituents are independently selected from:
(1) —C(O)N($R^4$)$_2$, preferably each $R^4$ is independently selected, more preferably each $R^4$ is independently selected from H or arylalkyl (e.g., —CH$_2$CH$_2$phenyl), most preferably one $R^4$ is H and the other is arylalkyl, even more preferably one $R^4$ is H and the other $R^4$ is —CH$_2$CH$_2$phenyl;
(2) halo, more preferably 1 to 3 halos independently selected from Br, Cl and F;
(3) —S(O)$_2$R$^{22}$, more preferably $R^{22}$ is heterocycloalkyl, most preferably $R^{22}$ is morpholinyl or pyrrolidinyl;
(4) —OCF$_3$;
(5) —OCHF$_2$; or
(6) —S(O)$_2$N($R^{20}$)$_2$, more preferably each $R^{20}$ is independently selected from alkyl or substituted phenyl, most preferably $C_1$ to $C_4$ alkyl or halo substituted phenyl, even more preferably methyl or chlorophenyl; still more preferably each $R^{20}$ is methyl or one $R^{20}$ is methyl and the other $R^{20}$ is chlorophenyl.

Preferably, when $R^1$ is a substituted isoxazolyl group the isoxazolyl group has 1 or 2 substituents independently selected from:
(1) alkyl, more preferably $C_1$ to $C_4$ alkyl, most preferably methyl; or
(2) substituted phenyl, more preferably halo substituted phenyl (1 to 3 halo groups, preferably one halo group), most preferably chloro substituted phenyl (e.g., chlorophenyl).

More preferably the isoxazolyl is substituted with two alkyl groups (most preferably two methyl groups), or one halophenyl group (most preferably chlorophenyl).
Examples of $R^1$ groups include but are not limited to:
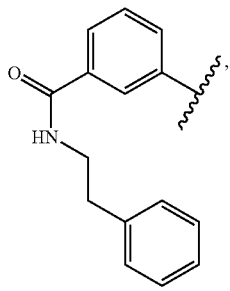 (a)
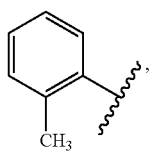 (b)
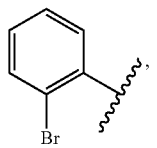 (c)
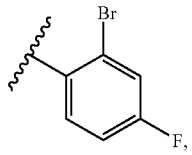 (d)
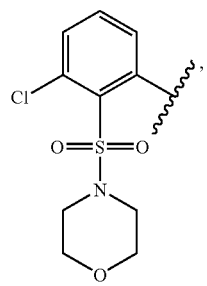 (e)
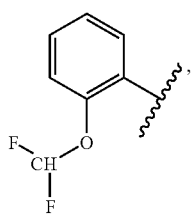 (f)
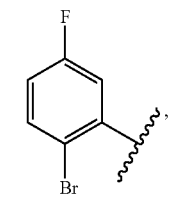 (g)
-continued
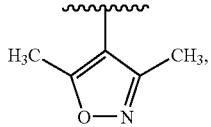 (h)
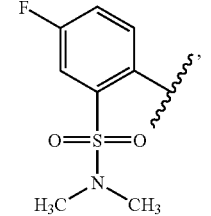 (i)
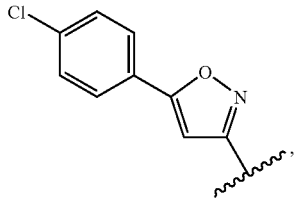 (j)
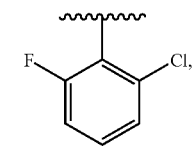 (k)
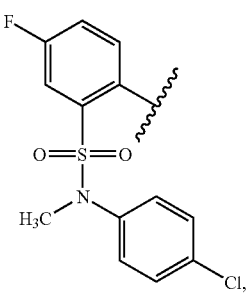 (l)
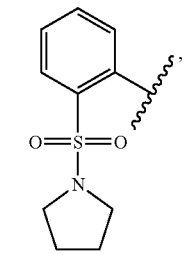 (m)
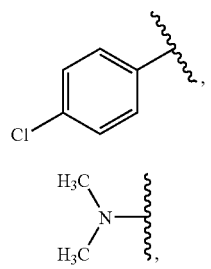 (n)
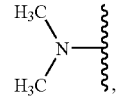 (o)

-continued (p)
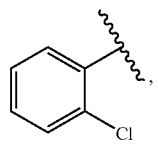

(q)
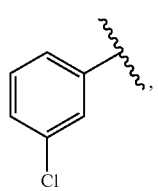, (r)
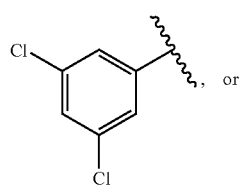, or (s)
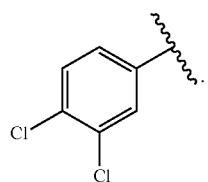.

Preferably X is selected from —CH$_2$— (i.e., q is preferably 1) or —SO$_2$—. More preferably X is —CH$_2$—.
Preferably n is 2.
Preferably M$^1$ is N.
Preferably Y is —C(O)—.
Preferably M$^2$ is C.
Preferably p is 2.
Preferably r is 1.
Preferably Z is a C$_1$ to C$_6$ alkyl group. More preferably Z is —CH$_2$— or

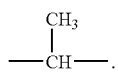.

Most preferably Z is —CH$_2$—.
Preferably R$^2$ is a six membered heteroaryl ring or a substituted six membered heteroaryl ring, and more preferably the heteroaryl ring contains one nitrogen atom. Preferably the substituted heteroaryl ring is substituted with one —NR$^4$R$^5$, and more preferably the substituent is —NH$_2$. Most preferably R$^2$ is selected from

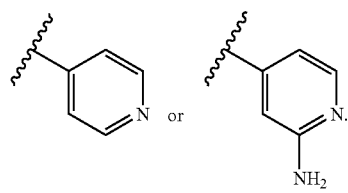

Even more preferably R$^2$ is

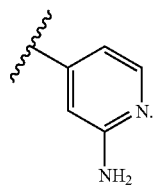

Preferably a is 0 and therefore there is no R$^{12}$ group present.
Preferably b is 0 or 1, more preferably 0. When b is 1 R$^{13}$ is preferably —OH. More preferably, when b is 1, R$^{13}$ is —OH bound to the M$^2$ substituent and M$^2$ is C.
Representative compounds of this invention include, but are not limited to: Compounds 18 (Example 1), 25 (Example 2), 26 (Example 3), 31 (Example 4), 33 (Example 5), 37 (Example 6), 41 (Example 7), 45 (Example 8), 49 (Example 9), 51 (Example 10), 52 (Example 11), 57 (Example 12), 58 to 67, 73 to 84, 89 to 157, 159 to 168, 212 to 269, 271 to 272, 276 to 282, 284, 285, 287 to 300, 306, 309 to 319, 321 to 336, 338 to 340, 342 to 349, 351 to 361, 363 to 371, 374 to 377, 380 to 383, 387 to 390, 392 to 406, and 408 to 410.
Preferred compounds are Compounds 93, 276, 306, 317, 331, 332, 333, 336, 366, 343, 366, 367, 374, and 376
More preferred compounds are Compounds 306, 332, 333, 336, 366, 374, and 376.
Structures for the above compounds are given below.
The following processes may be employed to produce compounds of the invention.

Step 1

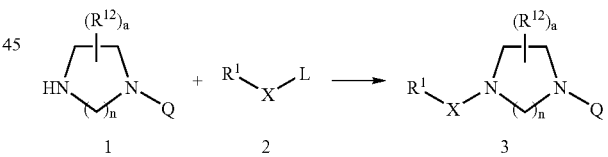

In Step 1, compound 1, in which Q is a protecting group such as a carbamate, amide, or a substituted benzylic group, is allowed to react with compound 2, in which L is a leaving group such as a halogen atom, in a suitable solvent such as THF, DMSO or DMF in the presence of a base such as a tertiary amine or an inorganic base such as Na$_2$CO$_3$ at a temperature sufficient to achieve a reasonable reaction rate. R$^{12}$, M$^1$, n, a, R$^1$, and X are as defined above. Alternatively, in the case when X is —(CH$_2$)$_q$—, L can equal an aldehyde group, CHO and X is —(CH$_2$)$_{q-1}$—. In that case, compounds 1 and 2 are combined in a solvent such as trifluoroethanol in the presence of sieves. A reducing agent, such as NaBH(OAc)$_3$ or NaCNBH$_3$ is added and the reaction stirred at a temperature suitable to complete the reaction.

Step 2

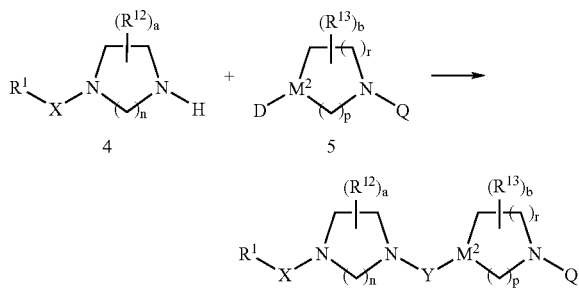

In Step 2, the protecting group Q is removed. When said protecting group is a carbamate such as t-BOC, dilute acid is used. In the case of a benzyl group, catalytic hydrogenation is used.

Step 3

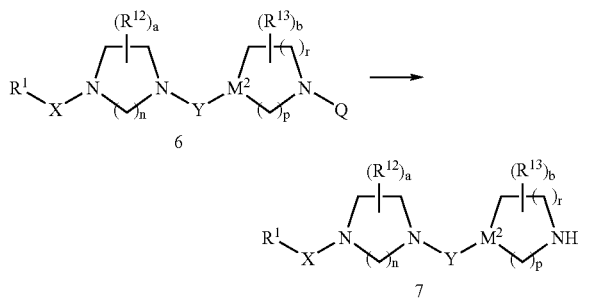

When Y is C=O, amine 4 can be coupled to acid 5 (D is $CO_2H$, $M^2$ is carbon) using a number of methods well known in the art such as DCC or PyBOP. Alternatively, the acid 5 can be activated by conversion to the acid chloride or mixed anhydride and then reacted with the amine 4 to give 6. Suitable protecting groups for 5 include t-Boc or the like. Alternatively, when Y is —$CH_2$— and $M^2$ is carbon, D can be —$CH_2$-L (where L is a halogen) and the reaction can be performed as in Step 1.

Step 4

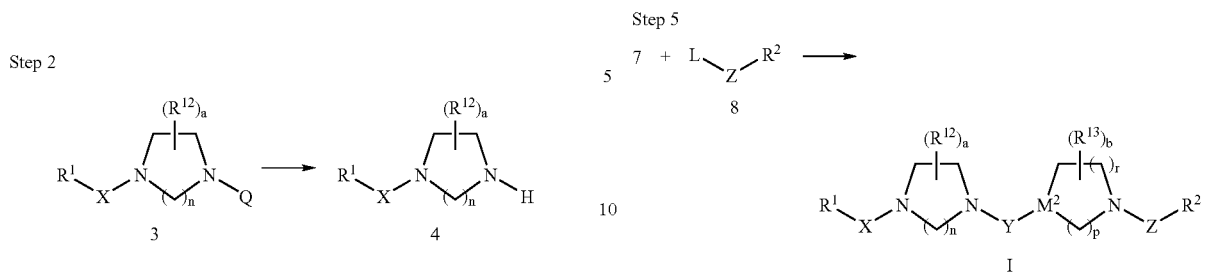

Compound 6 in which the protecting group is a t-Boc can be deprotected under acidic conditions such as HCl in dioxane or TFA in $CH_2Cl_2$ to give the amine 7.

Step 5

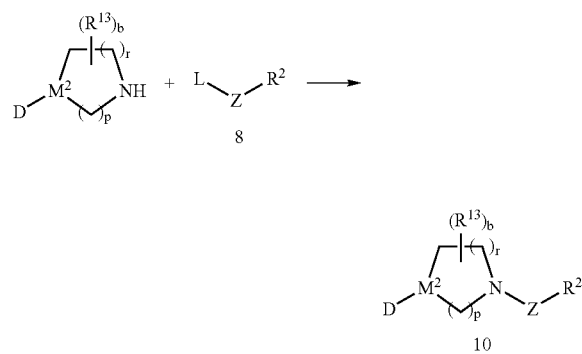

The amine 7 can be alkylated by reaction with the electrophile 8. In one case, L represents a carbonyl group and Z is a branched or straight chain alkyl group. Compounds 7 and 8 are combined in a solvent such as $CH_2Cl_2$ in the presence of sieves. After a suitable amount of time, a reducing agent such as $NaBH(OAc)_3$ is added to give the product I. Alternatively, when L is a halogen atom such as Cl or Br, and Z is a branched or straight chain alkyl group or —$SO_2$— 7 and 8 are combined in a solvent such as DMF in the presence of a tertiary amine base to give the product I.

Alternative Synthesis

An alternative approach to the synthesis of compounds of Formula I is given below.

Step 1

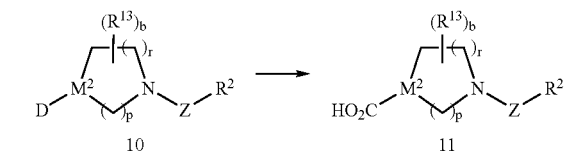

In the same manner as Step 5, compounds 8 and 9 can be converted to 10. In the case when $M^2$ is carbon, D is $CO_2$alkyl and when $M^2$ is nitrogen, D is a protecting group such as the BOC group.

Step 2

Compound 10 (D is $CO_2$alkyl) is saponified in a mixed solvent such as EtOH or MeOH and water, or THF, water, and MeOH using an alkali metal base such as LiOH or NaOH at a temperature of from 50 to 100° C. to give 11.

Compound 11 can be combined with compound 4 as described in Step 3.

Step 3 (D is a protecting group)

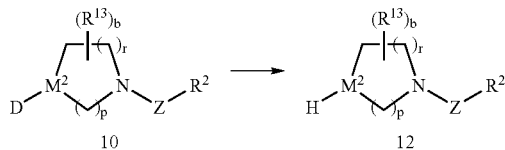

Compound 10, in which D is a protecting group such as t-Boc and $M^2$ is nitrogen, can be deprotected under acidic conditions such as HCl in dioxane or TFA in $CH_2Cl_2$ to give the amine 12.

Step 4

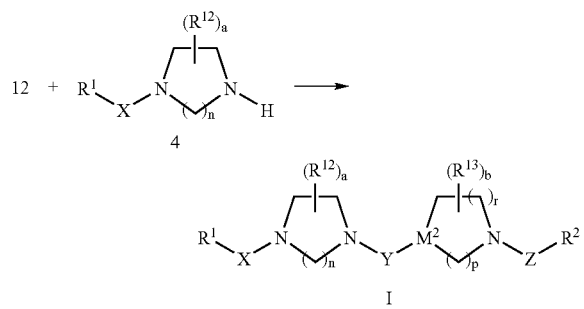

Compound 12 can be coupled with compound 4 using a reagent such as carbonyl diimidazole or the like in a solvent such as THF, ether or the like at a temperature from 0 to 60° C. to give compound I (Y is C=O, $M^1$ and $M^2$ are nitrogen).

Compound I (Y is C=O) can be converted to compound I (Y is C=S) by treatment of I with a reagent such as Lawesson's reagent in a solvent such as toluene at a temperature from 20 to 100° C.

Synthesis ($M^1$ and $M^2$ are Carbon)

Step 1

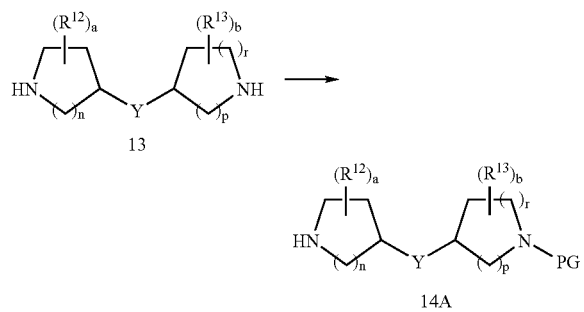

A solution of an excess of 13 in a solvent such as THF, $CH_2Cl_2$ or the like is treated with a reagent such as $BOC_2O$ or an acid chloride or anhydride at a temperature of from −20° C. to +300° C. to produce 14A in which PG is a BOC group, or an amide. Alternatively, a solution of an excess of 13 in a solvent such as THF, $CH_2Cl_2$ or the like is treated with a substituted or unsubstituted benzyl bromide in the presence of a base such as triethylamine to give 14A in which PG is a substituted benzyl group.

Step 2

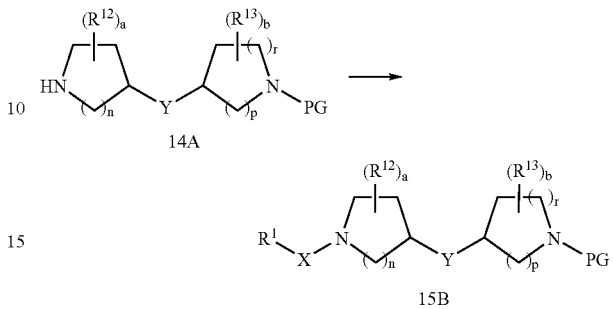

In Step 2, compound 14A, in which PG is a protecting group such as a carbamate, amide, or a substituted benzylic group, is allowed to react with compound 2, in which L is a leaving group such as a halogen atom, in a suitable solvent such as THF, DMSO or DMF in the presence of a base such as a tertiary amine or an inorganic base such as $Na_2CO_3$ at a temperature sufficient to achieve a reasonable reaction rate to give compound 15A. $R^{12}$, $R^{13}$, $M^1$, n, p, a, b, r, $R^1$, and X are as defined for formula I. Alternatively, in the case when X is —$(CH_2)_q$—, L can equal an aldehyde group, CHO, and X is —$(CH_2)_{q-1}$—. In that case, compounds 14A and 2 are combined in a solvent such as trifluoroethanol in the presence of sieves and stirred for a suitable time. A reducing agent, such as $NaBH(OAc)_3$ or $NaCNBH_3$ is added and the mixture stirred at a temperature suitable to complete the reaction.

Step 3

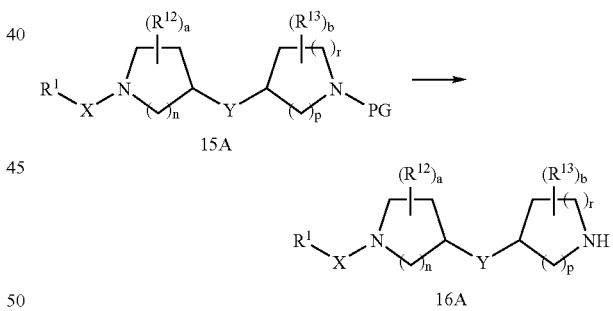

Compound 15A in which the protecting group is t-Boc can be deprotected under acidic conditions such as HCl in dioxane or TFA in $CH_2Cl_2$ to give the amine 16A. Alternatively, when PG is a benzyl group, it can be removed by catalytic hydrogenation using a catalyst such as Pd/C.

Step 4

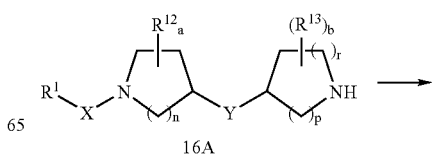

-continued

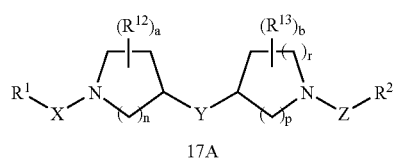

17A

The amine 16A can be alkylated by reaction with the electrophile 8. In one case, L represents a carbonyl group and Z is a branched or straight chain alkyl group. Compounds 16A and 8 are combined in a solvent such as $CH_2Cl_2$ in the presence of sieves. After a suitable amount of time, a reducing agent such as $NaBH(OAc)_3$ is added to give the product 17A. Alternatively, when L is a halogen atom such as Cl or Br, and Z is a branched or straight chain alkyl group or $—SO_2—$ 16A and 8 are combined in a solvent such as DMF in the presence of a tertiary amine base to give the product 17A.

Compounds useful in this invention are exemplified by the following examples which should not be construed as limiting the scope of the disclosure. Alternative mechanistic pathways and analogous structures within the scope of the invention may be apparent to those skilled in the art.

EXAMPLE 1

Step 1:

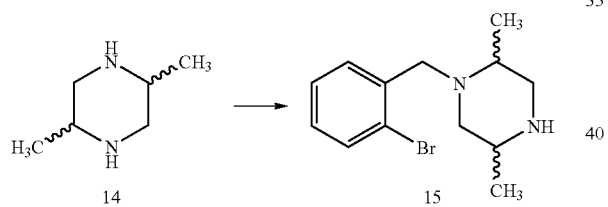

Compound 14 (5 g, 43.8 mmol) and 2-bromobenzaldehyde (4.1 g, 22.2 mmol) were combined in $CH_2Cl_2$ (130 mL) and stirred for 2 h. $Na(OAc)_3BH$ (6.4 g, 30.2 mmol) was added and the mixture stirred overnight at room temperature. The reaction was then washed with saturated $NaHCO_3$ and brine and dried. Filtration and concentration gave a residue which was purified by flash column chromatography (5% to 10% $MeOH/NH_3$ in $CH_2Cl_2$) to give 15 (3.44 g, 55%) Mass spectrum=453 (M+H).

Step 2:

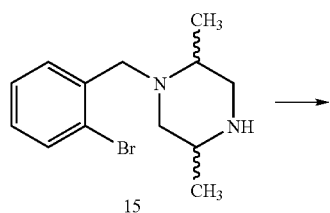

15

-continued

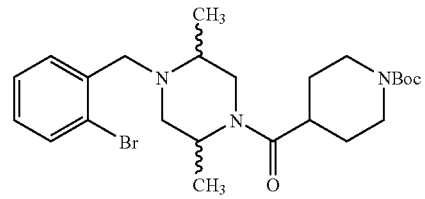

16

A solution of 15 (2 g, 7.06 mmol), N-Boc isonipecotic acid (1.47 g, 6.42 mmol) and PyBOP (3.34 g, 6.42 mmol) in $CH_2Cl_2$ (20 mL) was cooled to 0° C. and diisopropyl ethyl amine (2.49 g, 19.3 mmol) was added. After 1 minute, the cooling bath was removed and the reaction stirred at room temperature for 48 hours. The reaction was washed with saturated $NaHCO_3$, dried $(Na_2SO_4)$, and concentrated and the residue was purified by flash column chromatography (30% to 50% ethyl acetate in hexane) to give 16 (3 g, 60%).

Step 3:

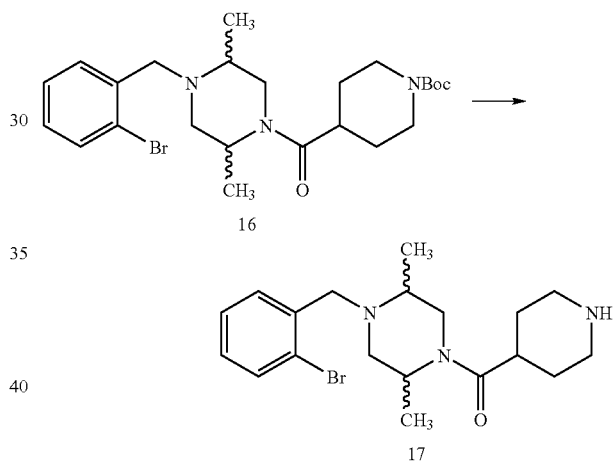

A solution of 16 (3 g, 6.07 mmol) in $CH_2Cl_2$ (100 mL) at 0° C. was treated with 4 N HCl (8 mL) and the reaction stirred at room temperature overnight. The solvent was removed in vacuo and the residue was dissolved in water and the pH adjusted to 8 by addition of aqueous NaOH. The water was removed in vacuo and the residue dissolved in MeOH, filtered and concentrated to give 17 as a white solid (3 g, >100%) which was used as is. Mass spectrum: 394 (M+H).

Step 4:

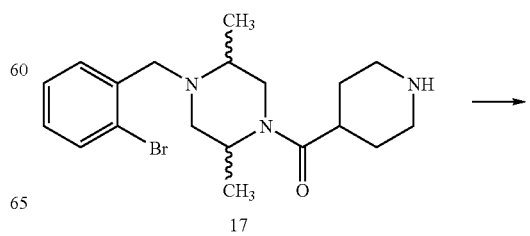

17

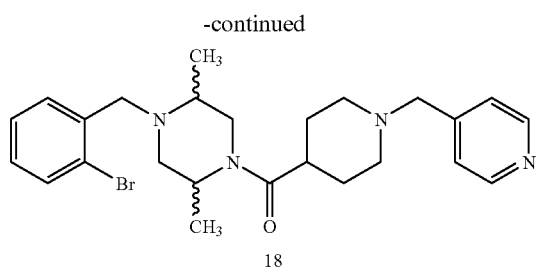
18

In a manner similar to that described in Example 1, Step 1, 17 (0.95 g, 2.4 mmol) and pyridine-4-carboxaldehyde (0.22 g, 2.02 mmol) was converted to 18 (0.57 g, 58%). Mass spectrum: 485 (M+H).

EXAMPLE 2

Step 1:

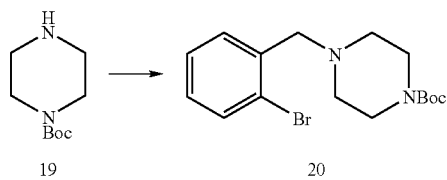

In a manner similar to that described in Example 1, Step 1, 19 (5 g, 26 mmol) and 2-bromobenzaldehyde (4.1 g, 21.7 mmol) was converted to 20 (6.2 g, 80%).

Step 2:

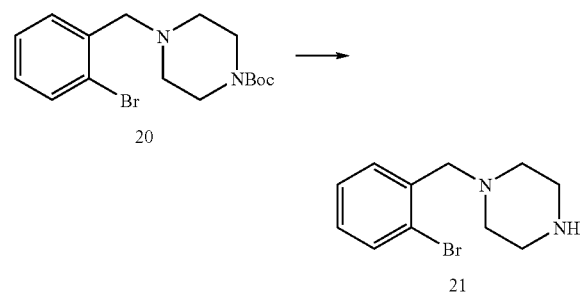

In a manner similar to that described in Example 1, Step 3, 20 (6.2 g, 17.5 mmol) was converted to 21 (5.5 g, 100%).

Step 3

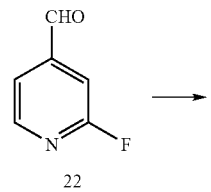

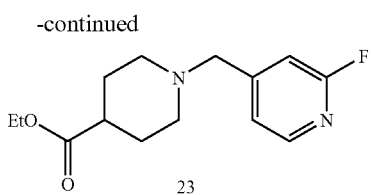

In a manner similar to that described in Example 1, Step 1, 22 (0.45 g, 3.6 mmol) and ethyl isonipecotate (0.7, 4.4 mmol) were converted to 23 (0.45 g, 64%).

Step 4:

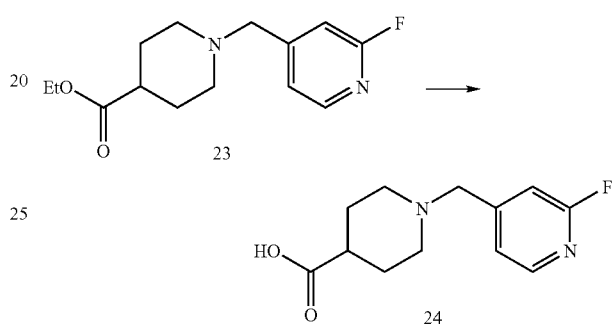

A solution of 23 (0.45 g, 1.69 mmol) in MeOH (10 mL) was treated with 1 N KOH (5 mL) and the mixture was heated to 60° C. overnight. The reaction was cooled and concentrated. The residue was dissolved in water and extracted with ethyl acetate. The pH of the aqueous phase was adjusted to 6–7 by addition of 1N HCl. The water was removed in vacuo and the residue taken up in MeOH, filtered and concentrated to give 24 which was used in the next step as is.

Step 5:

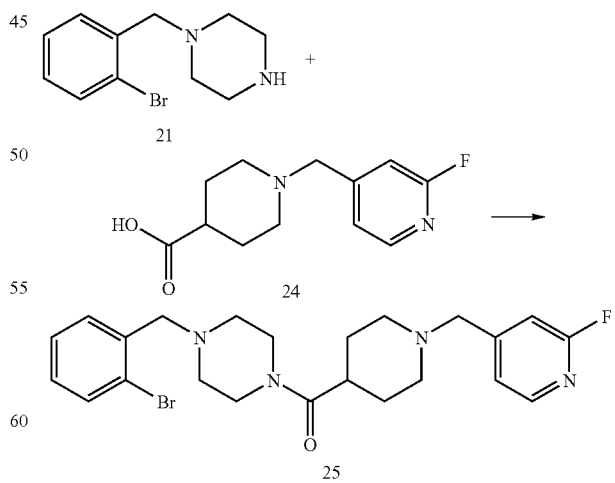

In a manner similar to that described in Example 1, Step 2, 21 (0.35 g, 1.39 mmol) and 24 (0.3 g, 1.26 mmol) was converted to 25 (0.50 g, 66%). Mass spectrum: 475 (M+H).

EXAMPLE 3

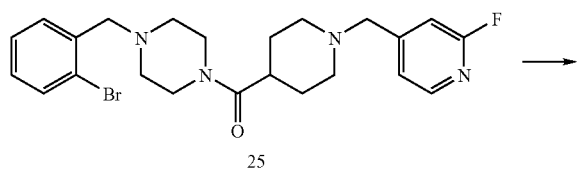
25

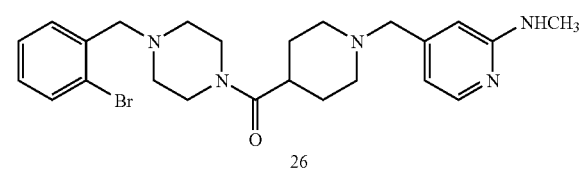
26

To a solution of 25 (0.11 g, 0.23 mmol) in 2-propanol (6 mL) in a pressure vessel was added triethylamine (7 mL) and methylamine hydrochloride (3 g, 44.4 mmol) and the reaction heated to 95° C. for 6 days. The reaction was cooled and the solvent removed in vacuo. The residue was dissolved in ethyl acetate and washed with half saturated NaHCO$_3$. The organic layer was dried and concentrated, and the residue purified on a flash column (20% MeOH in ethyl acetate) to give 26 (40 mg, 36%). Mass spectrum: 486 (M+H).

EXAMPLE 4

Step 1:

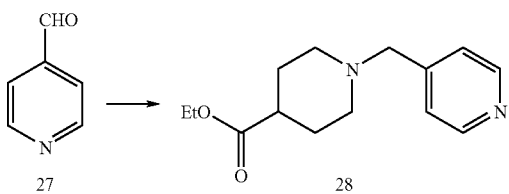

In a manner similar to that described in Example 1, Step 1, 27 (2 g, 18.3 mmol) and ethyl isonipecotate (3.5, 22 mmol) were converted to 28 (4.5 g, 99%).

Step 2:

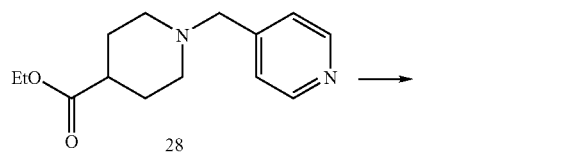

A solution of n-BuLi (3 mL of a 1.6 M solution in hexane, 4.8 mmol) in THF (25 mL) was treated at −25° C. with (i-Pr)$_2$NH (0.49 g, 4.8 mmol). The reaction was stirred for 1 h at 0° C. and then cooled to −70° C. Compound 28 (1.0 g, 4 mmol) in THF (3 mL) was added dropwise and the reaction stirred at −70° C. for 2 h and −50° C. for 2 h. The reaction was recooled to −70° C. and (1S)-(+)-(10-camphorsulfonyl)oxaziridine (1.04 g, 4.52 mmol) in THF (10 mL) was added. The reaction was stirred at −70° C. for 2 h and slowly warmed to room temperature overnight. The reaction was quenched by the addition of saturated aqueous NH$_4$Cl and extracted with EtOAc. The organic layer was dried and concentrated, and the residue purified by column chromatography (4% MeOH in ethyl acetate) to give 29 (0.75 g, 71%)

Step 3:

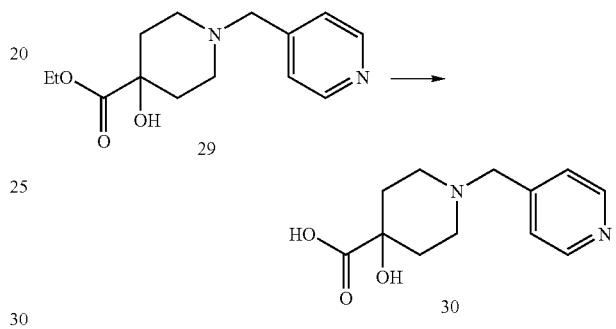

In a manner similar to that described in Example 2, Step 4, 29 (0.35 g, 1.32 mmol) was converted to 30 (0.32 g, 99%).

Step 4:

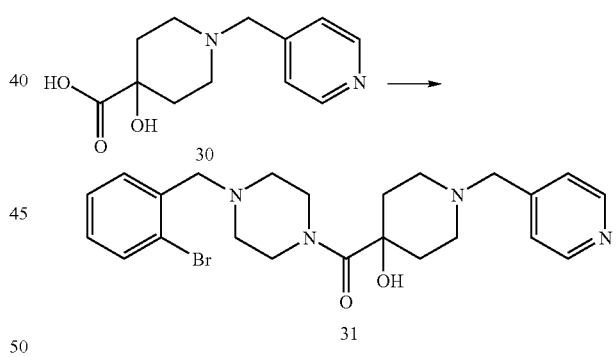

In a manner similar to that described in Example 1, Step 2, 30 (0.2 g, 0.85 mmol) was converted to 31 (0.10 g, 25%). Mass spectrum: 473 (M+H).

EXAMPLE 5

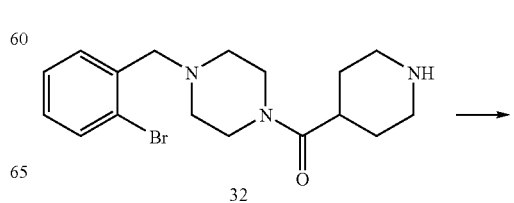
32

-continued

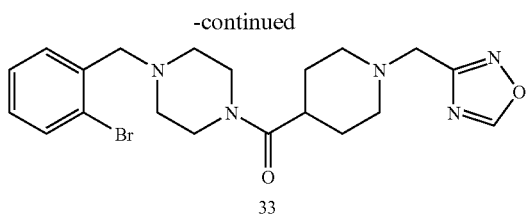
33

To a solution of 32 (0.52 g, 1.43 mmol; synthesized in the same manner as compound 17) and 3-chloromethyloxadiazole (0.25 g, 2.11 mmol) in toluene (10 mL) was added triethylamine (0.6 mL) and the reaction was heated to 75° C. overnight. The reaction was cooled, diluted with ethyl acetate and washed with saturated NaHCO₃. The organic layer was dried and concentrated and the residue purified by flash column chromatography (10% MeOH in ethyl acetate) to give 33 (0.2 g, 31%) Mass spectrum: 448 (M+H).

EXAMPLE 6

Step 1

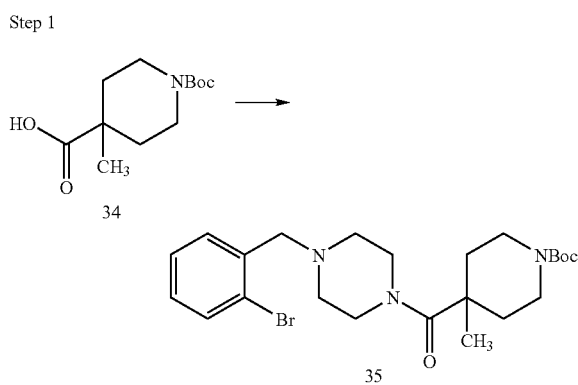

In a manner similar to that described in Example 1, Step 2, compound 34 (1.2 g, 4.93 mmol) was coupled with compound 21 (1.4 g, 5.43 mmol) to give compound 35 (1.7 g, 74%).

Step 2

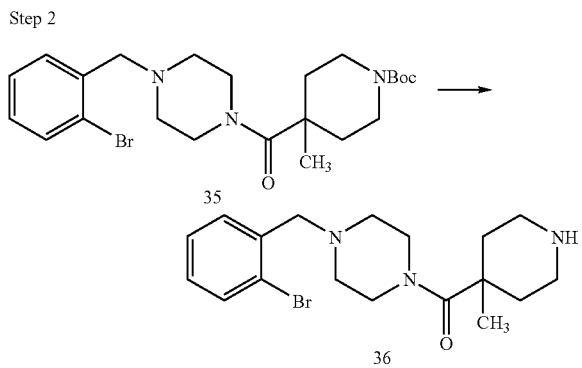

In a manner similar to that described in Example 1, Step 3, compound 35 (1.7 g, 3.54 mmol) was converted to 36 (1.3 g, 97%).

Step 3

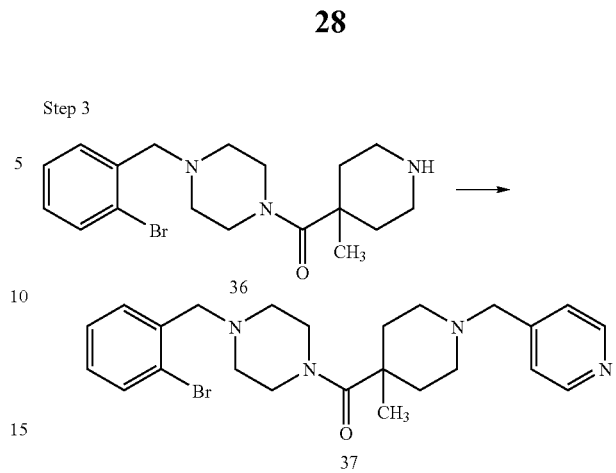

In a manner similar to that described in Example 1, Step 1, compound 36 (0.41 g, 1.08 mmol) was converted to 37 (0.2 g, 45%). Mass Spectrum: 471 (M+H).

EXAMPLE 7

Step 1

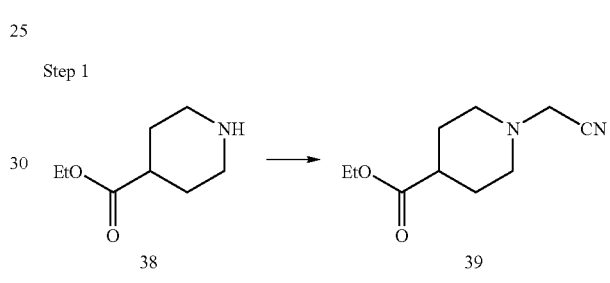

To a stirred mixture of 38 (2.0 g, 12.5 mmol) and Na₂CO₃ (1.45 g, 13.7 mmol) in acetone (15 mL) was added chloroacetonitrile (1.05 g, 13.7 mmol) and the reaction mixture stirred for 3 h at room temperature. The solvent was removed in vacuo and the residue partitioned between ethyl acetate and water. The ethyl acetate layer was dried (Na₂SO₄) and concentrated to give 37 (2.3 g, 94%) which was used as is.

Step 2

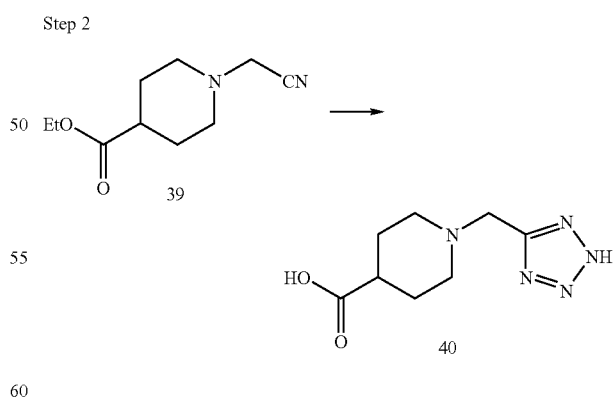

To a solution of 39 (2.2 g, 11.2 mmol) in toluene (20 mL) was added n-Bu₃Sn (5.7 g, 16.8 mmol) and the reaction heated to reflux for 48 h. Additional n-Bu₃Sn (0.5 mL) was added and the reaction was stirred at reflux for 6 h and at room temperature for 18 h. The reaction was cooled to room temperature, 5 N NaOH (35 mL) and hexane (35 mL) were added and the reaction was stirred for 2 h. The aqueous phase was separated and neutralized with concentrated HCl. The water was evaporated in vacuo and the residue taken up in MeOH, filtered, and the filtrate concentrated to give 40 (3.6 g) which was used in the next step without further purification.

Step 3

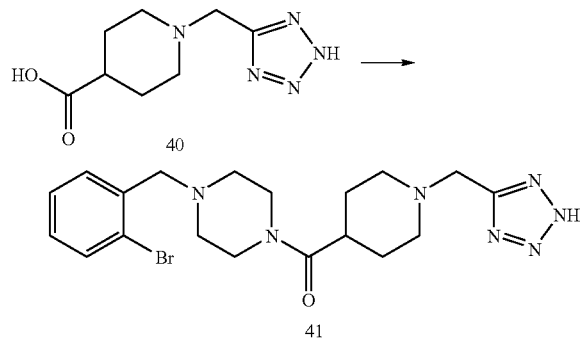

In a manner similar to that described in Example 1, Step 2, compound 40 (0.2 g, 0.95 mmol) was converted to 41 (0.2 g, 47%). Mass spectrum: 448 (M+H).

EXAMPLE 8

Step 1

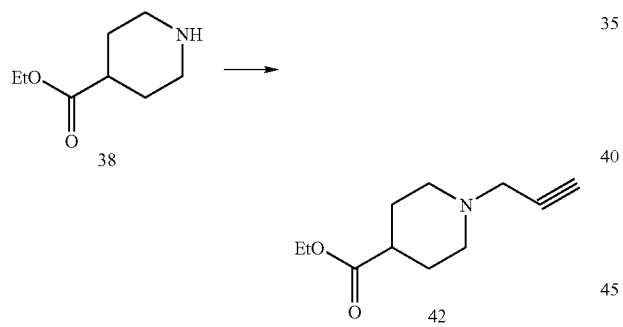

To a solution of 38 (2.57 g, 16 mmol) in THF (30 mL) was added propargyl bromide (1.34 g, 8.98 mmol) and the reaction heated to reflux overnight. After cooling to room temperature, the reaction was diluted with CH$_2$Cl$_2$ and washed with 1 N NaOH. The organic layer was dried and concentrated to give a residue which was purified by flash column chromatography (5% ethyl acetate in hexane) to give 42 (1.31 g, 75%). Mass spectrum: 196 (M+H).

Step 2

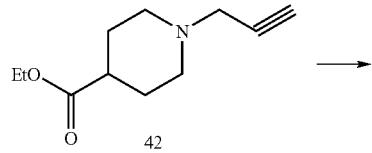

-continued

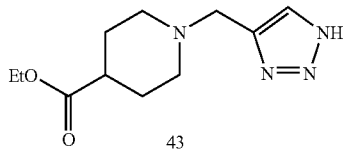

To a solution of 42 (0.5 g, 2.56 mmol) in toluene (10 mL) was added trimethylsilyl azide (0.62 g, 5.12 mmol) and the reaction was heated to reflux for 18 h. The reaction was cooled to room temperature, additional trimethylsilyl azide was added (0.7 mL). The reaction was stirred at 50° C. for 8 days and 110° C. for 10 days. The solvent was evaporated in vacuo, MeOH (100 mL) was added, and the MeOH removed in vacuo. The residue so obtained was chromatographed (4% MeOH in ethyl acetate) to give 43 (0.5 g, 82%) Mass spectrum: 239 (M+H).

Step 3

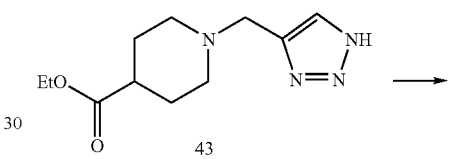

In a manner similar to that described in Example 2, Step 4, Compound 43 (0.5 g, 2.1 mmol) was converted to compound 44 (0.44 g, 100%).

Step 4

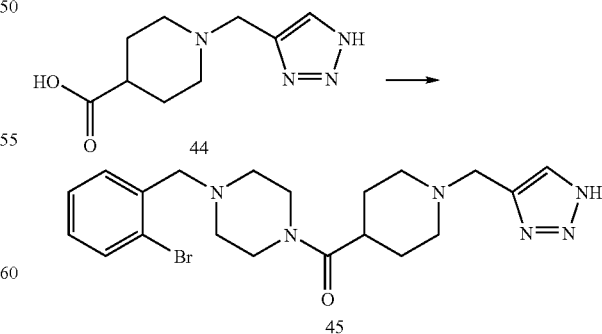

In a manner similar to that described in Example 1, Step 2, 44 (0.25 g, 1.2 mmol) and 21 ( 0.36, 1.4 mmol) were converted to 45 (0.11 g, 20%). Mass spectrum: 447 (M+H).

EXAMPLE 9

Step 1

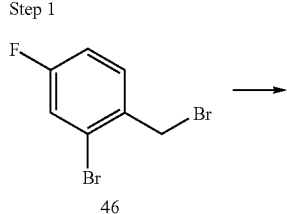

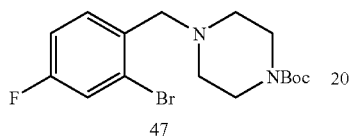

A solution of compound 46 (2 g, 7.5 mmol), 19 (1.6 g, 8.2 mmol) and triethylamine (3.1 mL) in toluene (30 mL) was heated to reflux overnight. The solvent was evaporated and the residue partitioned between ethyl acetate and saturated NaHCO$_3$. The organic layer was dried and concentrated and the residue purified by flash column chromatography (30% ethyl acetate in hexane) to give 47 (1.6 g, 78%).

Step 2

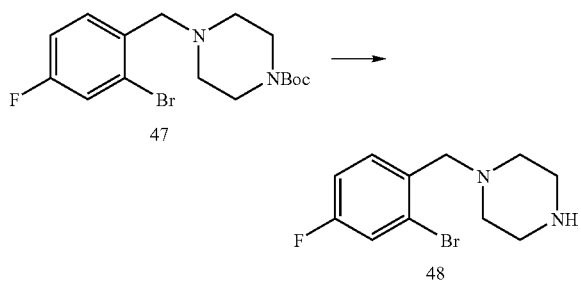

In a manner similar to that described in Example 1, Step 3, 47 (1.6 g, 4.3 mmol) was converted to 48 (1.5 g, 100%).

Step 3

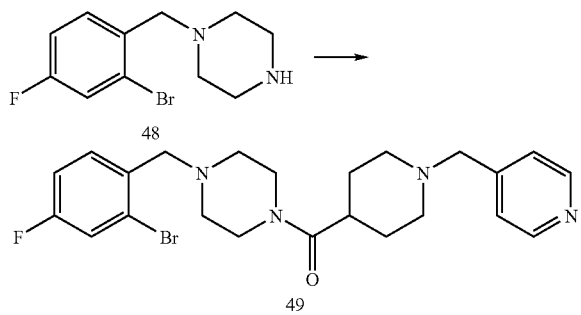

In a manner similar to that described in Example 1, Step 2, 48 (0.38 g, 1.1 mmol) was converted to 49 (0.15 g, 35%). Mass spectrum: 475 (M+H).

EXAMPLE 10

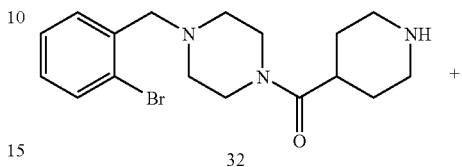

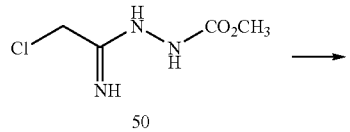

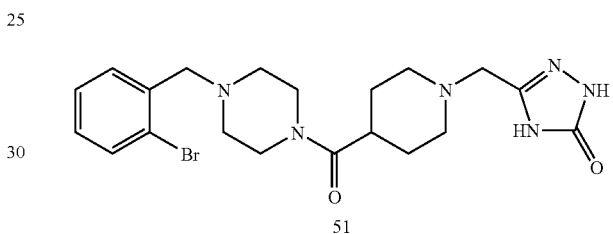

To a suspension of 32 (0.5 g, 1.14 mmol) in acetonitrile (5 mL) was added diisopropylethylamine (0.59 g, 4.56 mmol) followed after 10 min by 50 (0.23 g, 1.37 mmol). The mixture was stirred at room temperature for 48 h. The acetonitrile was removed, xylene (10 mL) was added and the reaction refluxed overnight. The reaction was cooled, diluted with ethyl acetate and washed with water. The organic layer was dried and concentrated and chromatographed (10% to 20% MeOH in ethyl acetate) to give 51 (0.13 g, 25%). Mass spectrum: 463 (M+H).

EXAMPLE 11

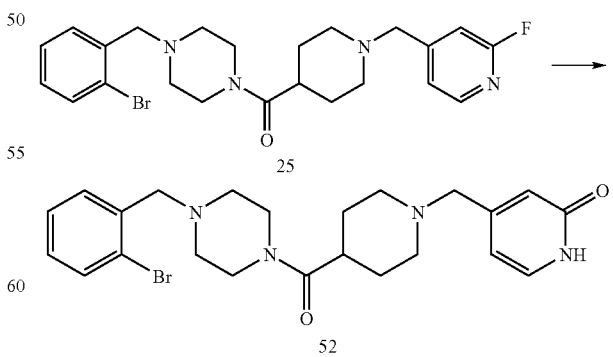

A solution of 25 (0.13 g, 0.27 mmol) in 1:1 5% HCl in DME/water (4 mL) was heated to 60° C. for 6 h. The reaction was cooled to room temperature, saturated NaHCO$_3$ and solid NaCl was added and the mixture was extracted with CH$_2$Cl$_2$. The combined organic layers were dried, concentrated and the residue purified by flash column chromatography (5–10% NH$_3$/MeOH in CH$_2$Cl$_2$) to give 52 (40 mg, 31%). Mass spectrum: 473 (M+).

EXAMPLE 12

Step 1

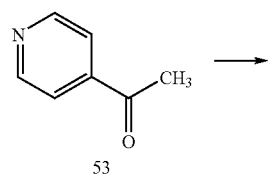
53

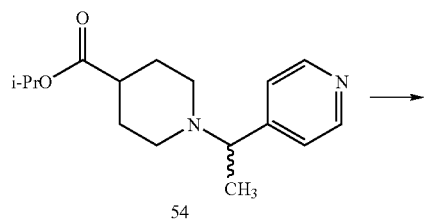
54

Compound 53 (3.6 g, 29.1 mmol), ethyl isonipecotate (5.8 g, 36.4 mmol) and Ti(OiPr)$_4$ (10.3 g, 36.4 mmol) were combined and stirred at room temperature overnight. CH$_2$Cl$_2$ (100 mL) was added followed by NaBH(OAc)$_3$ (8.6 g, 40.8 mmol) and the reaction stirred overnight. Saturated NaHCO$_3$ was added and the mixture filtered through Celite. The filter cake was washed with additional CH$_2$Cl$_2$, and the combined filtrates were washed with saturated NaHCO$_3$ and dried. Concentration gave a residue which was purified by flash column chromatography (8% MeOH in ethyl acetate) to give 54 (5 g, 83%). Mass spectrum: 277 (M+H).

Step 2

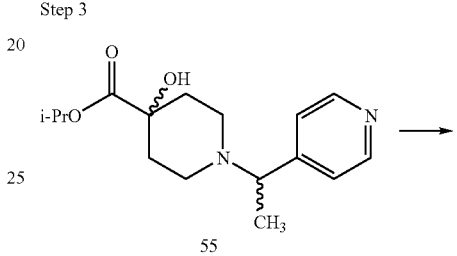
54

-continued

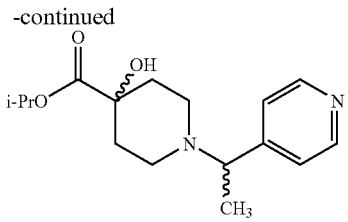
55

In a manner similar to that described in Example 4, Step 2, 54 (1 g, 3.6 mmol) was converted to 55 (0.4 g, 37%). Mass spectrum: 293 (M+H).

Step 3

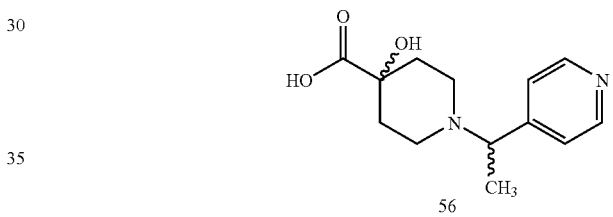
55

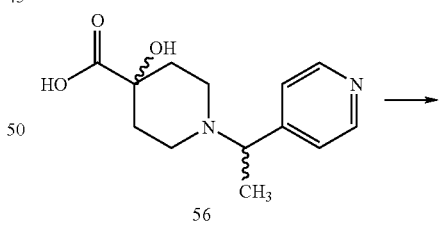
56

In a manner similar to that described in Example 2, Step 4, 55 (0.4 g, 1.4 mmol) was converted to 56 (0.4 g, 100%).

Step 4

56

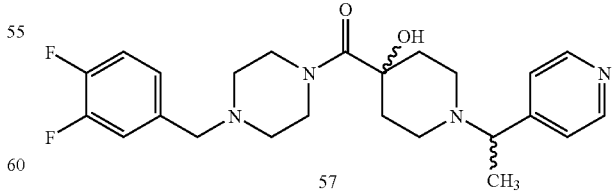
57

In a manner similar to that described in Example 1, Step 2, 56 (0.38 g, 1.6 mmol) was converted to 57 (0.36 g, 47%). Mass spectrum: 505 (M+H).

Using the procedures described in Examples 1–12, the compounds in Table 1 were synthesized:

TABLE 1

TABLE 1-continued

| Compound Number | Starting Material | Product |
|---|---|---|
| 52 | 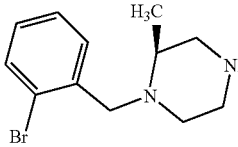 | 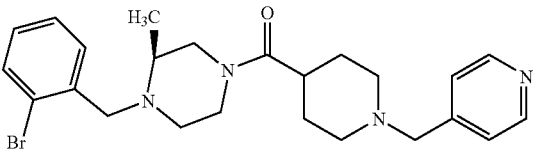 |
| 53 | 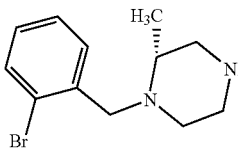 | 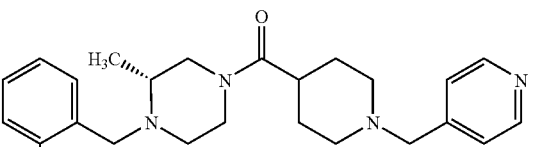 |

EXAMPLE 13

Step 1

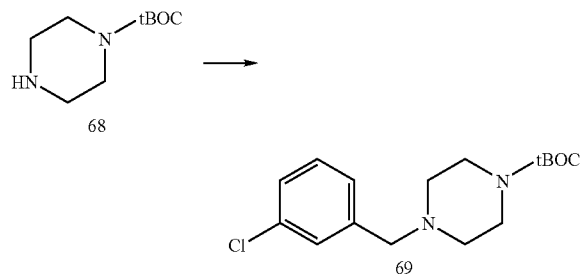

Dissolved amine 68 (25.0 g, 0.134 mol) in CH$_2$Cl$_2$ (500 mL) and added 3 A sieves (25 g), 3-chlorobenzaldehyde (28.3 g, 0.201 mol), and sodium triacetoxyborohydride (42.6 g, 0.201 mol). Stirred at 23° C. for 16 h and filtered. Washed filtrate with saturated NaHCO$_3$ then saturated NaCl. Dried organic extract (MgSO$_4$), filtered, and concentrated. Purified by silica gel chromatography (eluant: 20% EtOAc-hexane) to give 31.0 g (0.100 mol, 74%) of the product 69 as a yellow oil. MS for M+1: m/e 312.

Step 2

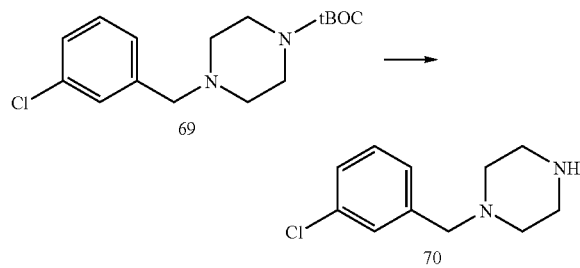

Dissolved compound 69 (27.0 g, 0.087 mol) in CH$_2$Cl$_2$ (500 mL) and added 1.0 N HCl in ether (275 mL, 0.275 mol). Stirred at 23° C. for 96 h. Filtered and washed with ether to give 20.0 g of the dihydrochloride salt of compound 70. Dissolved the dihydrochloride salt in 1 N NaOH (500 mL) and extracted with EtOAc. Dried combined organic extracts (MgSO$_4$), filtered, and concentrated to give 14.9 g (0.071 mol, 82%) of the product 70 as a yellow oil. MS (ES for M+1): m/e 211.

Step 3

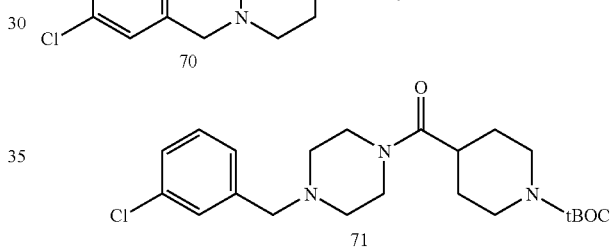

Combined compound 70 (13.03 g, 0.062 mol), N-tBOC-isonipecotic acid (21.38 g, 0.093 mol), HOBT (16.28 g, 0.12 mol), and DEC (23.01 g, 0.12 mol) in CH$_2$Cl$_2$ (400 mL). Stirred at 23° C. for 4 h. Added 2 N NaOH and extracted with CH$_2$Cl$_2$. Dried combined organic extracts (MgSO$_4$), filtered, and concentrated. Purified by silica gel chromatography (eluant: CH$_2$Cl$_2$ then 2% MeOH with NH$_3$—CH$_2$Cl$_2$) to give 25.0 g (0.059 mol, 95%) of the product 71 as a yellow oil. MS (ES for M+1): m/e 422.

Step 4

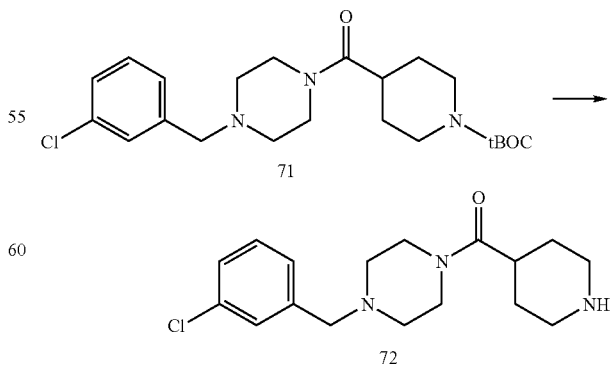

Dissolved compound 71 (20.0 g, 0.048 mol) in CH$_2$Cl$_2$ (250 mL) and cooled to 0° C. Added TFA (50 mL) and stirred at 23° C. for 3 h. Concentrated, added 6.25 N NaOH, and extracted with CH$_2$Cl$_2$. Dried combined organic extracts (MgSO$_4$), filtered, and concentrated. Purified by silica gel chromatography (eluant: CH$_2$Cl$_2$ then 5% MeOH with NH$_3$—CH$_2$Cl$_2$) to give 7.18 g (0.022 mol, 47%) of the product 72 as a yellow oil. MS (ES for M+1): m/e 322.

Step 5

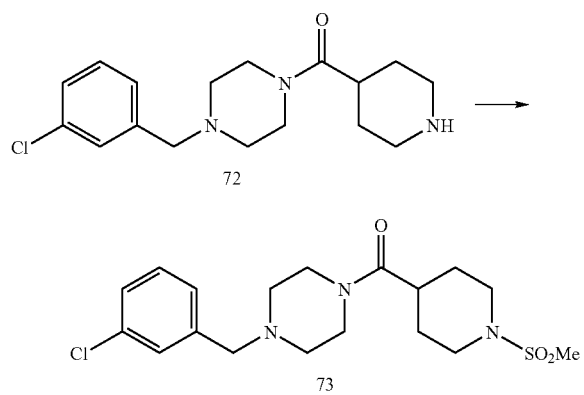

72

73

Dissolved compound 72 (255 mg, 0.79 mmol) in CH$_2$Cl$_2$ (10 mL) and cooled to 0° C. Added triethylamine (158 mg, 0.22 mL, 1.56 mmol) and mesyl chloride (115 mg, 0.078 mL, 1.01 mmol). Warmed to 23° C. and stirred for 16 h. Added saturated NaHCO$_3$ and extracted with CH$_2$Cl$_2$. Dried combined organic extracts (MgSO$_4$), filtered, and concentrated. Purified by silica gel chromatography (eluant: CH$_2$Cl$_2$ then 2% MeOH with NH$_3$—CH$_2$Cl$_2$) to give 164 mg (0.41 mmol, 52%) of the product 73 as a white foam. MS (ES for M+1): m/e 400.

Following the above procedure compound 74 was prepared:

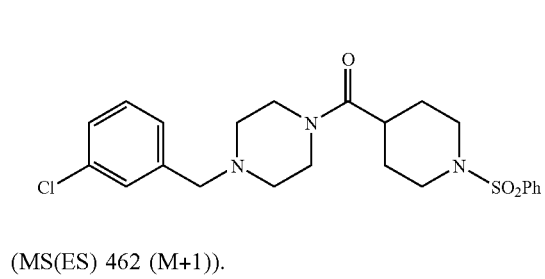

74

(MS(ES) 462 (M+1)).

EXAMPLE 14

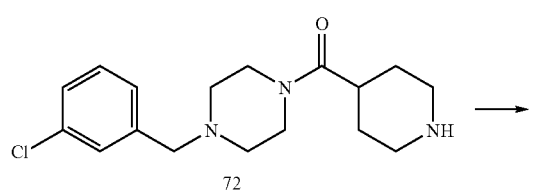

72

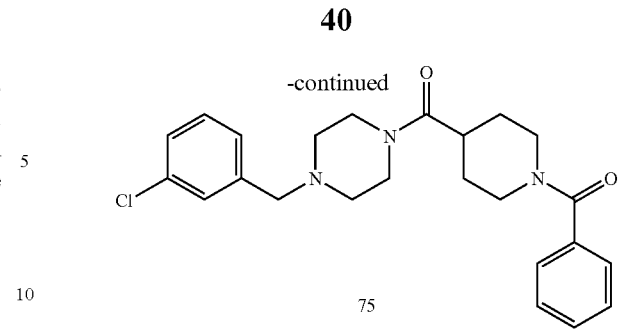

75

Dissolved compound 72 (250 mg, 0.78 mmol) and triethylamine (158 mg, 0.22 mL, 1.56 mmol) in CH$_2$Cl$_2$ (10 mL) and cooled to 0° C. Added benzoyl chloride (142 mg, 0.12 mL, 1.01 mmol). Warmed to 23° C. and stirred for 16 h. Added saturated NaHCO$_3$ and extracted with CH$_2$Cl$_2$. Dried combined organic extracts (MgSO$_4$), filtered, and concentrated. Purified by silica gel chromatography (eluant: CH$_2$Cl$_2$ then 3% MeOH with NH$_3$—CH$_2$Cl$_2$) to give 191 mg (0.45 mmol, 58%) of the product 75 as a white foam. MS (ES for M+1): m/e 426.

Following the above procedure compound 76 was prepared:

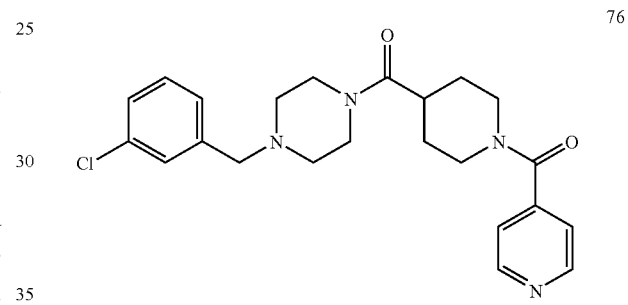

76

(MS(ES) 427 (M+1)).

EXAMPLE 15

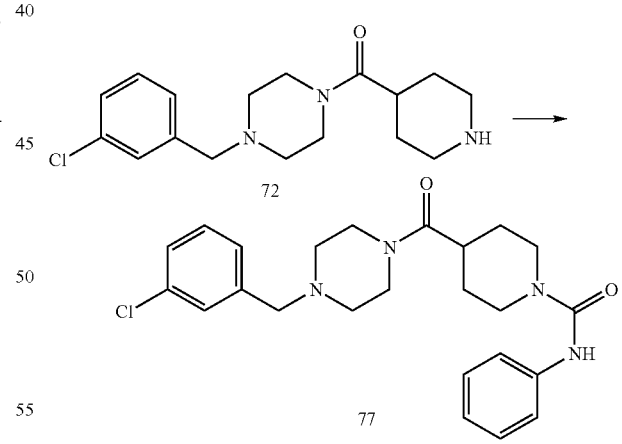

72

77

Dissolved compound 72 (250 mg, 0.78 mmol) and triethylamine (158 mg, 0.22 mL, 1.56 mmol) in dry THF (10 mL). Added phenylisocyanate (120 mg, 0.11 mL, 1.0 mmol) and stirred at 23° C. for 16 h. Added water and extracted with EtOAc. Dried combined organic extracts (MgSO$_4$), filtered, and concentrated. Purified by silica gel chromatography (eluant: CH$_2$Cl$_2$ then 3% MeOH with NH$_3$—CH$_2$Cl$_2$) to give 170 mg (0.39 mmol, 50%) of the product 77 as a white foam. MS (ES for M+1): m/e 441.

Following the above procedure compound 78 was prepared:

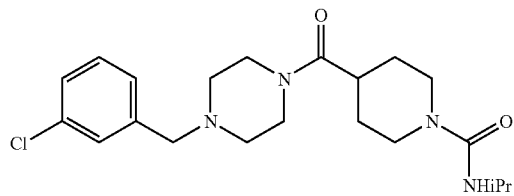

(MS(ES) 407 (M+1)).

EXAMPLE 16

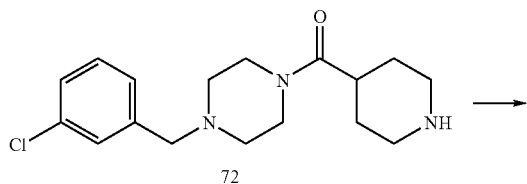

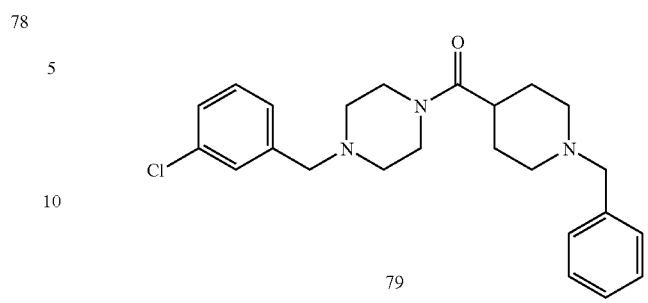

Combined compound 72 (550 mg, 1.71 mmol), benzaldehyde (109 mg, 1.03 mmol), 0.5 g of crushed 3A sieves, and sodium triacetoxyborohydride (347 mg, 1.64 mmol) in 2:1 $CH_2Cl_2$:EtOH (15 mL). Stirred at 23° C. for 16 h. Added saturated $NaHCO_3$ and extracted with $CH_2Cl_2$. Dried combined organic extracts ($MgSO_4$), filtered, and concentrated. Purified by silica gel chromatography (eluant: $CH_2Cl_2$ then 3% MeOH with $NH_3$—$CH_2Cl_2$) to give 260 mg (0.63 mmol, 37%) of the product 79 as a white foam. MS (ES for M+1): m/e 412.

Following the above procedure the compounds in Table 2 were prepared.

TABLE 2

| Compound Number | Compound | MS (ES) |
|---|---|---|
| 80 | ![structure] | 442 (M + 1) |
| 81 | ![structure] | 469 (M + 1) |

TABLE 2-continued

| Compound Number | Compound | MS (ES) |
| --- | --- | --- |
| 82 | | 413 (M + 1) |
| 83 | | 413 (M + 1) |
| 84 | | 429 (M + 1) |

EXAMPLE 17

General Procedure for Reductive Amination, Parallel Synthesis.

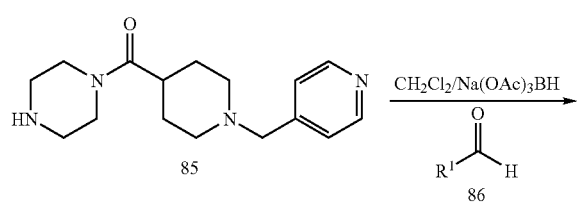

A solution of the amine 85 (0.063 mmol) and the aldehyde 86 (0.32 mmol, 1.0 M in dichloroethane) is treated with NaBH(OAc)$_3$ (0.32 mmol, 0.5 M in dichloroethane) and placed on shaker for an average period of 18 h. Where needed more NaBH(OAc)$_3$ is added to force the reaction into completion. Amberlyst-15 resin (~100 mg) is added and the reaction mixture shaken for an additional hour while monitoring by TLC (10% NH$_3$ saturated methanol in CH$_2$Cl$_2$, R$_f$~0.3) to ensure no amine product remained in solution. The resin is filtered and alternately washed six times with MeOH and dichloroethane. The resin is extracted by stirring twice, for 30 min, with 2N NH$_3$/MeOH (2 ml) and rinsing twice with MeOH (2 ml). The combined extracts are concentrated in vacuo to provide the desired product 65.

Using this procedure, the compounds listed in Table 3 were synthesized. In Table 3 X$_1$ represents the moiety:

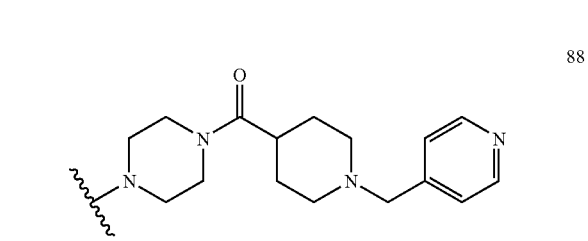

(i.e., the moiety 88 is compound 87 without the R$^1$CH$_2$- group).

TABLE 3

| Compound No. | R¹ | MS |
|---|---|---|
| 89 | 3-phenoxyphenyl-X₁ | 471.1 (MH⁺) |
| 90 | naphthalen-2-yl-X₁ | 429.1 (MH⁺) |
| 91 | 4-(acetylamino)phenyl-X₁ | 436.1 (MH⁺) |
| 92 | 4-isopropylphenyl-X₁ | 421.1 (MH⁺) |
| 93 | 2-bromophenyl-X₁ | 459.1581 (MH⁺) |
| 94 | phenyl-X₁ | 379.1 (MH⁺) |
| 95 | 3-hydroxyphenyl-X₁ | 395.1 (MH⁺) |
| 96 | 4-ethoxyphenyl-X₁ | 423.1 (MH⁺) |
| 97 | 4-chlorophenyl-X₁ | 413.1 (MH⁺) |
| 98 | 2-phenylethyl-X₁ | 407.1 (MH⁺) |
| 99 | 4-cyanophenyl-X₁ | 404.1 (MH⁺) |
| 100 | 5-(hydroxymethyl)furan-2-yl-X₁ | 399.1 (MH⁺) |
| 101 | 2-[(4-chlorophenyl)thio]phenyl-X₁ | 521.1 (M⁺) |
| 102 | 2-carboxyphenyl-X₁ | 423.1 (MH⁺) |
| 103 | 3,4-dimethoxyphenyl-X₁ | 439.1 (MH⁺) |
| 104 | benzyl-X₁ | 393.1 (MH⁺) |
| 105 | 4-methoxyphenyl-X₁ | 409.1 (MH⁺) |
| 106 | 5-(3-nitrophenyl)furan-2-yl-X₁ | 490.1 (MH⁺) |
| 107 | 2-methoxyphenyl-X₁ | 409.1 (MH⁺) |
| 108 | 4-hydroxy-3-methylphenyl-X₁ | 409.1 (MH⁺) |
| 109 | 4-(methoxycarbonyl)phenyl-X₁ | 437.1 (MH⁺) |

TABLE 3-continued

| Compound No. | R¹ | MS |
|---|---|---|
| 110 | 2,4-dimethylphenyl-X₁ | 407.1 (MH⁺) |
| 111 | 4-methoxynaphthyl-X₁ | 459.1 (MH⁺) |
| 112 | PhCH(CH₃)CH₂-X₁ | 421.1 (MH⁺) |
| 113 | 2,6-dichlorobenzyloxyphenyl-X₁ | 553.1 (M⁺) |
| 114 | 3-(benzyloxy)phenyl-X₁ | 485.1 (MH⁺) |
| 115 | 4-((2-chloro-6-fluorobenzyl)oxy)phenyl-X₁ | 537.1 (M⁺) |
| 116 | 4-bromo-2-hydroxyphenyl-X₁ | 473.1 (M⁺) |
| 117 | 5-(2-nitrophenyl)furan-2-yl-X₁ | 490.1 (MH⁺) |
| 118 | 2-(2-hydroxyethoxy)phenyl-X₁ | 439.1 (MH⁺) |
| 119 | cyclohexyl-X₁ | 485.1 (MH⁺) |
| 120 | 4-(2-hydroxyethoxy)phenyl-X₁ | 439.1 (MH⁺) |
| 121 | 4-bromo-2-methoxyphenyl-X₁ | 488.1 (MH⁺) |
| 122 | 2,5-difluorophenyl-X₁ | 415.1 (MH⁺) |
| 123 | 2,3-dihydrobenzo[1,4]dioxin-6-yl-X₁ | 437.1 (MH⁺) |
| 124 | 9H-fluoren-2-yl-X₁ | 467.1 (MH⁺) |
| 125 | biphenyl-4-yl-X₁ | 455.1 (MH⁺) |
| 126 | 4-methoxy-3-methylphenyl-X₁ | 423.1 (MH⁺) |

TABLE 3-continued

| Compound No. | R¹ | MS |
| --- | --- | --- |
| 127 | 3,4-difluorophenyl-X₁ | 415.1 (MH⁺) |
| 128 | 4-(methylthio)phenyl-X₁ | 425.1 (MH⁺) |
| 129 | 6-methoxynaphthalen-2-yl-X₁ | 459.1 (MH⁺) |
| 130 | 4-methoxy-2,3-dimethylphenyl-X₁ | 437.1 (MH⁺) |
| 131 | 2-(methoxycarbonylmethoxy)phenyl-X₁ | 467.1 (MH⁺) |
| 132 | 2-fluorophenyl-X₁ | 397.1 (MH⁺) |
| 133 | 2-(trifluoromethyl)phenyl-X₁ | 447.1 (MH⁺) |
| 134 | 3-(trifluoromethyl)phenyl-X₁ | 447.1 (MH⁺) |
| 135 | 3-fluorophenyl-X₁ | 397.1 (MH⁺) |
| 136 | 4-ethylphenyl-X₁ | 407.1 (MH⁺) |
| 137 | thiophen-3-yl-X₁ | 385.1 (MH⁺) |
| 138 | furan-3-yl-X₁ | 369.1 (MH⁺) |
| 139 | 3,4-bis(benzyloxy)phenyl-X₁ | 591.1 (MH⁺) |
| 140 | bicyclo[2.2.1]hept-2-en-5-yl-X₁ | 395.1 (MH⁺) |
| 141 | 4-nitrophenyl-X₁ | 424.1 (MH⁺) |
| 142 | 4-butoxyphenyl-X₁ | 451.1 (MH⁺) |
| 143 | 2,5-dimethylphenyl-X₁ | 407.1 (MH⁺) |
| 144 | 3-methoxyphenyl-X₁ | 409.1 (MH⁺) |

TABLE 3-continued

| Compound No. | R¹ | MS |
|---|---|---|
| 145 | 3-(2-hydroxyethoxy)phenyl-X₁ | 439.1 (MH⁺) |
| 146 | 3-methylphenyl-X₁ | 393.1 (MH⁺) |
| 147 | naphthalen-1-yl-X₁ | 429.1 (MH⁺) |
| 148 | 4-phenoxyphenyl-X₁ | 471.1 (MH⁺) |
| 149 | 3-(4-chlorophenoxy)phenyl-X₁ | 505.1 (MH⁺) |
| 150 | 3-(4-tert-butylphenoxy)phenyl-X₁ | 527.1 (MH⁺) |
| 151 | 5-nitrofuran-2-yl-X₁ | 414.1 (MH⁺) |
| 152 | 2,4-dimethoxy-3-methylphenyl-X₁ | 453.1 (MH⁺) |
| 153 | 2-chloroquinolin-3-yl-X₁ | 464.1 (M⁺) |
| 154 | 5-nitrothiophen-3-yl-X₁ | 430.1 (MH⁺) |
| 155 | 9-ethylcarbazol-3-yl-X₁ | 496.1 (MH⁺) |
| 156 | 3-[3-(trifluoromethyl)phenoxy]phenyl-X₁ | 539.1 (MH⁺) |

TABLE 3-continued
| Compound No. | R¹ | MS |
|---|---|---|
| 157 | 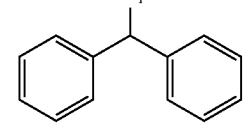 | 485.1 (MH⁺) |
| 159 | 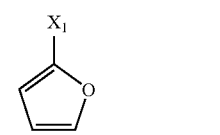 | 395.1 (MH⁺) |
| 160 | 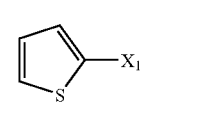 | 413.1 (MH⁺) |
| 161 | 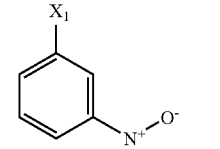 | 395.1 (MH⁺) |
| 162 | 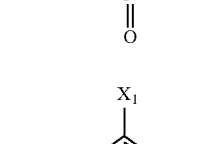 | 435.1 (MH⁺) |
| 163 | 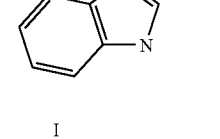 | 469.1 (MH⁺) |
| 164 |  | 369.1 (MH⁺) |
| 165 |  | 385.1 (MH⁺) |
| 166 |  | 424.1 (MH⁺) |
| 167 |  | 418.1 (MH⁺) |
| 168 |  | 505 (MH⁺) |
Thus, compounds in Table 3 have the formulas given in Table 4 below.
TABLE 4
| Compound No. | Structure |
|---|---|
| 89 | 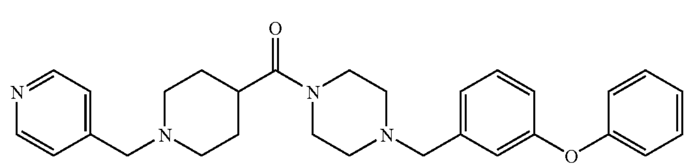 |

TABLE 4-continued
| Compound No. | Structure |
|---|---|
| 90 | 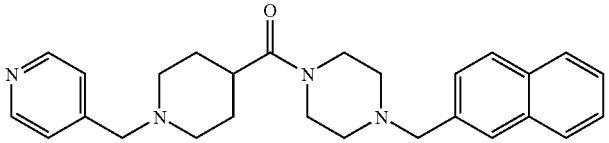 |
| 91 | 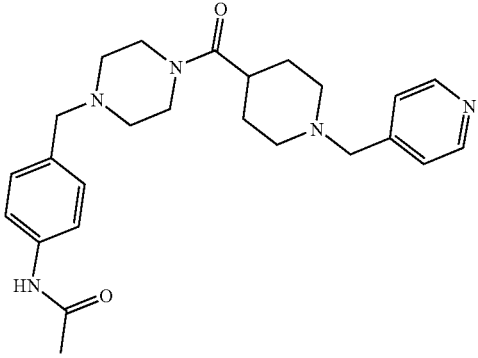 |
| 92 | 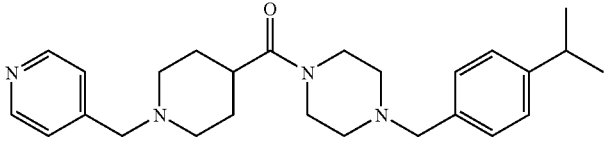 |
| 93 | 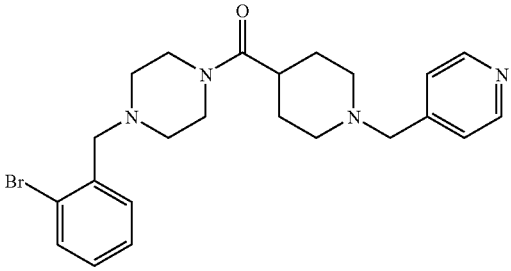 |
| 94 | 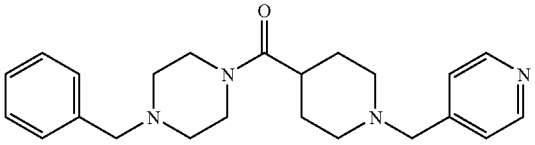 |
| 95 | 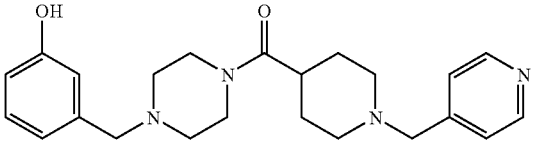 |
| 96 | 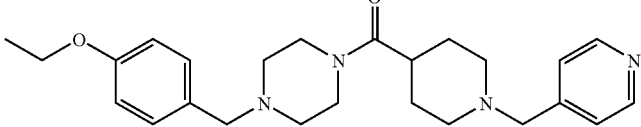 |

TABLE 4-continued
| Compound No. | Structure |
|---|---|
| 97 | 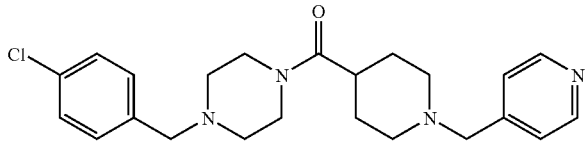 |
| 98 | 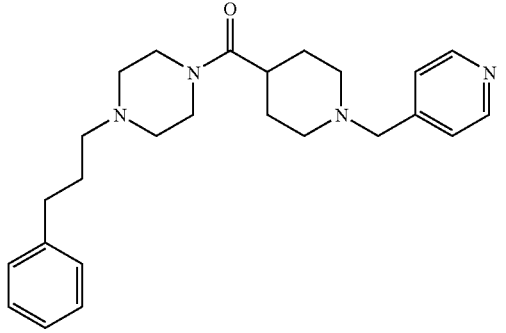 |
| 99 | 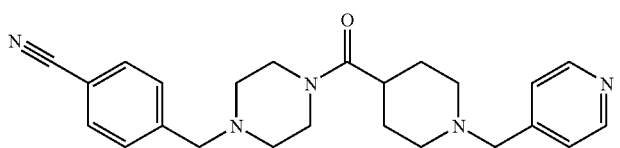 |
| 100 | 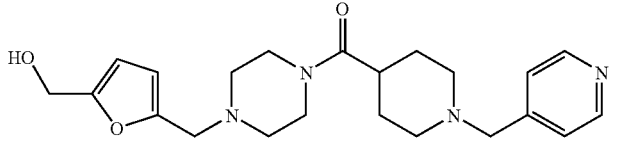 |
| 101 | 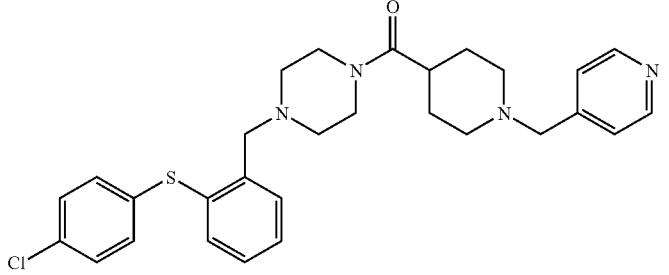 |
| 102 | 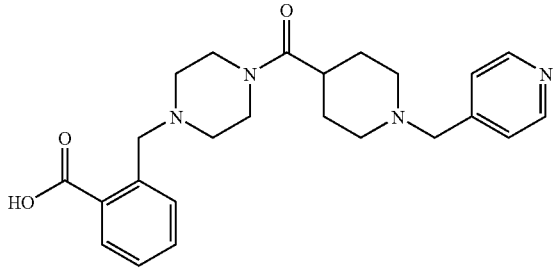 |
| 103 | 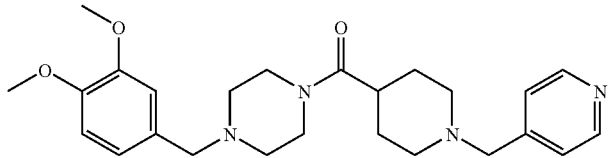 |

TABLE 4-continued
| Compound No. | Structure |
|---|---|
| 104 | 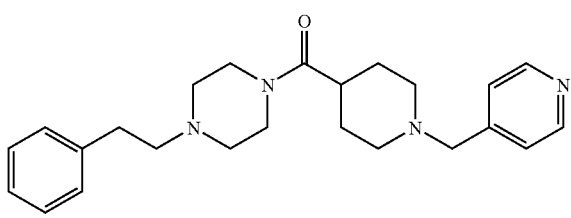 |
| 105 | 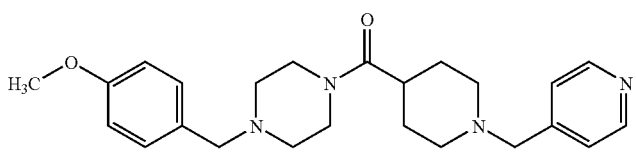 |
| 106 | 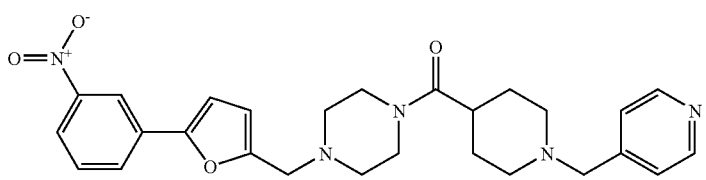 |
| 107 | 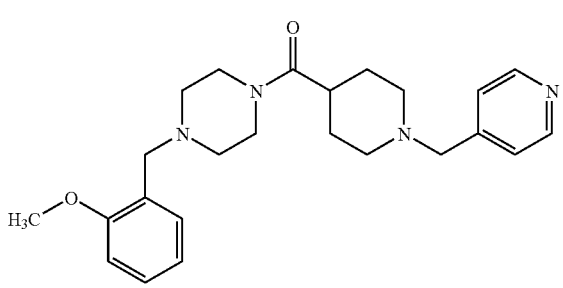 |
| 108 | 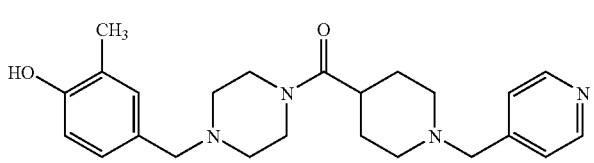 |
| 109 | 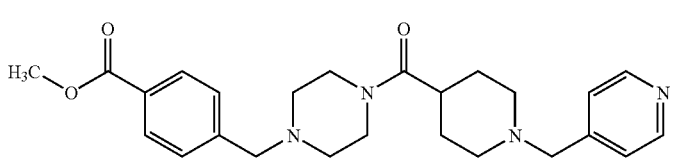 |
| 110 | 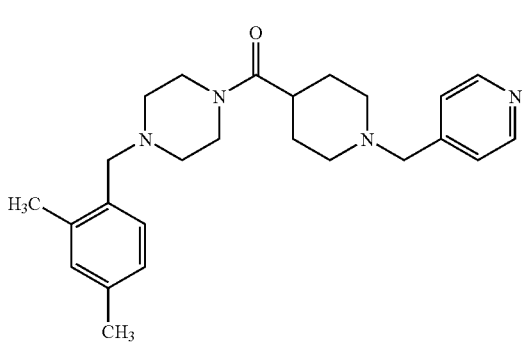 |

TABLE 4-continued
| Compound No. | Structure |
|---|---|
| 111 | 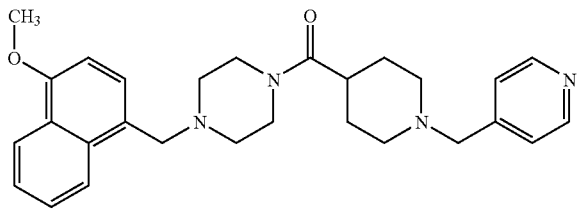 |
| 112 | 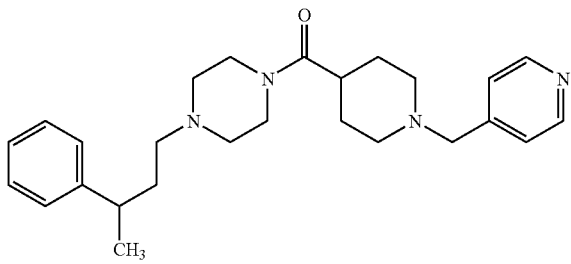 |
| 113 | 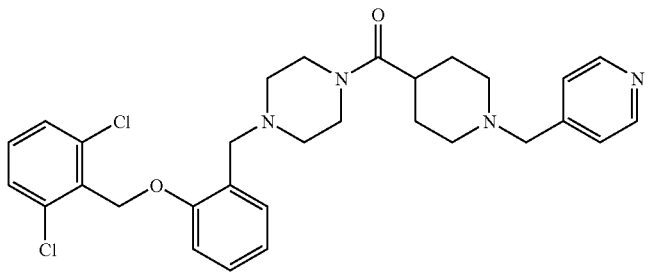 |
| 114 | 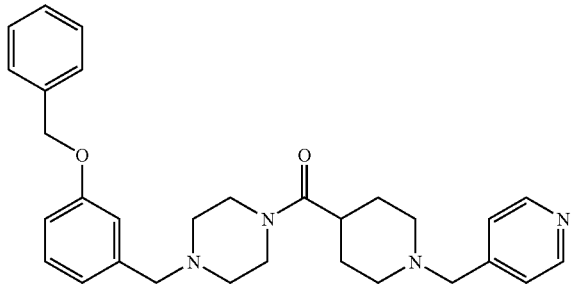 |
| 115 | 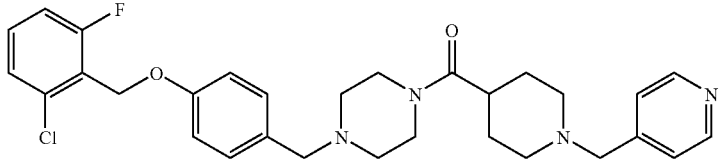 |
| 116 | 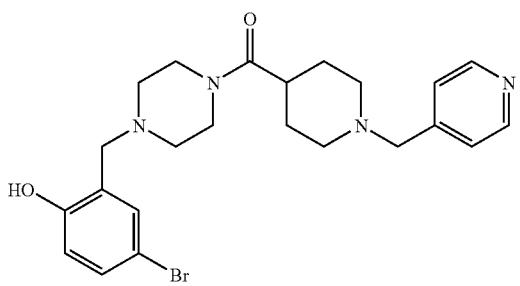 |

TABLE 4-continued

| Compound No. | Structure |
|---|---|
| 117 | 2-nitrophenyl-furan-CH2-piperazine-C(O)-piperidine-CH2-(4-pyridyl) |
| 118 | 2-(2-hydroxyethoxy)phenyl-CH2-piperazine-C(O)-piperidine-CH2-(4-pyridyl) |
| 119 | cyclohexyl-CH2-piperazine-C(O)-piperidine-CH2-(4-pyridyl) |
| 120 | 4-(2-hydroxyethoxy)phenyl-CH2-piperazine-C(O)-piperidine-CH2-(4-pyridyl) |
| 121 | 5-bromo-2-methoxyphenyl-CH2-piperazine-C(O)-piperidine-CH2-(4-pyridyl) |
| 122 | 2,5-difluorophenyl-CH2-piperazine-C(O)-piperidine-CH2-(4-pyridyl) |

TABLE 4-continued
| Compound No. | Structure |
|---|---|
| 123 | 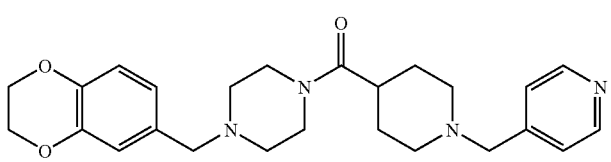 |
| 124 | 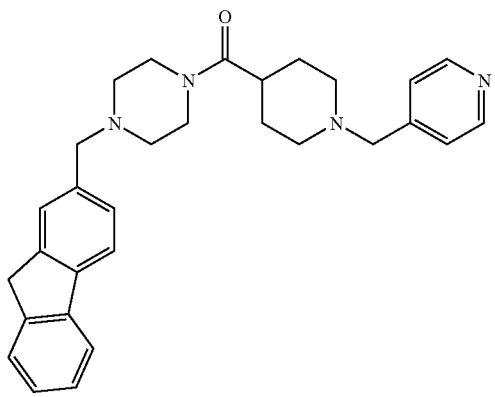 |
| 125 | 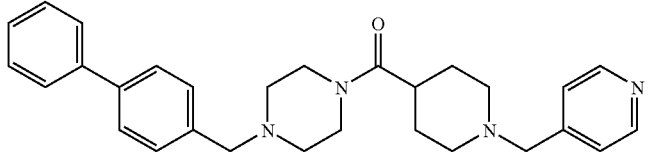 |
| 126 | 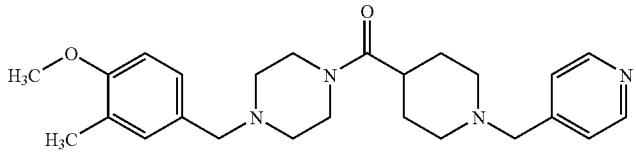 |
| 127 | 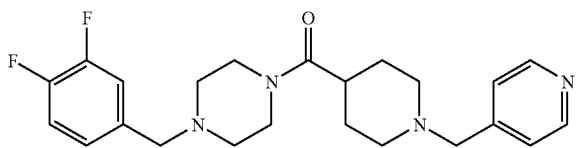 |
| 128 | 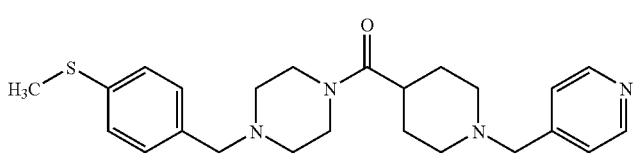 |

TABLE 4-continued

| Compound No. | Structure |
|---|---|
| 129 | 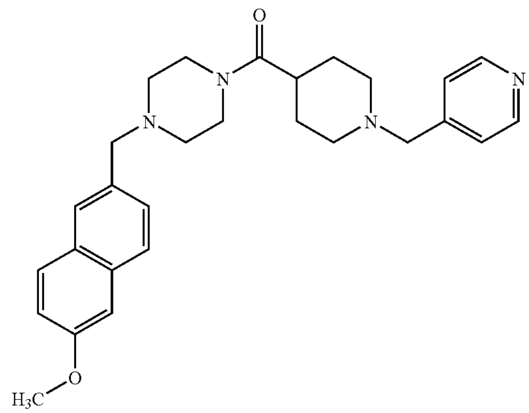 |
| 130 | 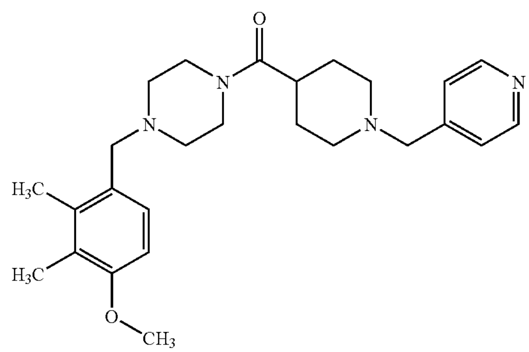 |
| 131 | 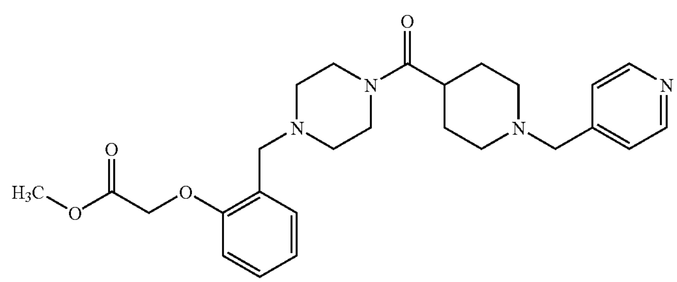 |
| 132 | 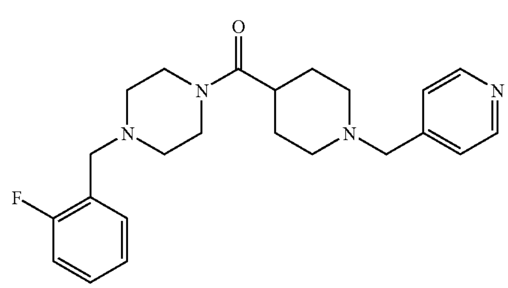 |

TABLE 4-continued
| Compound No. | Structure |
|---|---|
| 133 | 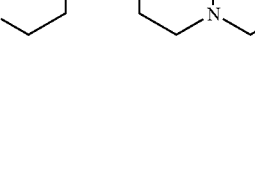 |
| 134 | 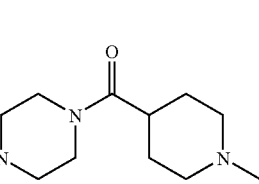 |
| 135 | 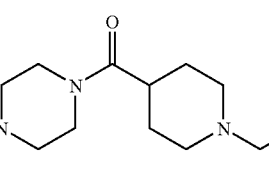 |
| 136 | 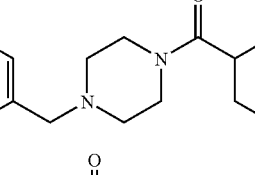 |
| 137 | 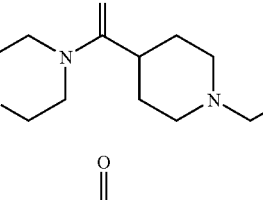 |
| 138 | 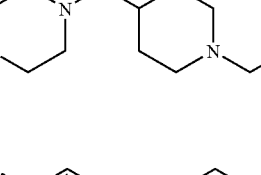 |
| 139 | 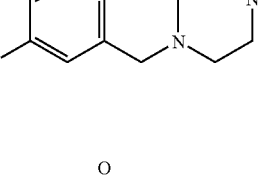 |
| 140 | 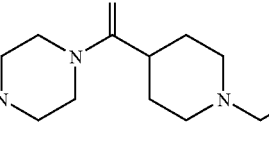 |

TABLE 4-continued
| Compound No. | Structure |
|---|---|
| 141 | 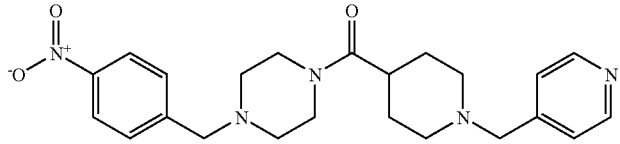 |
| 142 | 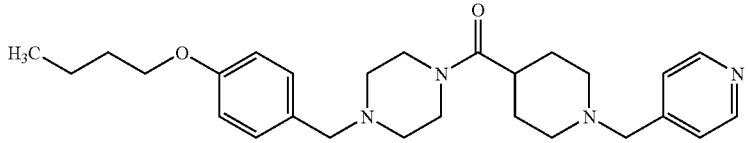 |
| 143 | 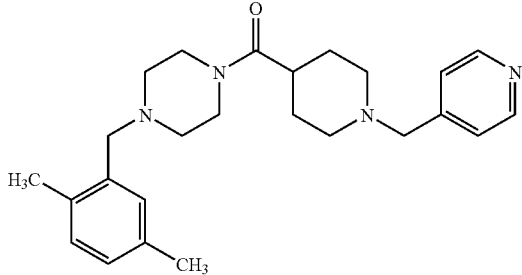 |
| 142 | 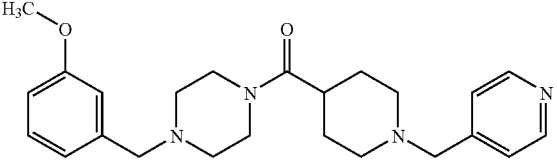 |
| 145 | 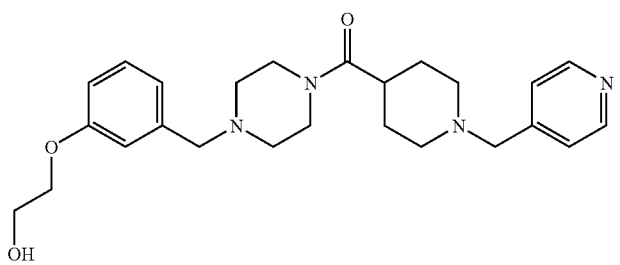 |
| 146 | 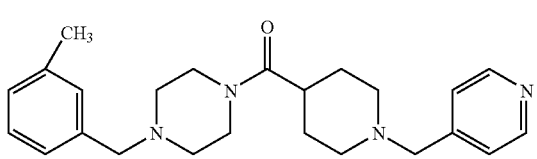 |

TABLE 4-continued

| Compound No. | Structure |
|---|---|
| 147 | 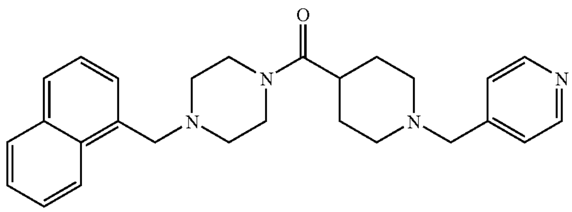 |
| 148 | 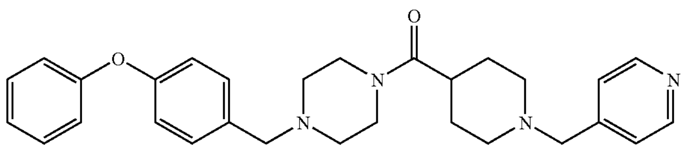 |
| 149 | 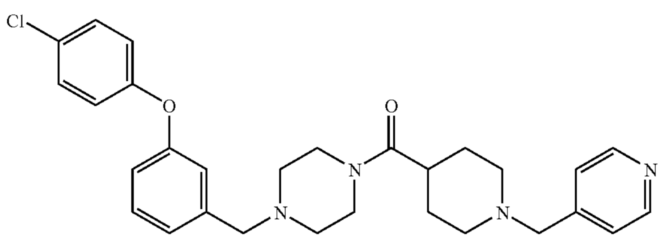 |
| 150 | 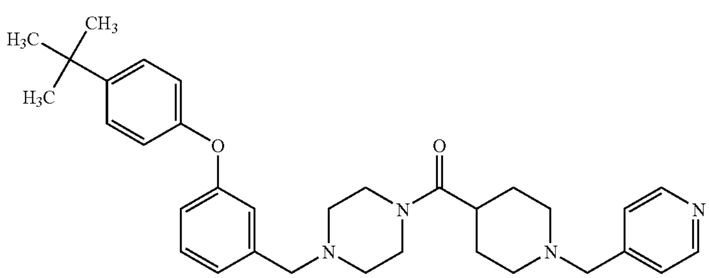 |
| 151 | 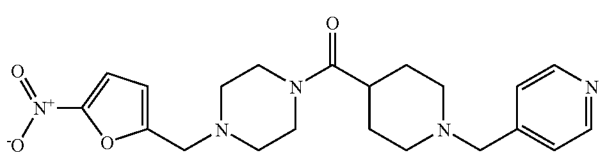 |
| 152 | 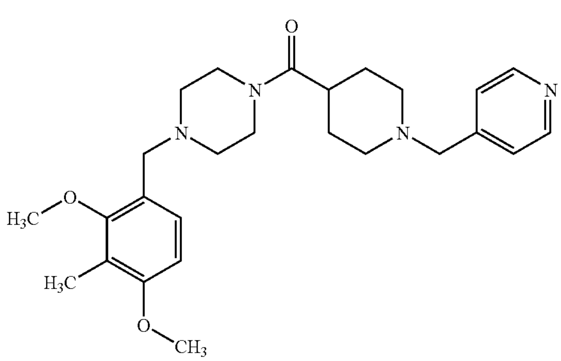 |

TABLE 4-continued

| Compound No. | Structure |
|---|---|
| 153 | 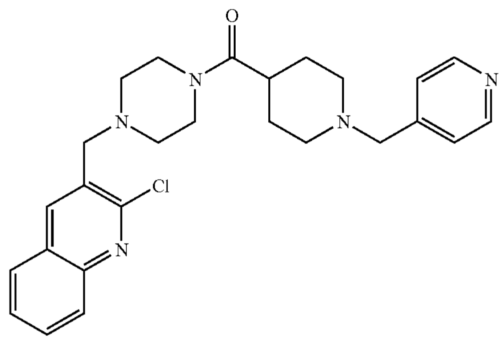 |
| 154 | 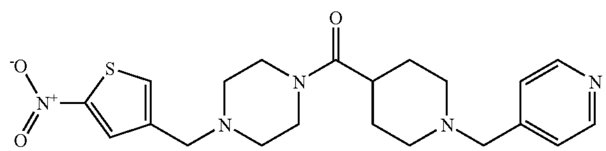 |
| 155 | 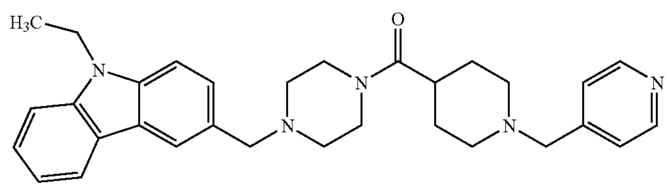 |
| 156 | 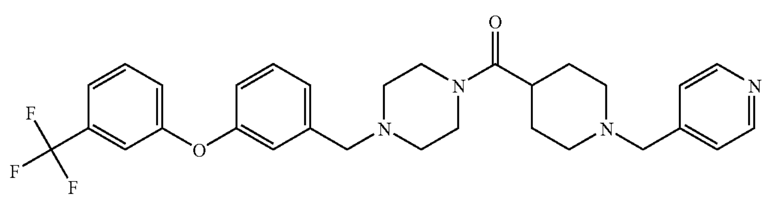 |
| 157 | 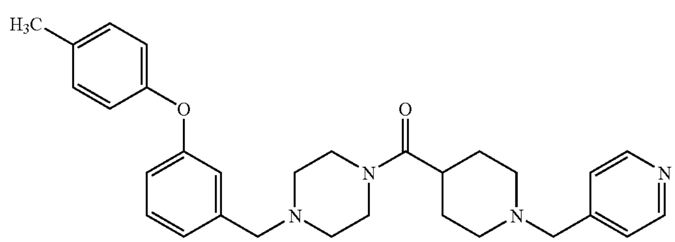 |
| 159 | 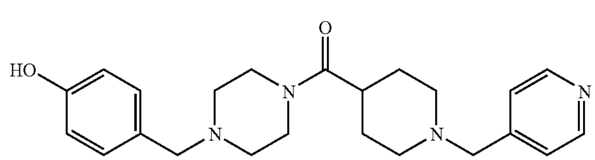 |

TABLE 4-continued

| Compound No. | Structure |
|---|---|
| 160 | 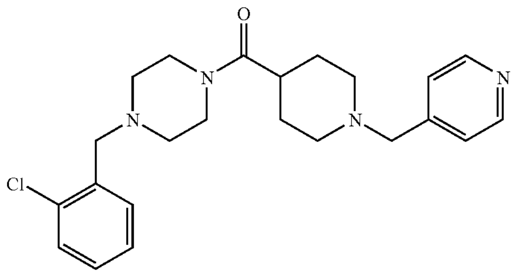 |
| 161 | 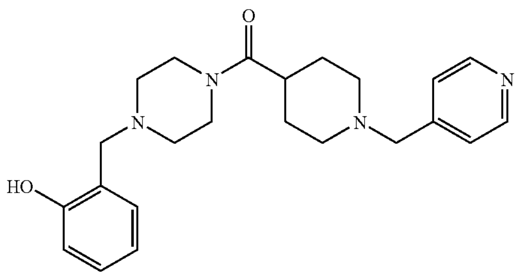 |
| 162 | 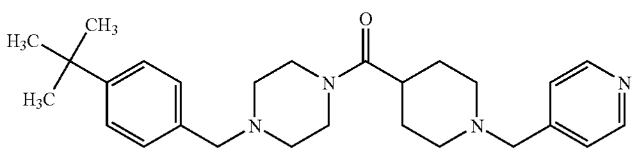 |
| 163 | 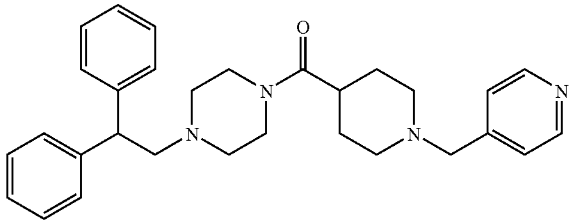 |
| 164 | 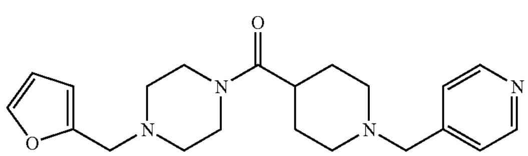 |
| 165 | 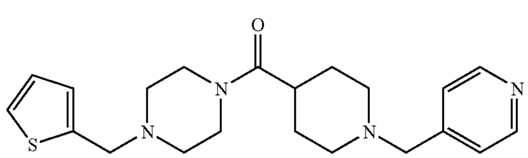 |
| 166 | 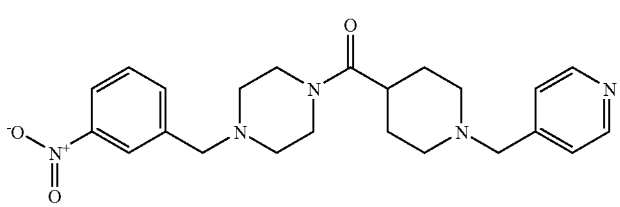 |

TABLE 4-continued

| Compound No. | Structure |
|---|---|
| 167 | 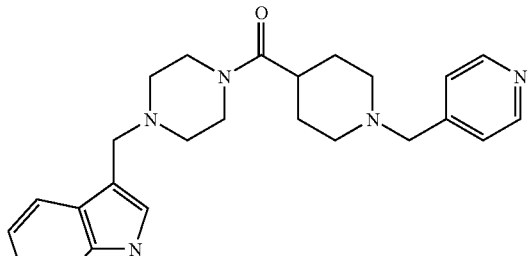 |
| 168 | 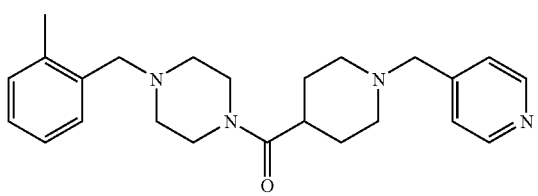 |

EXAMPLE 18

Library Preparation on Solid Phase

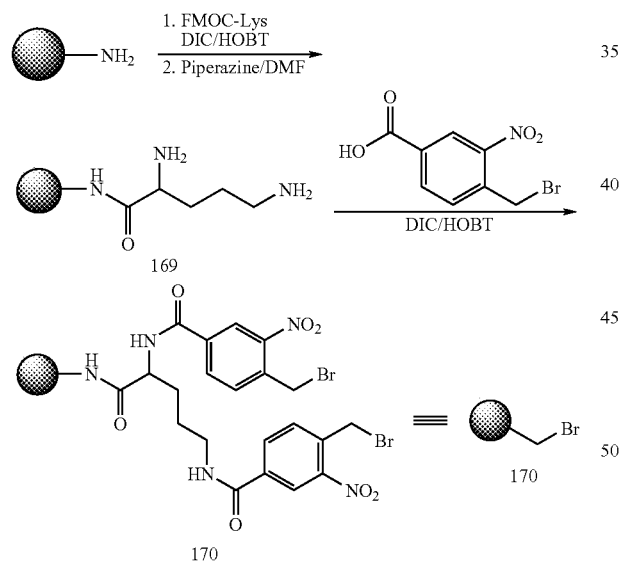

TentaGel amino resin (1 eq.) was placed in a reaction vessel, dichloromethane, FMOC-Lysine (2 eq.) and HOBT (2.2 eq.) were added followed by the addition of DIC (2eq.). The mixture was shaken at room temperature for 12 hours, then drained and the resin was washed with dichloromethane twice and DMF three times, and treated with 20% piperazine in DMF (v/v) for 30 minutes. The resin was then washed with DMF twice, methanol twice and dichloromethane three times, and dried overnight in vacuo to give amine resin 169.

The amine resin 169 (1 eq.) was placed in a reaction vessel, dichloromethane, 4-bromomethyl-3-nitrobenzoic acid (2 eq.) and HOBT (2.2 eq.) were added followed by the addition of DIC (2eq.). The mixture was shaken at room temperature for 12 hours, then drained and the resin was washed with dichloromethane twice, methanol twice and dichloromethane three times, and dried overnight in vacuo to give bromoresin 170.

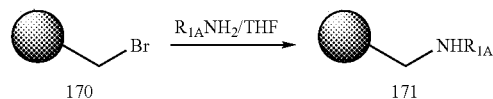

The bromo resin 170 was divided into 24 portions, and each (1eq.) was treated with an amine (see 172 to 196 below) (5eq.) in THF. The mixture was shaken at room temperature overnight, drained and the resin was washed with THF twice, DMF twice and dichloromethane three times, and dried overnight in vacuo to give amine resin 171.

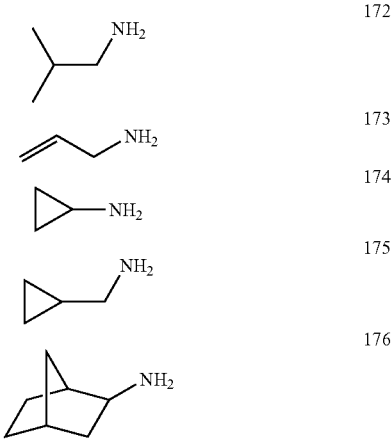

-continued

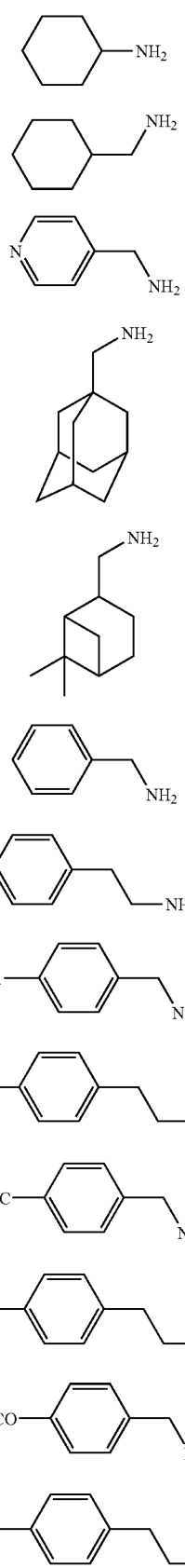

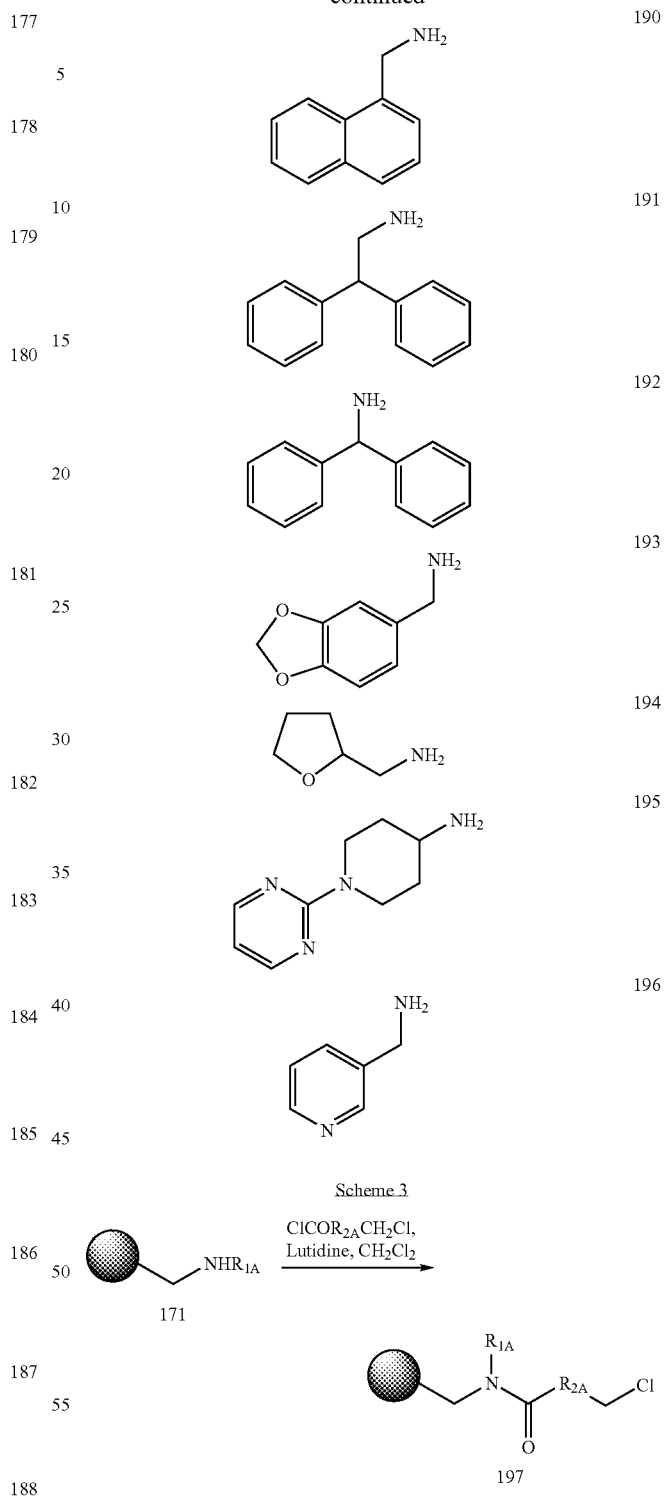

The amine resin 171 was divided into 3 portions, and each (1 eq.) was treated with an acid chloride (see 198 to 200 below)(2 eq.) and 2,6-lutidine (4 eq.) in dichloromethane. The mixture was shaken at room temperature for 30 minutes, drained and the resin was washed with dichloromethane twice, methanol twice and dichloromethane three times, and dried overnight in vacuo to give chlororesin 197.

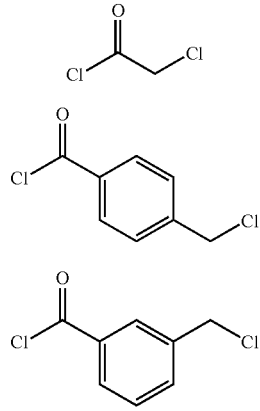

198

199

200

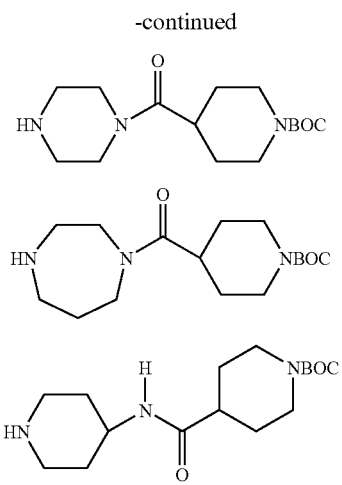

-continued

206

207

208

Scheme 4

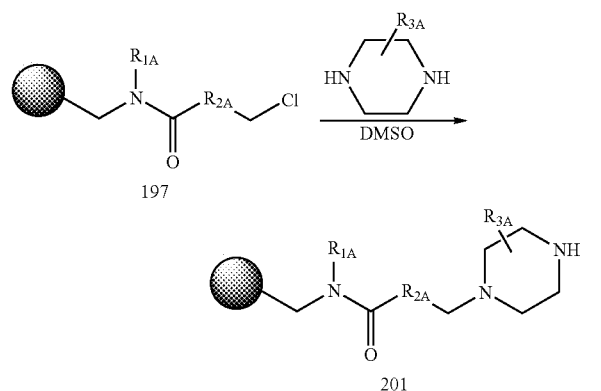

Scheme 5

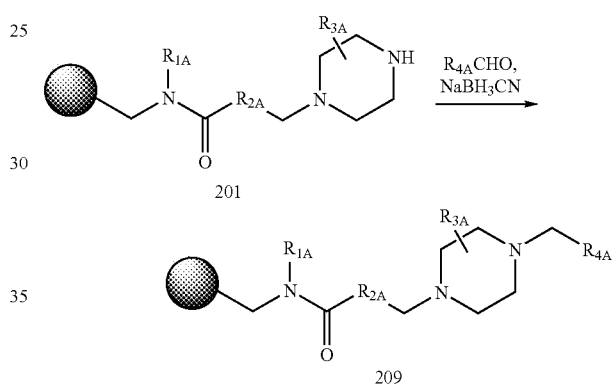

The chlororesin 197 was divided into 7 portions, and each (1 eq.) was treated with an appropriate amine (see 202 to 208 below) (5 eq.) in DMSO. The mixture was shaken at room temperature overnight, drained and the resin was washed with methanol twice, dichloromethane twice, methanol twice and dichloromethane three times, and dried in vacuo to give amine resin 201.

The amine resin 201 was divided into 2 reaction vessels, and each was treated with 2% HOAc in DMF and an appropriate aldehyde (see 210–211 below). The mixture was shaken at room temperature for 30 minutes, and NaBH$_3$CN was added to each reaction vessel. The mixture was shaken for overnight, drained, and the resin was washed with DMF twice, methanol three times and 10% HCl in methanol, and dried in vacuo to give resin 209.

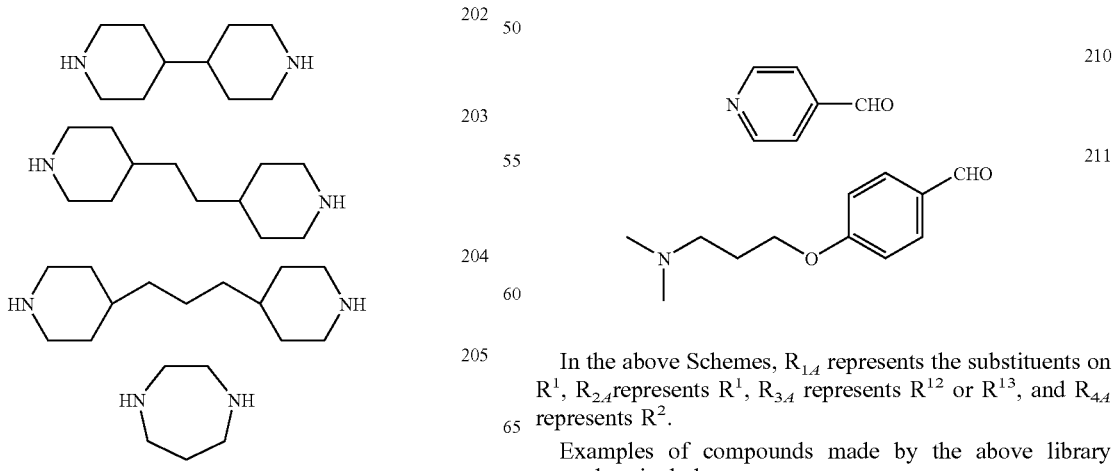

202

203

204

205

210

211

In the above Schemes, $R_{1A}$ represents the substituents on $R^1$, $R_{2A}$ represents $R^1$, $R_{3A}$ represents $R^{12}$ or $R^{13}$, and $R_{4A}$ represents $R^2$.

Examples of compounds made by the above library procedure include:

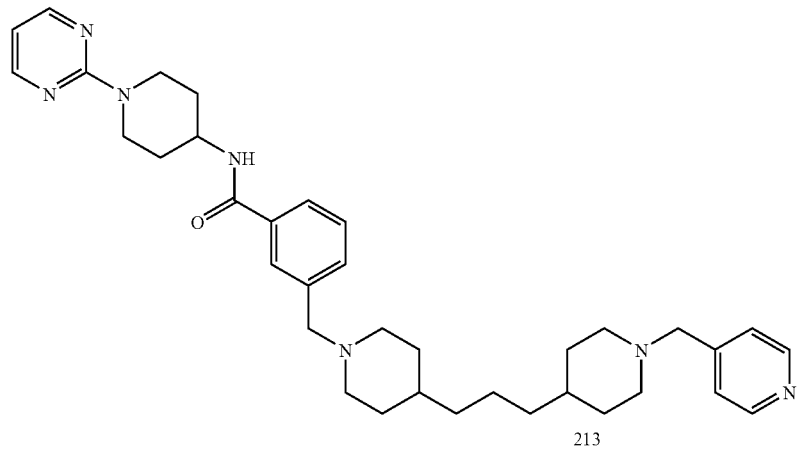
212
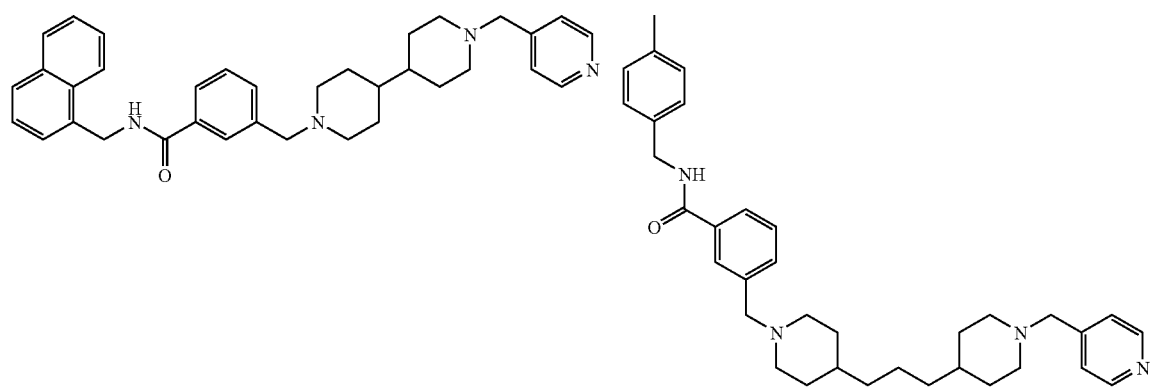
213
214
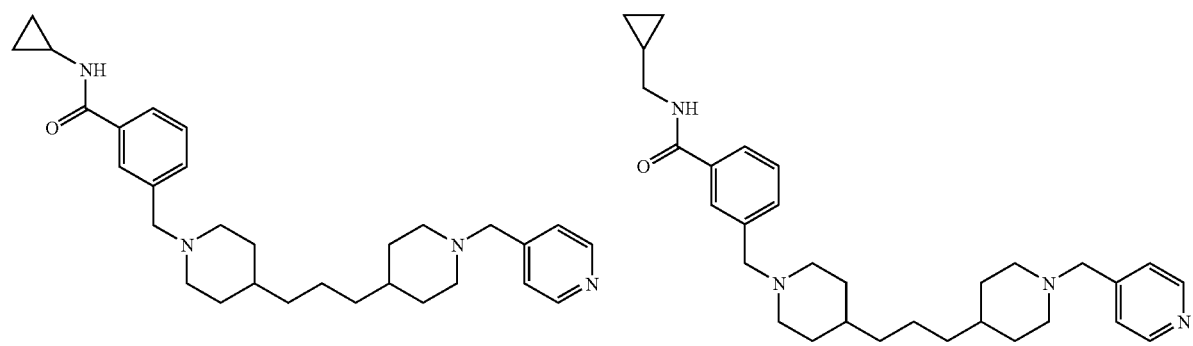
215
216
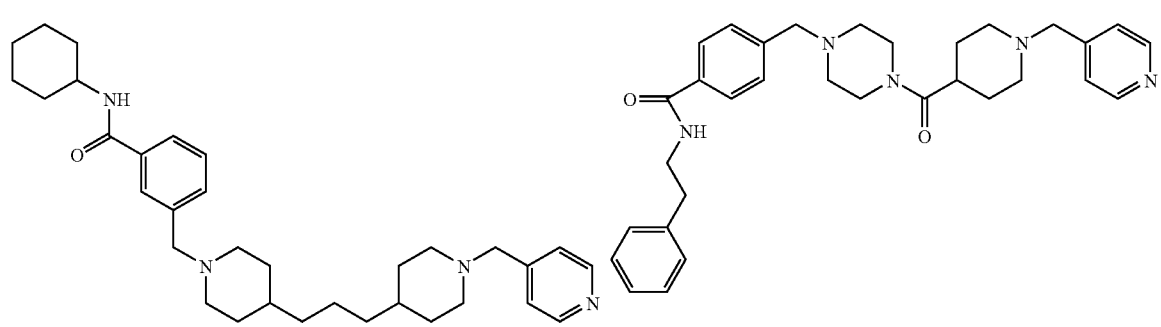
217

-continued
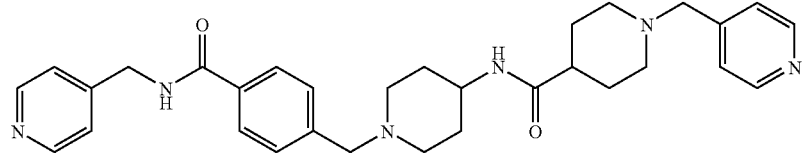
219
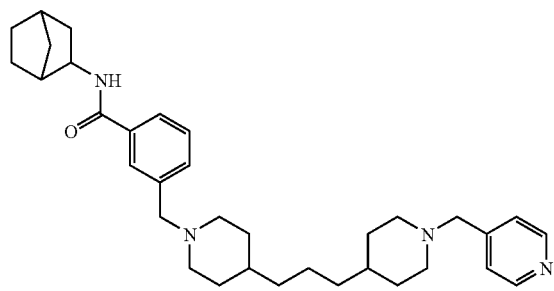
220
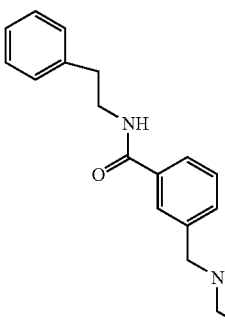
221
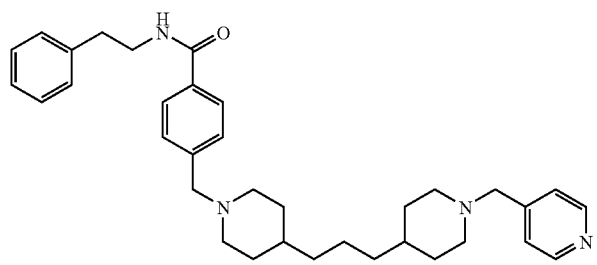
222
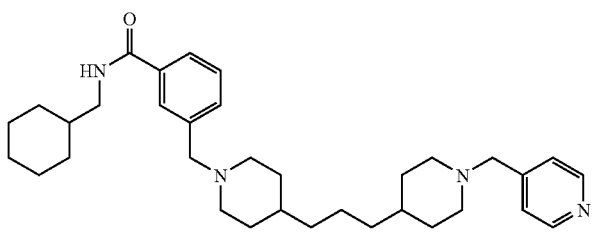
223
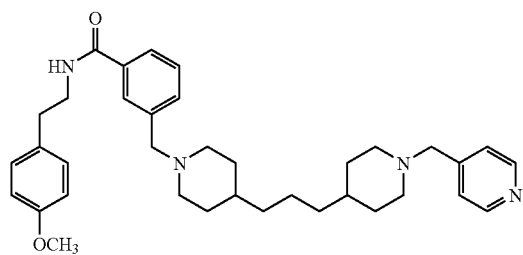
224
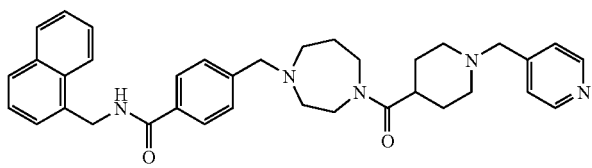
225
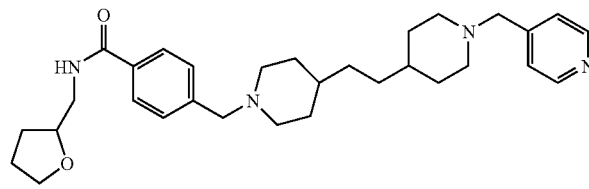
226
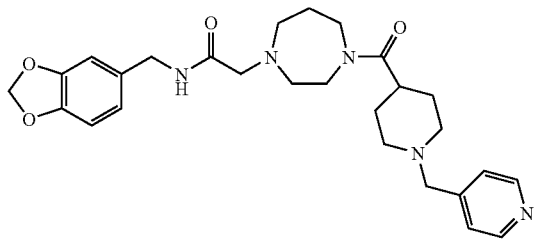
227

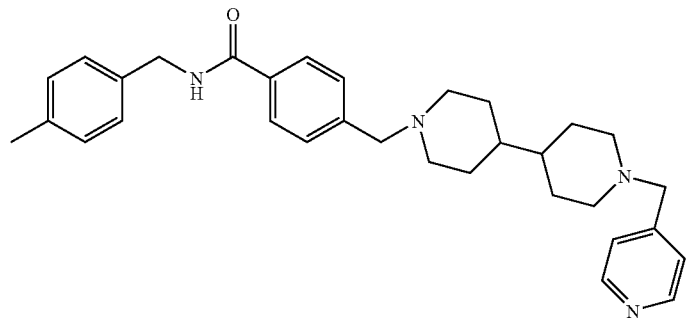
228
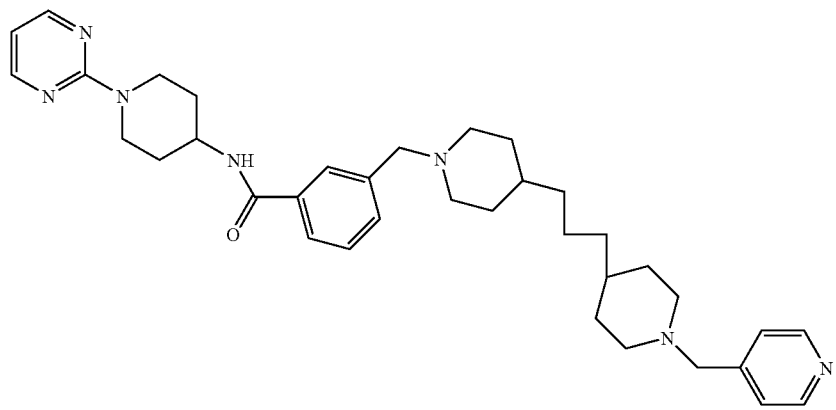
229
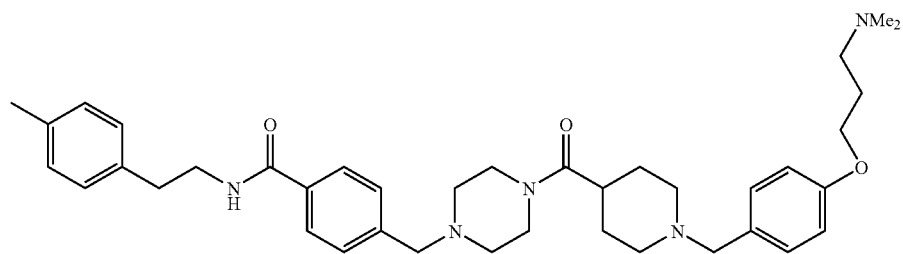
230
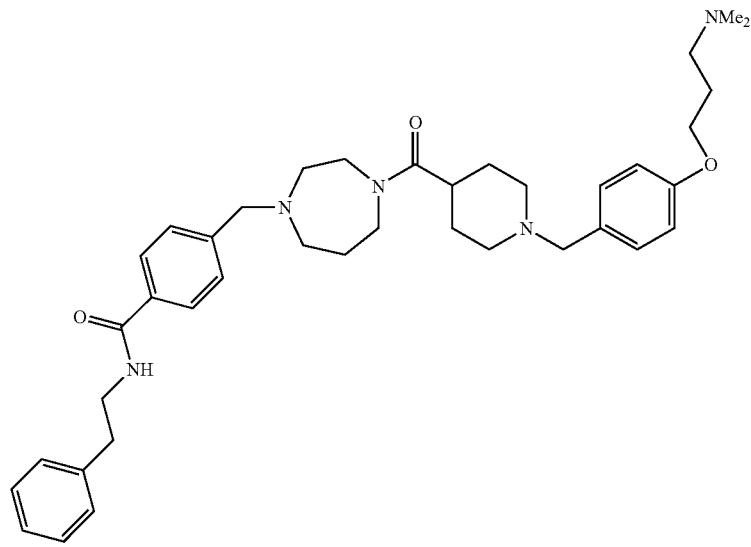
231

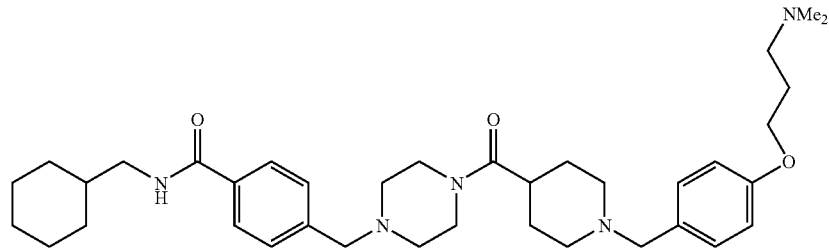
232
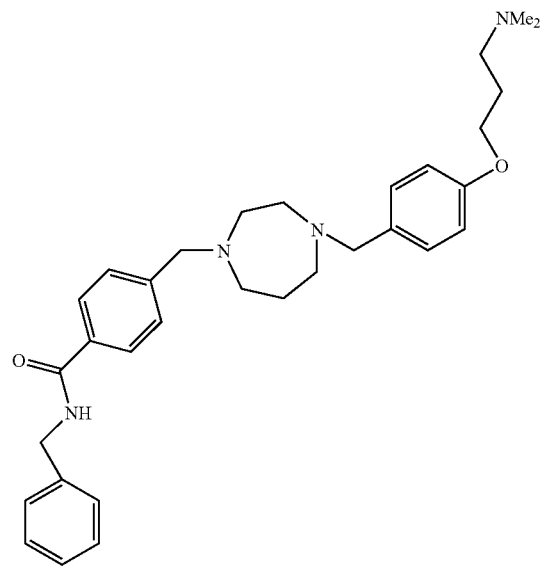
233
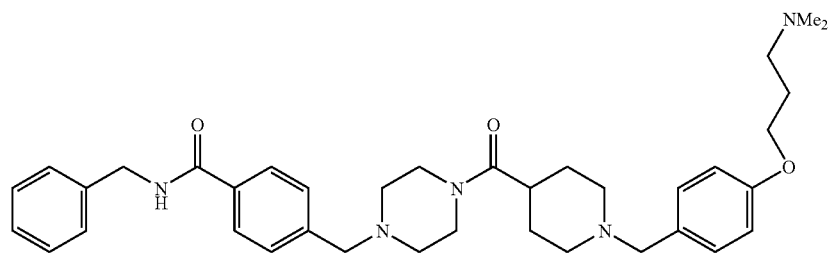
234
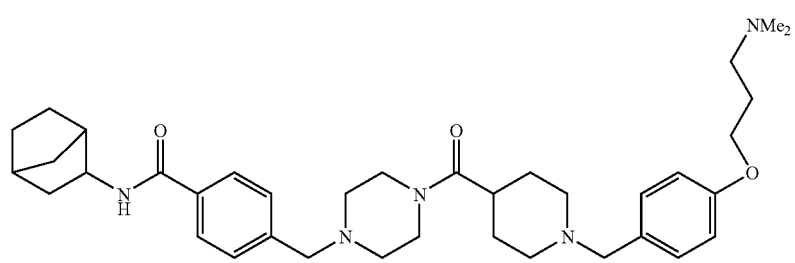
235

-continued
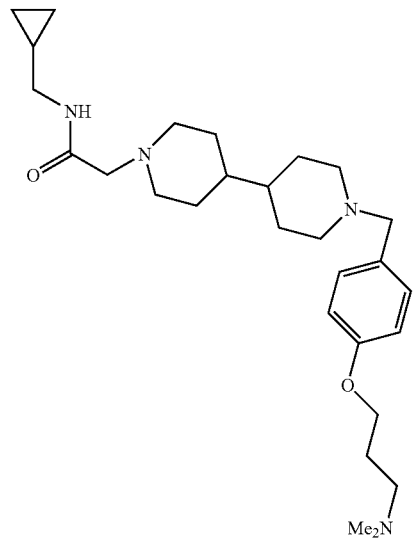
236
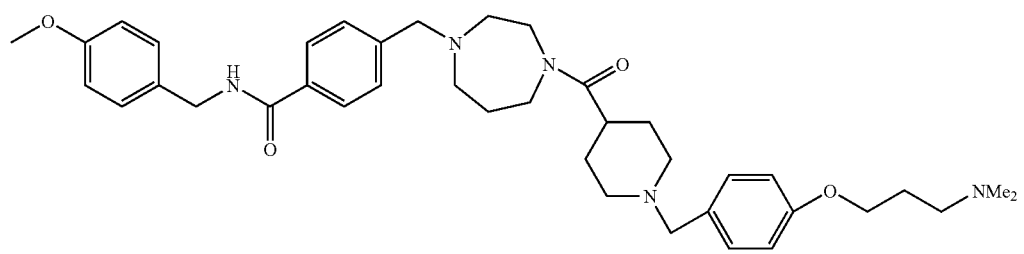
237
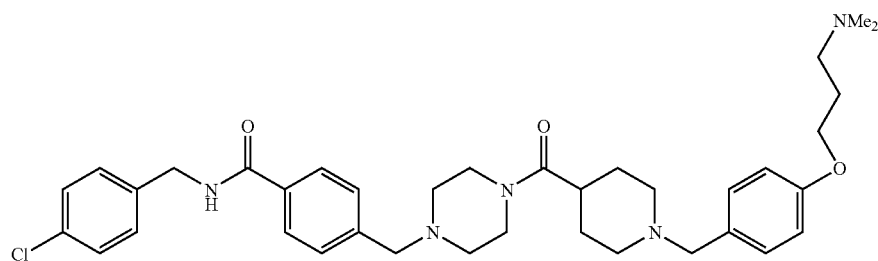
238
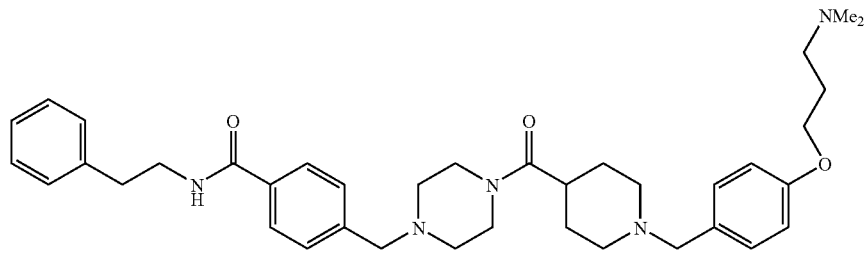
239
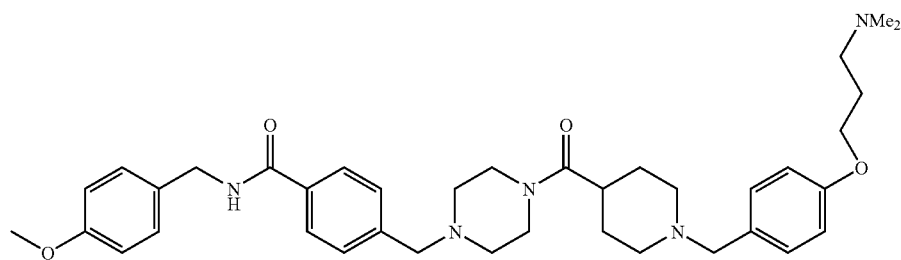
240

-continued
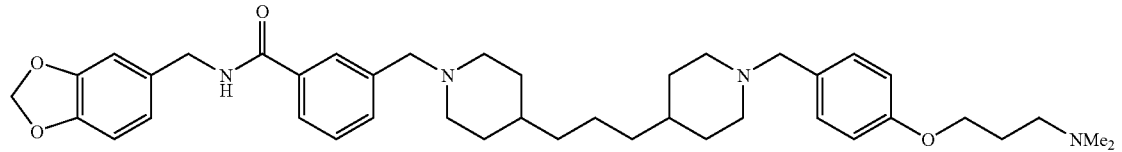
241
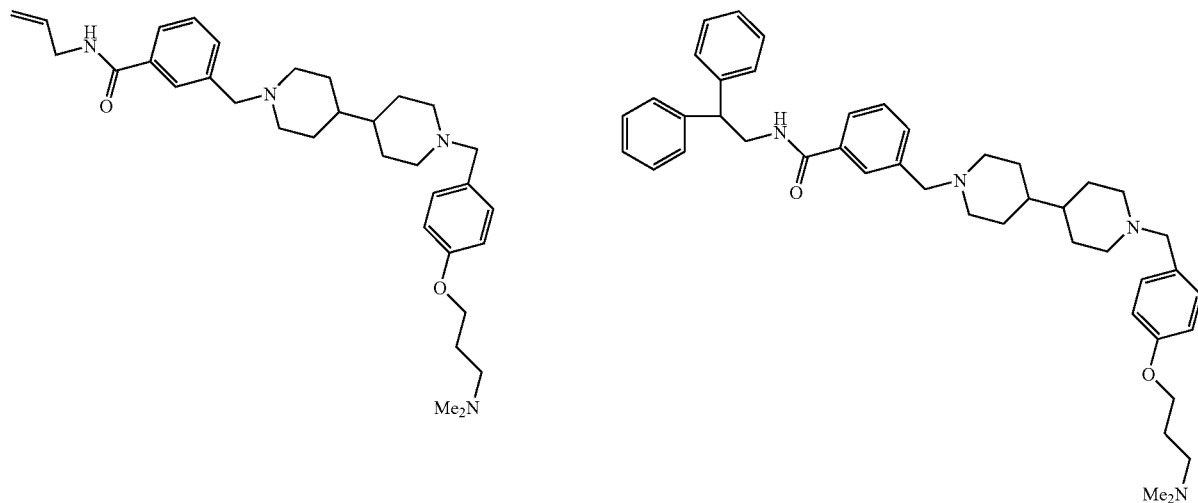
242
243
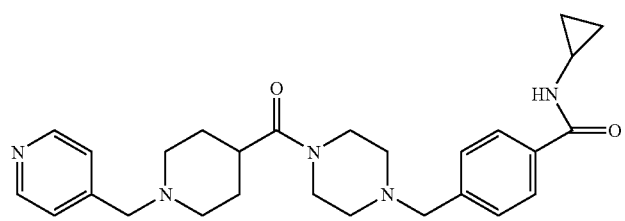
244
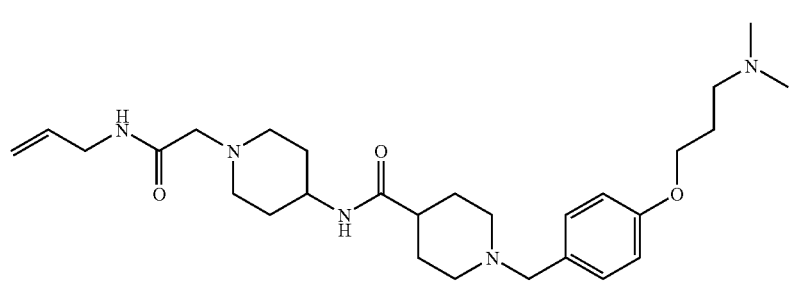
245
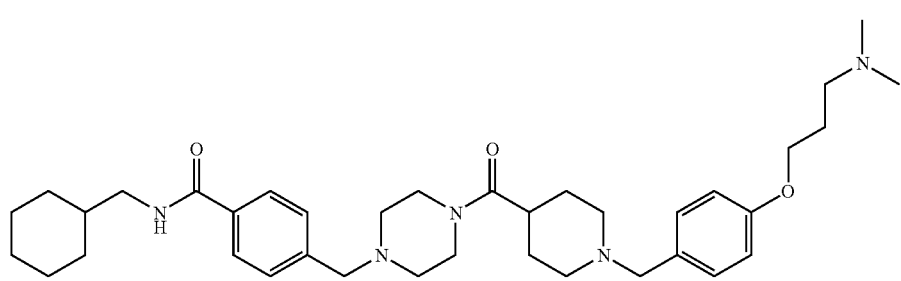
246

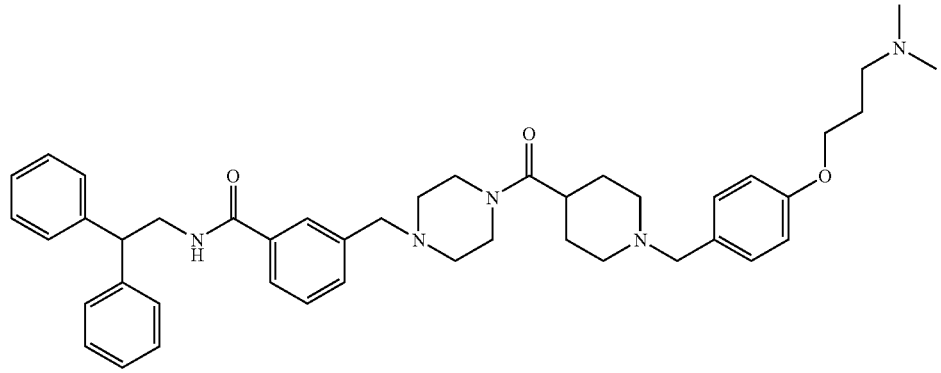
247
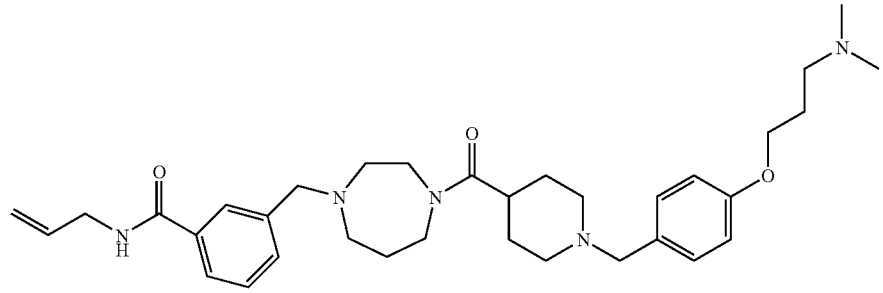
248
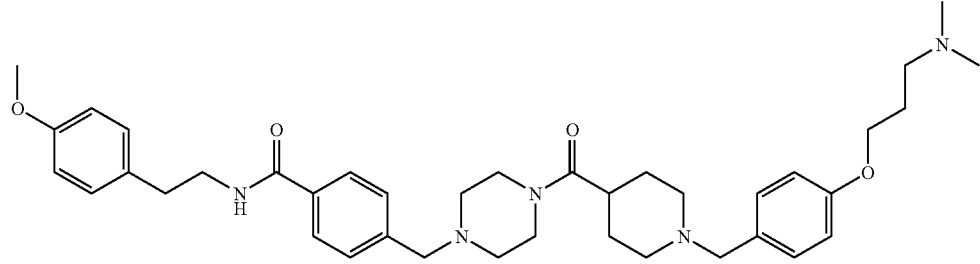
249
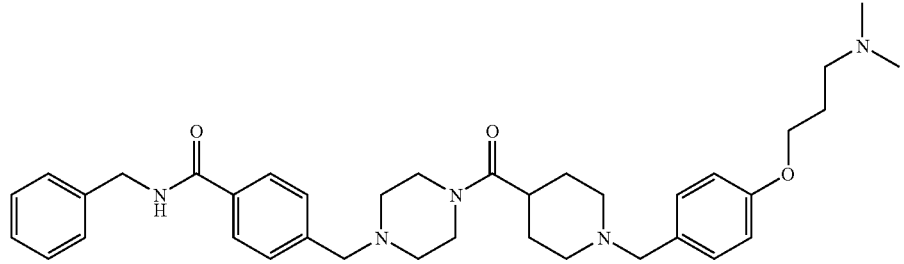
250
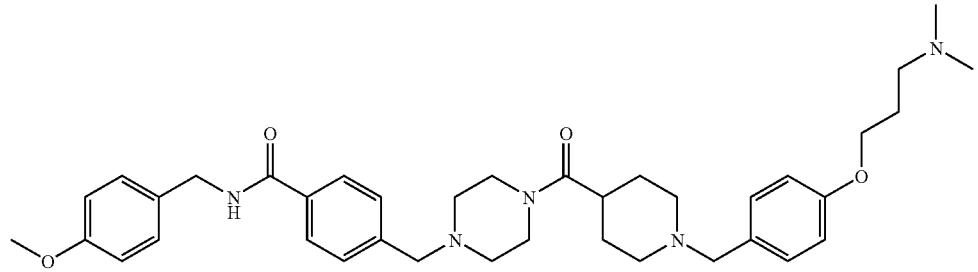
251

-continued
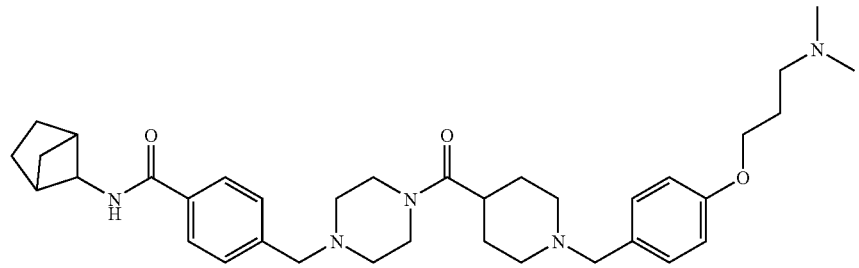
253
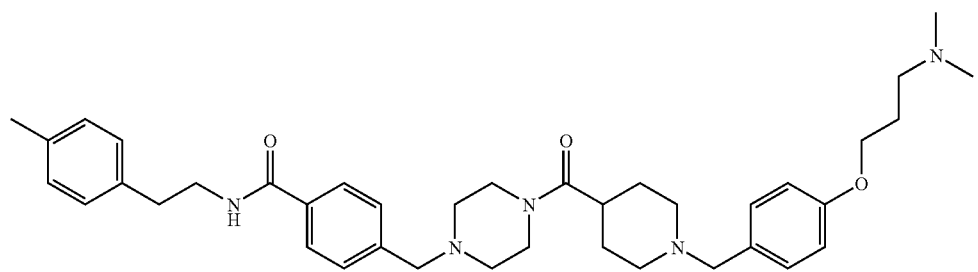
254
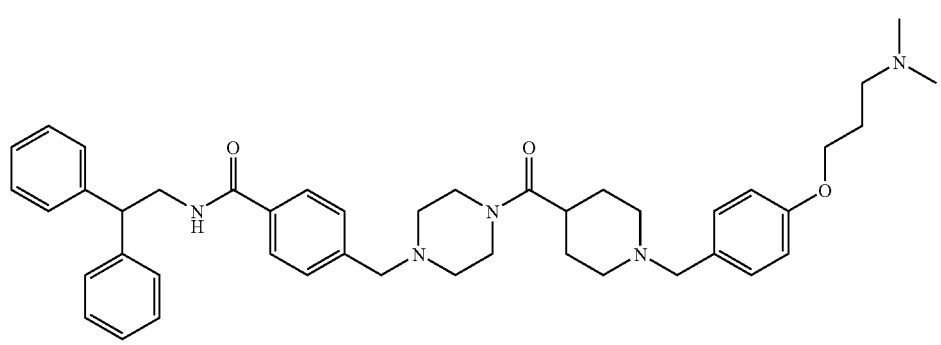
255
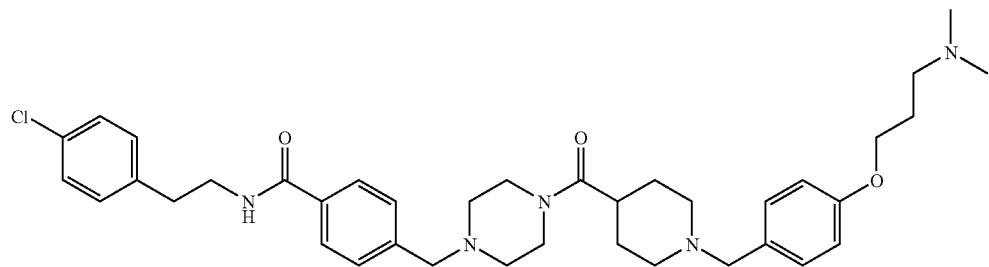
256
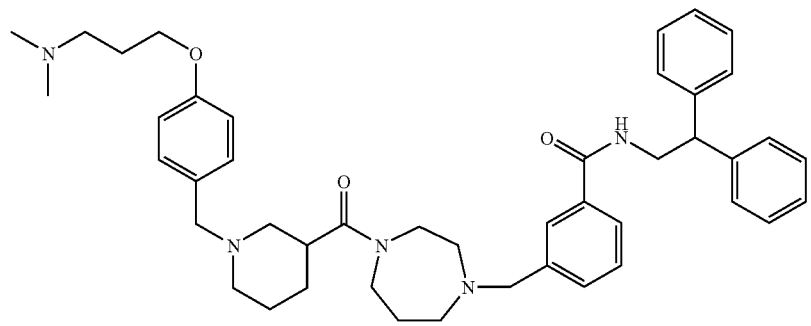

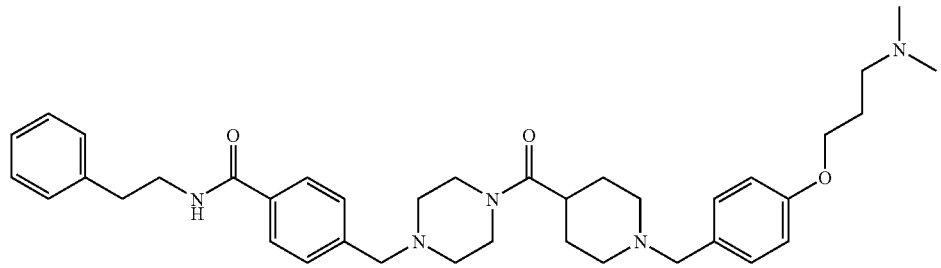
257
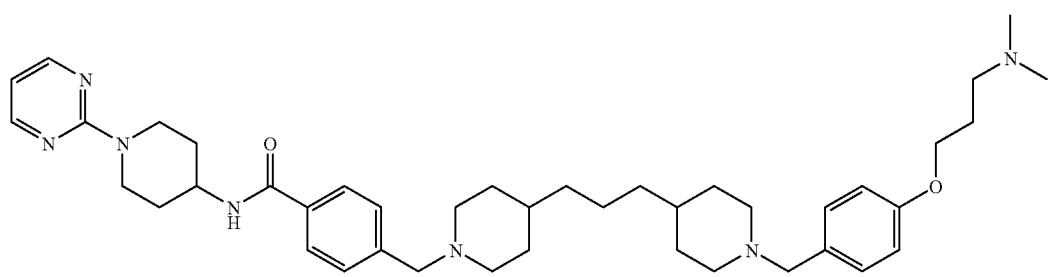
258
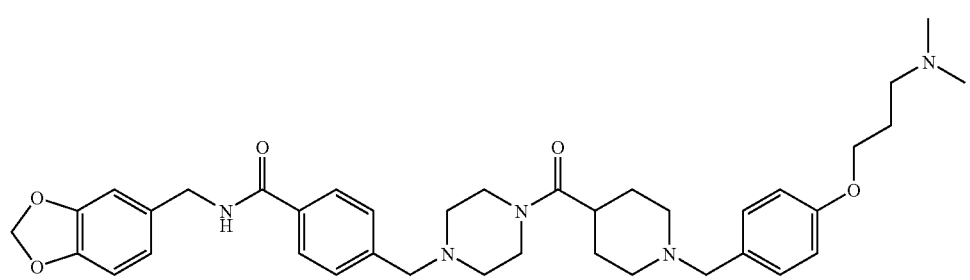
259
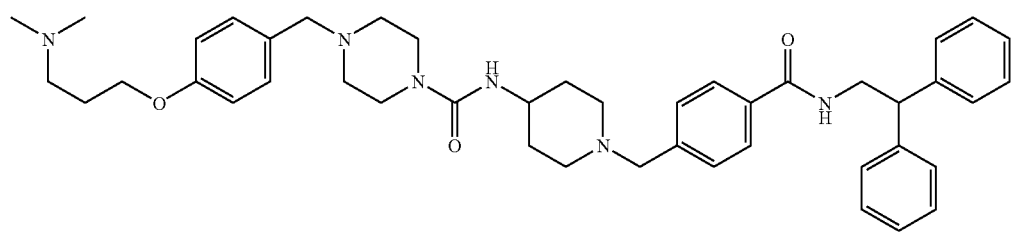
260
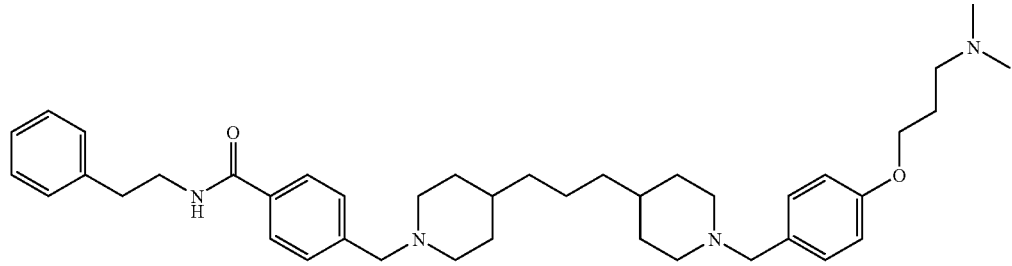
261
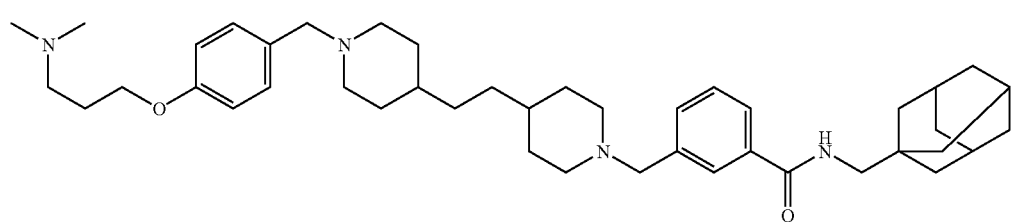
262

-continued
263
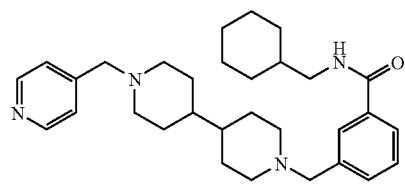
264
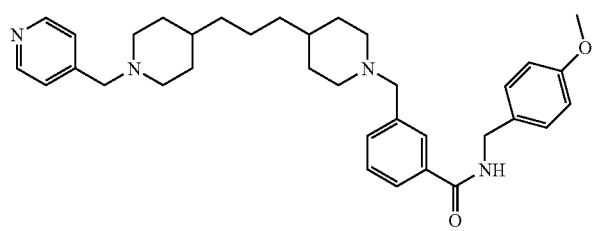
265
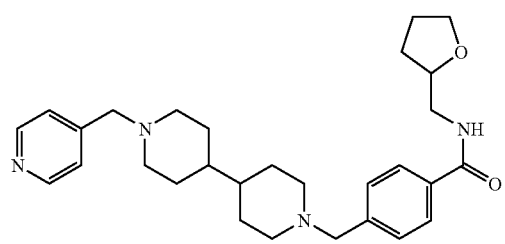
266
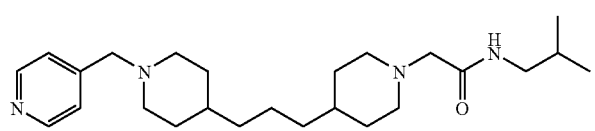
267
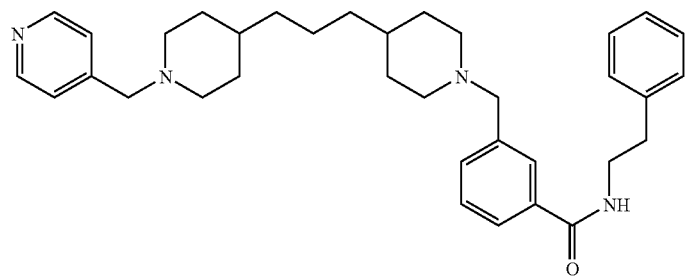
268
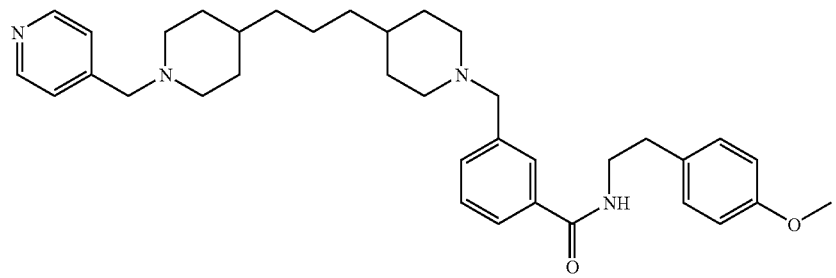
269
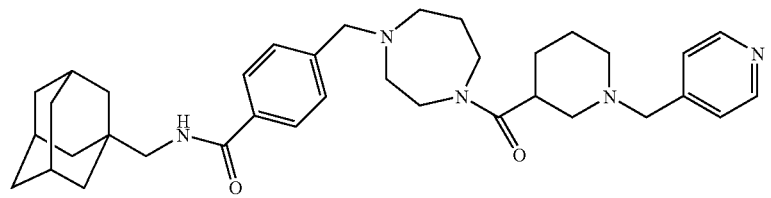
271
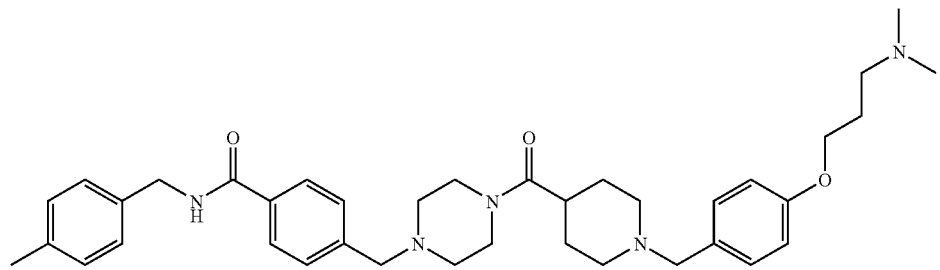

272

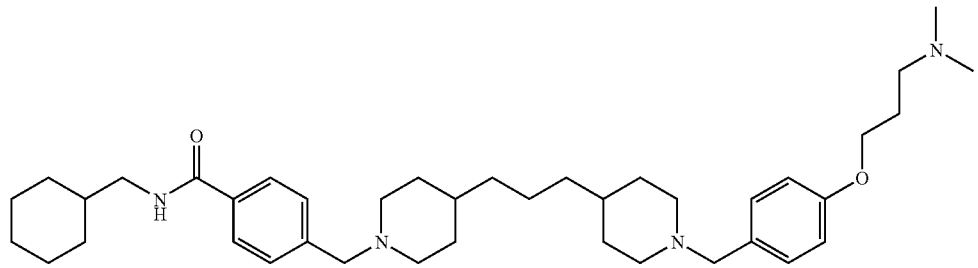

EXAMPLE 19

Compound 218 was prepared in solution in large quantity. The following is the procedure for the preparation of 218, which serves as the general protocol for preparation of other analogs.

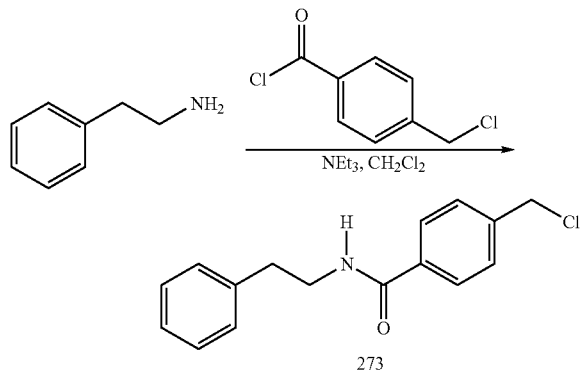

To a solution of Phenylethyl amine (120 mg, 1 mmole) and triethyl amine (200 mg, 2 mmole) in $CH_2Cl_2$ (10 mL) at 0° C. was added 4-(Chloromethyl)benzoyl chloride (230 mg, 1.2 mmole). After 30 min., the reaction mixture was poured into a separational funnel and washed with 1N HCl (10 mL), 1N NaOH (10 mL) and brine (10 mL). The organic layer was separated, dried over $Na_2SO_4$, and filtered. The filtrate was concentrated to give compound 273 as colorless oil (260 mg, 95%).

To a refluxed solution of compound 273 (260 mg, 0.95 mmole) in THF (10 mL) was added piperazine (430 mg, 5 mmole). The mixture was under reflux for 1 h and cooled to room temperature. Solvent was removed and the residue was dissolved in EtOAc (20 mL), which was washed with $H_2O$ (2×10 mL), 1N NaOH (10 mL) and brine (10 mL). The organic layer was separated, dried over $Na_2SO_4$, and filtered. The filtrate was concentrated to give compound 274 as a slightly yellow oil (290 mg, 95%).

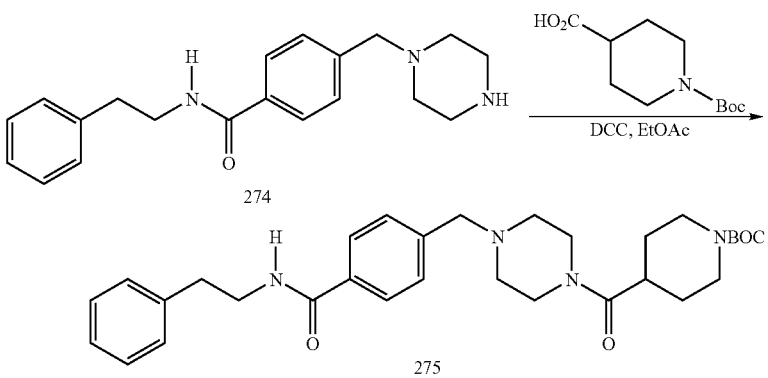

To a solution of Boc-isonipecotic acid (230 mg, 1 mmole) in EtOAc (10 mL) at 0° C. was added DCC (206 mg, 1 mmole) followed by the addition of compound 274 (290 mg, 0.9 mmole) in EtOAc (5 mL). The reaction mixture was stirred at room temperature for 8 h, and filtered. The filtrate was concentrated. Flash chromatography of the residue gave compound 275 as a colorless oil (390 mg, 80%)

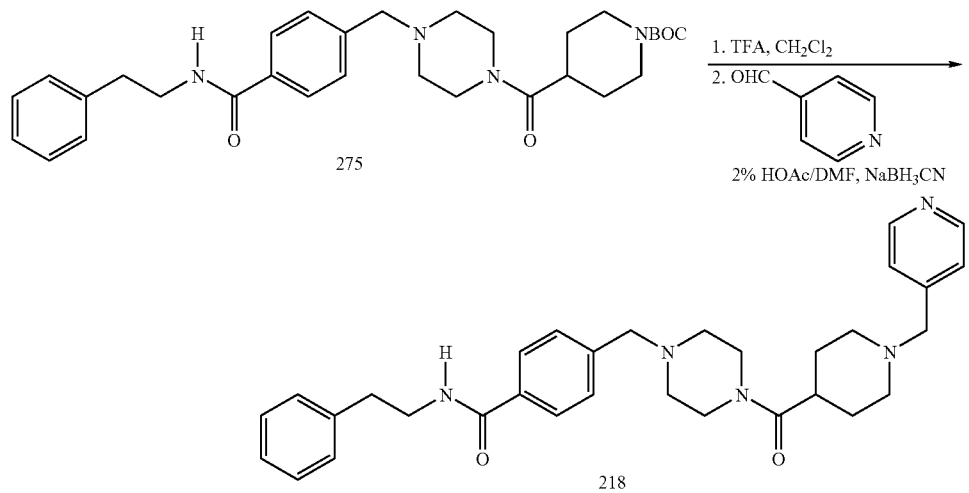

To a solution of compound 275 (270 mg, 0.5 mmole) in CH₂Cl₂ (5 mL) was added trifluoroacetic acid (0.5 mL). After 30 min., the mixture was concentrated, and the residue was dissolved in EtOAc (10 mL), which was washed with 1N NaOH (10 mL) and brine (10 mL). The organic layer was separated, dried over Na₂SO4 and filtered. The filtrate was concentrated and the residue was dissolved in DMF (5 mL). Acetic acid (0.2 mL), 4-pyridinecarboxaldehyde (64 mg, 0.6 mmole) and NaBH₃CN (64 mg, 1 mmole) were added to the solution. The reaction mixture was kept at room temperature for 8 h. EtOAc (15 mL) and H₂O (10 mL) were added to the mixture, and the mixtures were poured into a separational funnel. The organic layer was washed with H₂O (10 mL), 1N NaOH (10 mL) and brine (10 mL), separated and dried over Na₂SO4. After filtration, the filtrate was concentrated. Flash chromatography of the residue to give compound 218 as a white foam (132 mg, 50%).

Following the procedure of Examples 1 to 17 the compounds in Table 5 were prepared.

TABLE 5

| Compound No. | Structure |
|---|---|
| 276 | 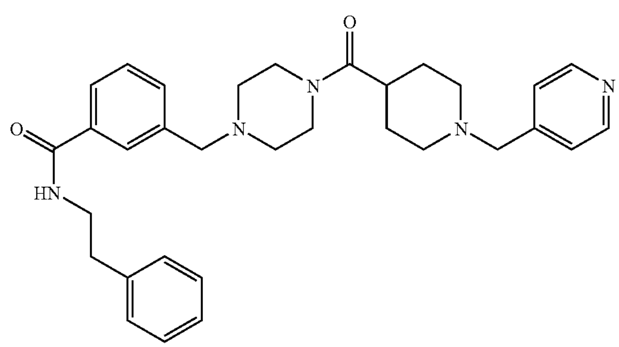 |
| 277 | 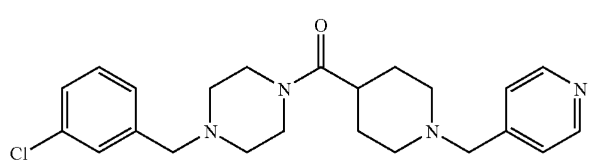 |
| 278 | 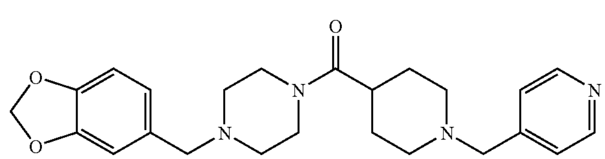 |

TABLE 5-continued
| Compound No. | Structure |
|---|---|
| 279 | 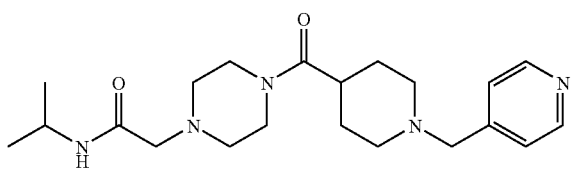 |
| 280 | 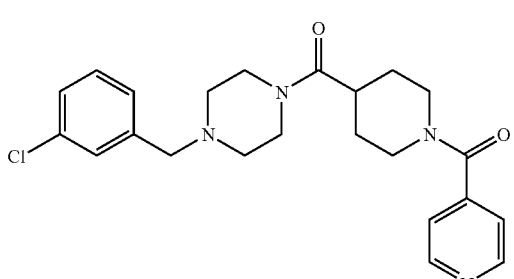 |
| 281 | 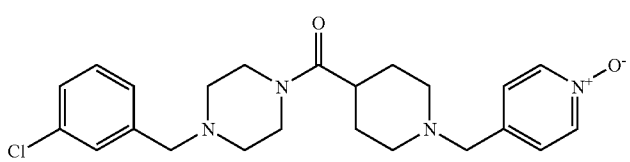 |
| 282 | 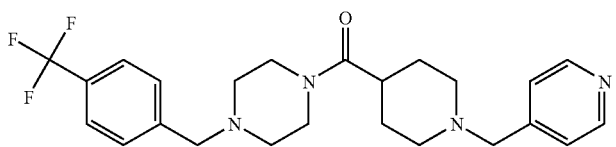 |
| 284 | 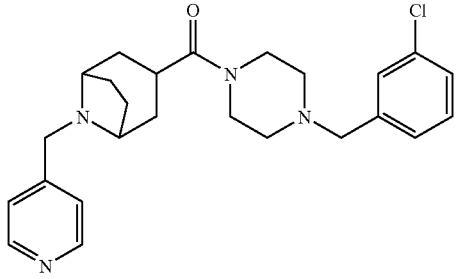 |
| 285 | 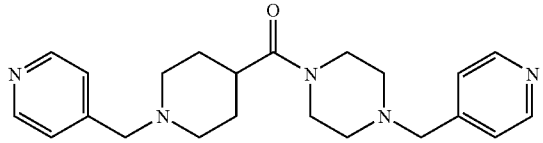 |
| 287 | 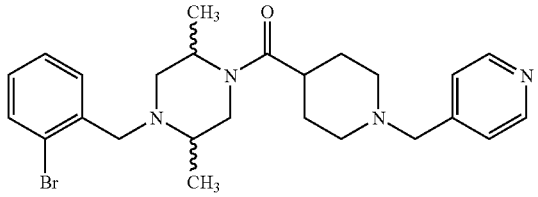 |

TABLE 5-continued
| Compound No. | Structure |
|---|---|
| 288 | 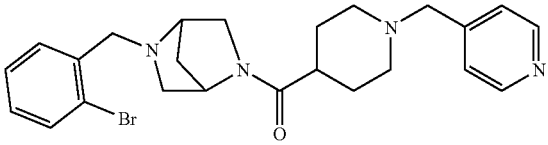 |
| 289 | 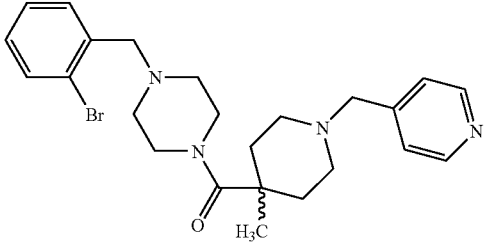 |
| 290 | 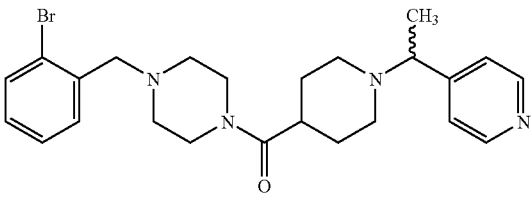 |
| 291 | 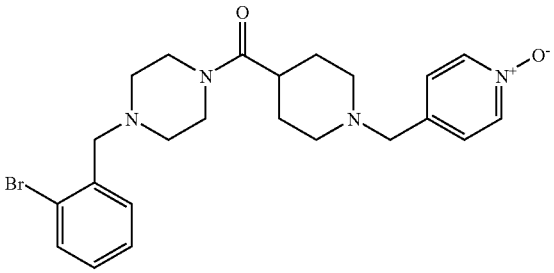 |
| 292 | 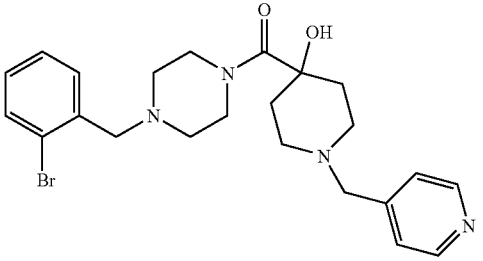 |
| 293 | 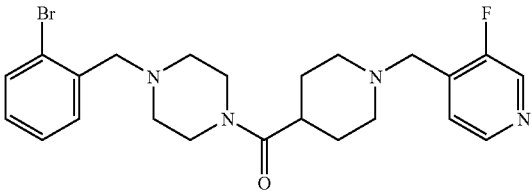 |

TABLE 5-continued
| Compound No. | Structure |
|---|---|
| 294 | 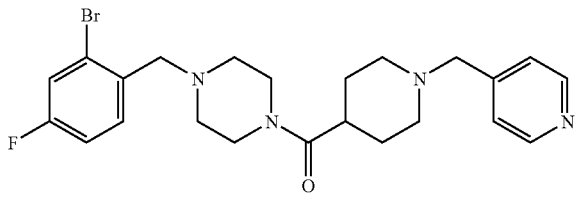 |
| 295 | 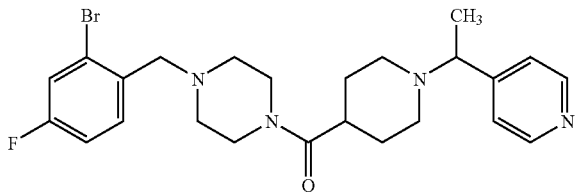 |
| 296 | 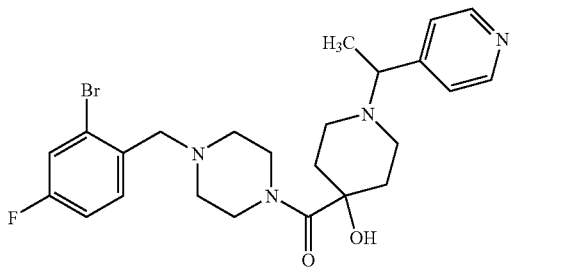 |
| 297 | 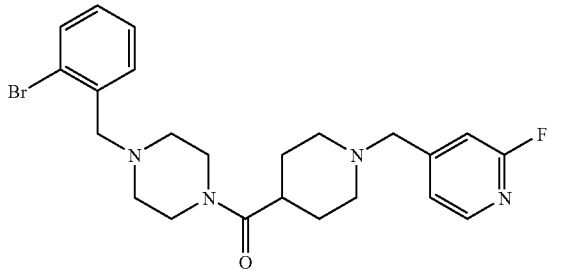 |
| 298 | 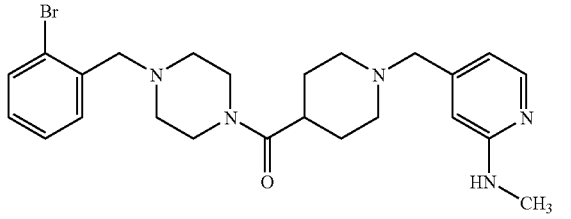 |
| 299 | 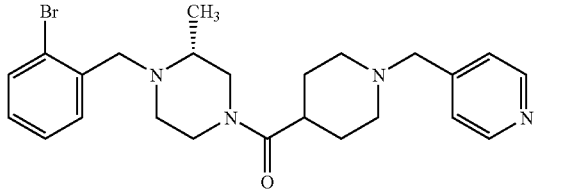 |

TABLE 5-continued

| Compound No. | Structure |
|---|---|
| 300 | 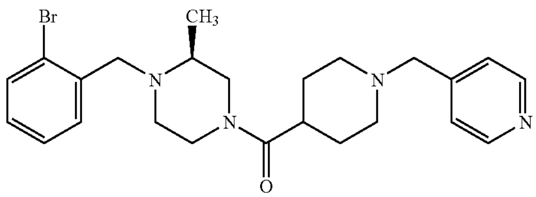 |
| 306 | 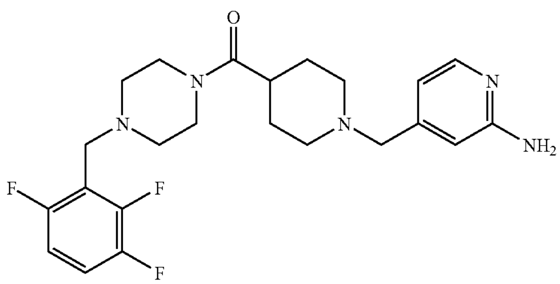 |
| 309 | 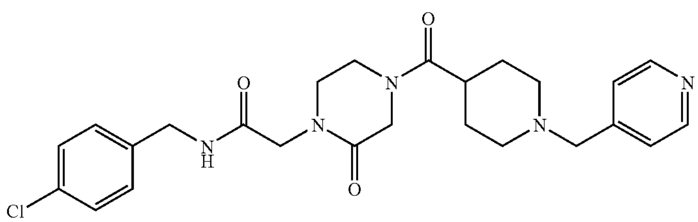 |
| 310 | 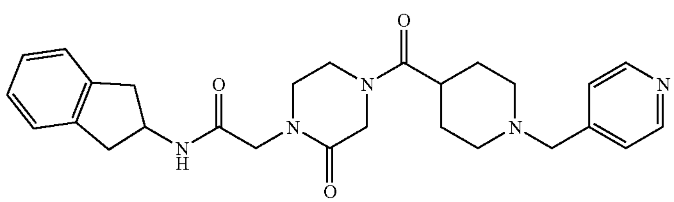 |
| 311 | 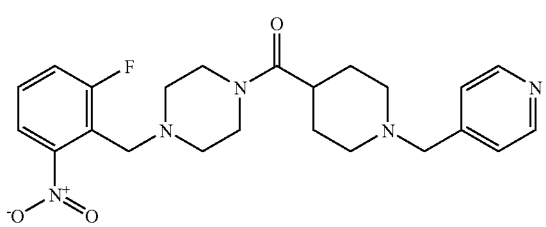 |
| 312 | 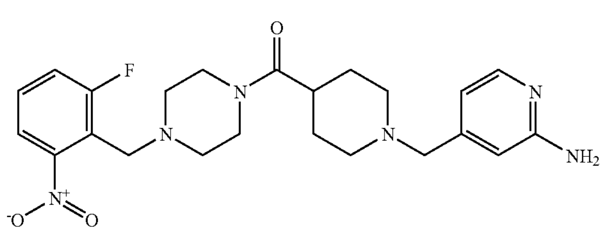 |

TABLE 5-continued

| Compound No. | Structure |
|---|---|
| 313 | 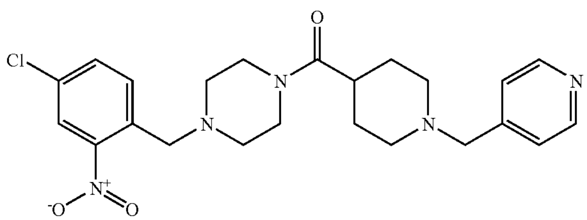 |
| 314 | 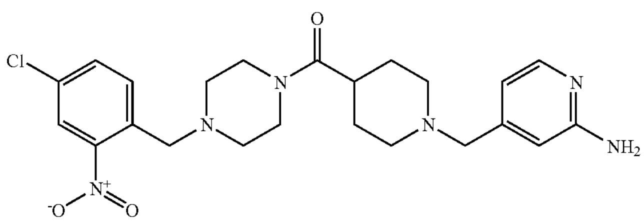 |
| 315 | 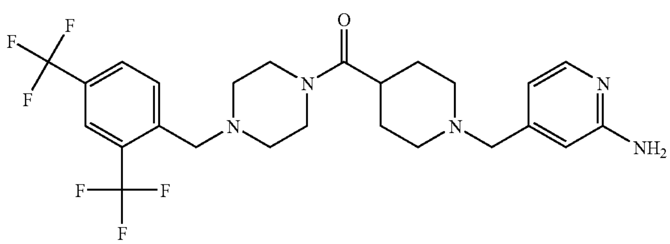 |
| 316 | 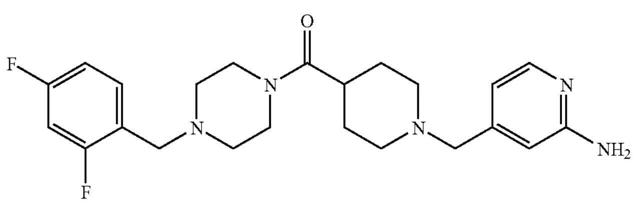 |
| 317 | 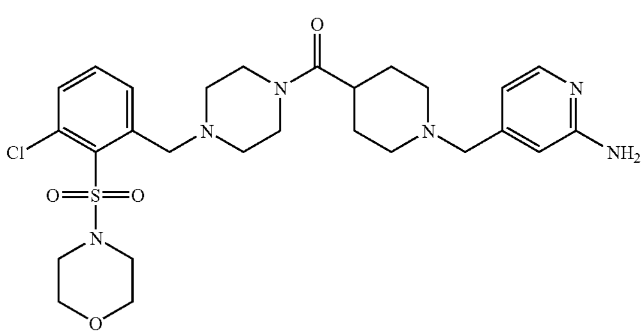 |
| 318 | 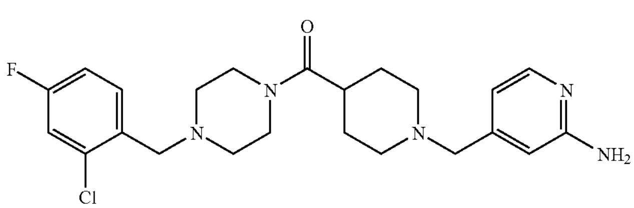 |

TABLE 5-continued

| Compound No. | Structure |
|---|---|
| 319 | 2-(trifluoromethoxy)benzyl-piperazine-carbonyl-piperidine-methyl-(2-aminopyridin-4-yl) |
| 321 | 2,6-dichlorobenzyl-piperazine-carbonyl-piperidine-methyl-(2-aminopyridin-4-yl) |
| 322 | 2-bromobenzyl-piperazine-carbonyl-piperidine-methyl-(2-aminopyridin-4-yl) |
| 323 | 2-chlorobenzyl-piperazine-carbonyl-piperidine-methyl-(2-aminopyridin-4-yl) |
| 324 | 2-fluoro-6-(trifluoromethyl)benzyl-piperazine-carbonyl-piperidine-methyl-(2-aminopyridin-4-yl) |
| 325 | 2-(difluoromethoxy)benzyl-piperazine-carbonyl-piperidine-methyl-(2-aminopyridin-4-yl) |

TABLE 5-continued
| Compound No. | Structure |
|---|---|
| 326 | 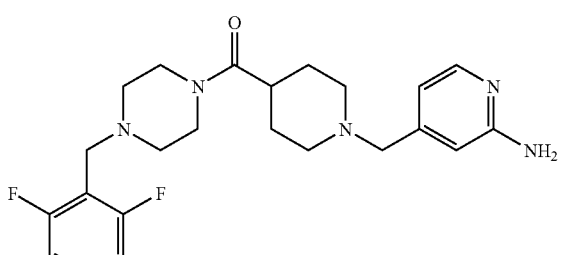 |
| 327 | 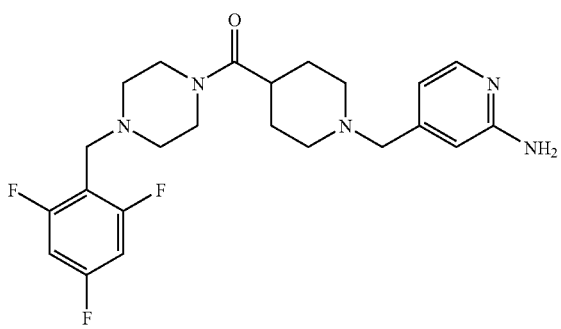 |
| 328 | 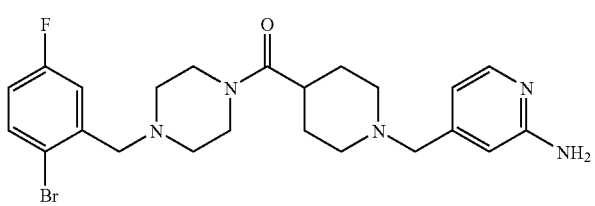 |
| 329 | 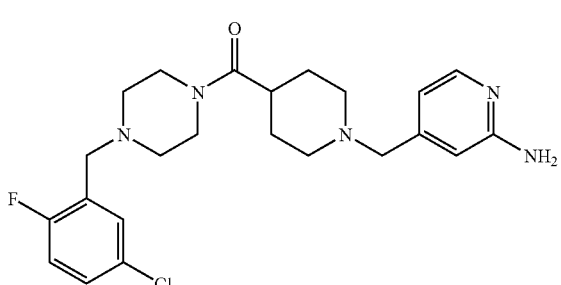 |
| 330 | 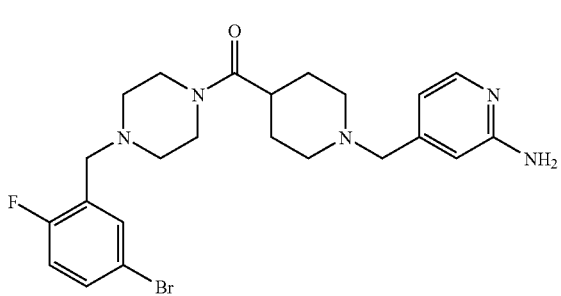 |

TABLE 5-continued
| Compound No. | Structure |
|---|---|
| 331 | 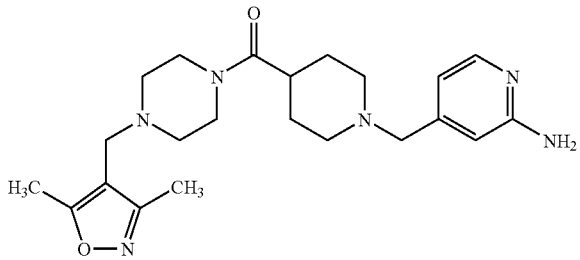 |
| 332 | 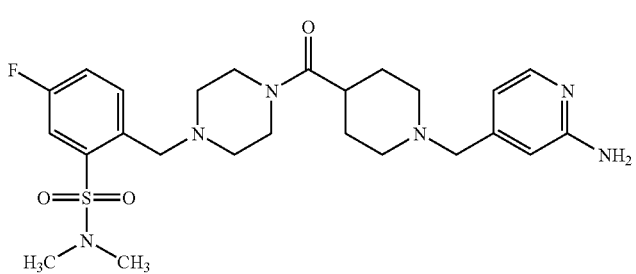 |
| 333 | 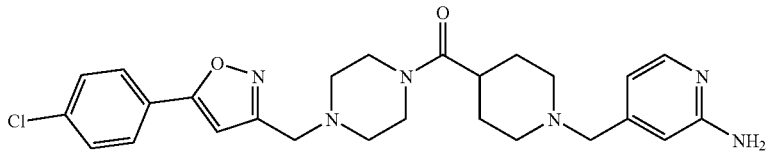 |
| 334 | 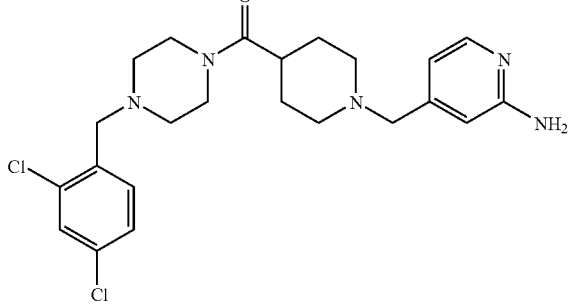 |
| 335 | 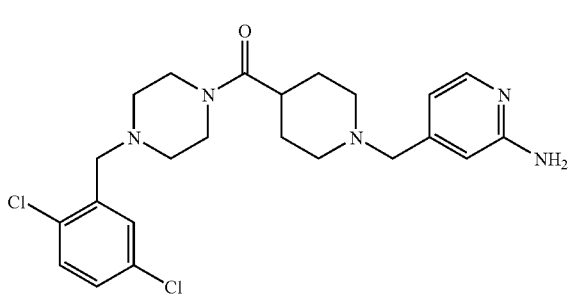 |

TABLE 5-continued

| Compound No. | Structure |
|---|---|
| 336 | 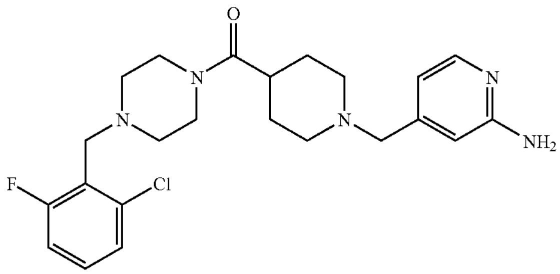 |
| 338 | 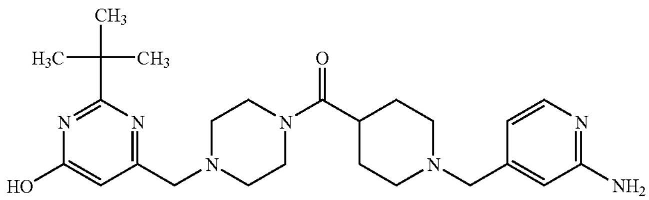 |
| 339 | 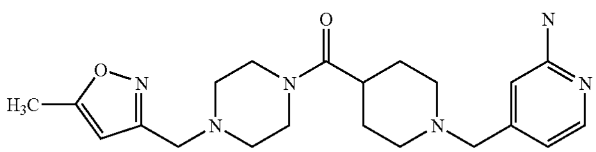 |
| 340 | 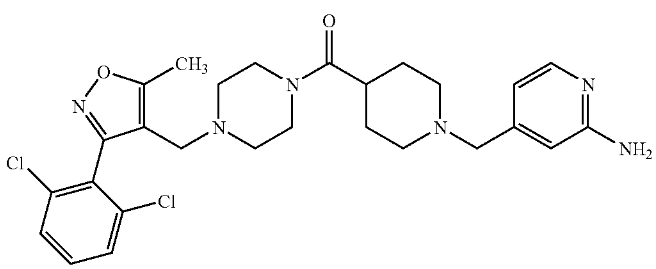 |
| 342 | 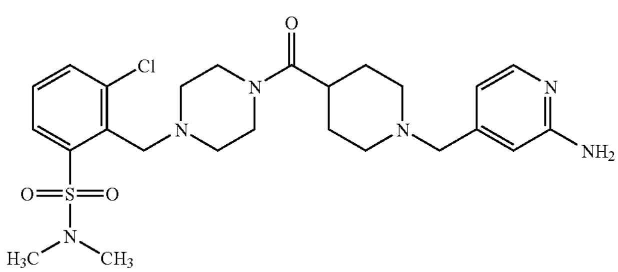 |
| 343 | 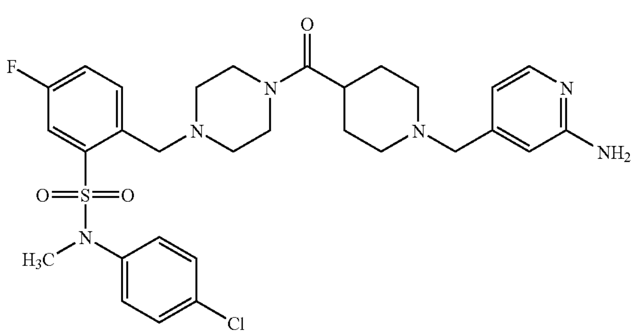 |

TABLE 5-continued

| Compound No. | Structure |
| --- | --- |
| 344 | 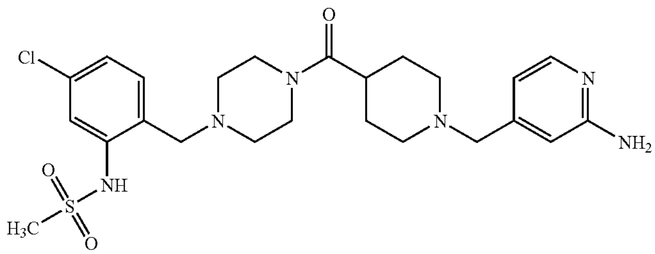 |
| 345 | 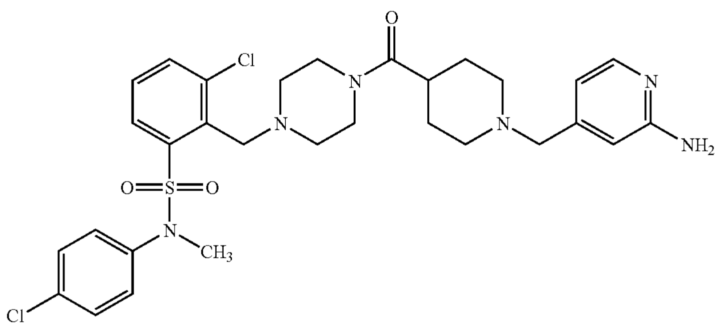 |
| 346 | 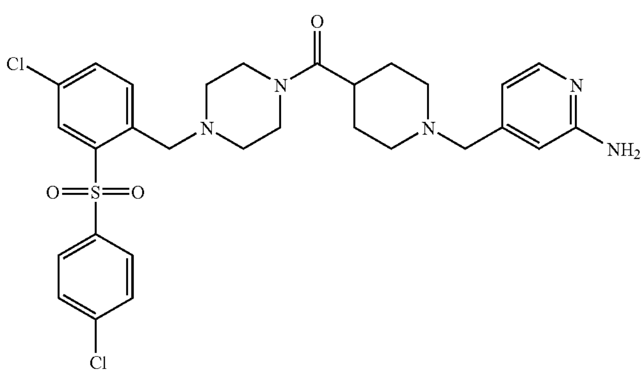 |
| 347 | 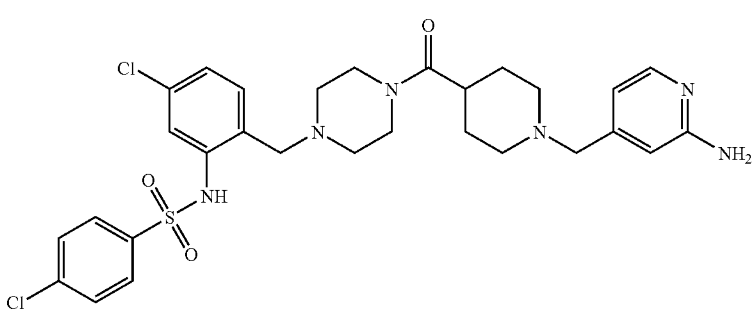 |

TABLE 5-continued

| Compound No. | Structure |
|---|---|
| 348 | 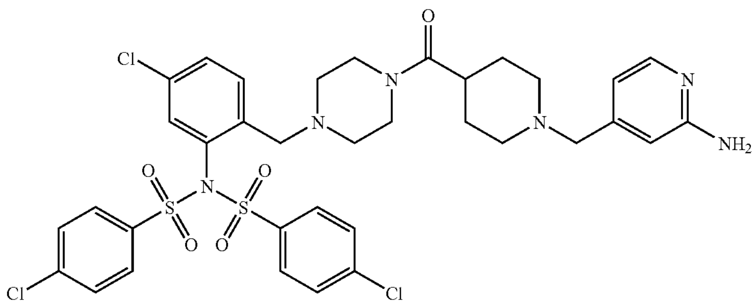 |
| 349 | 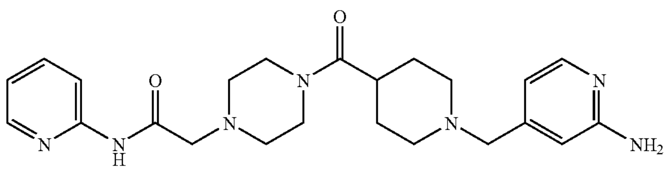 |
| 351 | 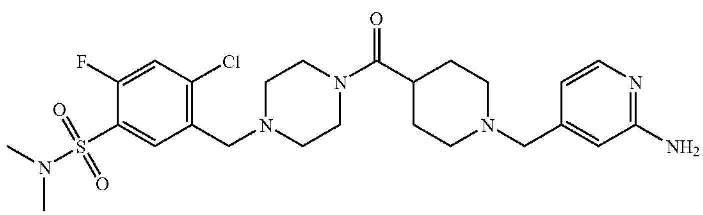 |
| 352 | 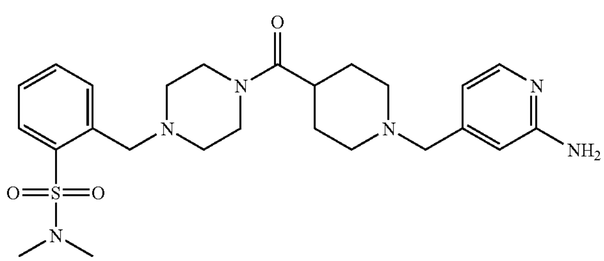 |
| 353 | 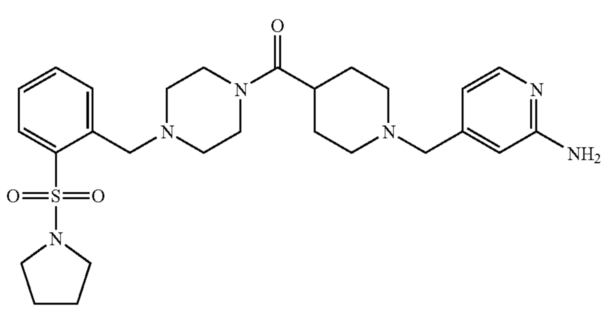 |
| 354 | 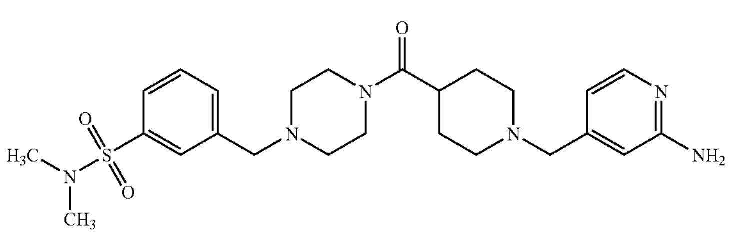 |

TABLE 5-continued

| Compound No. | Structure |
|---|---|
| 355 | 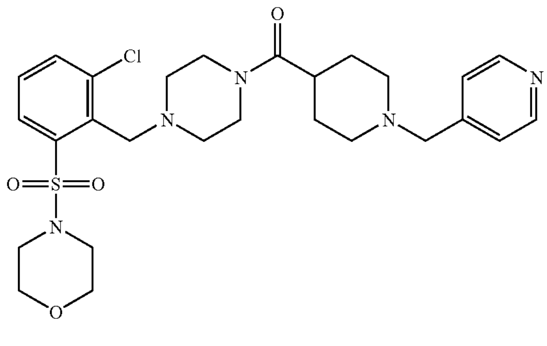 |
| 356 | 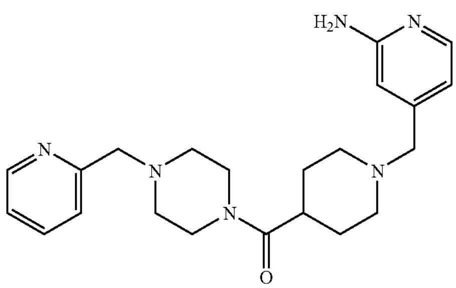 |
| 357 | 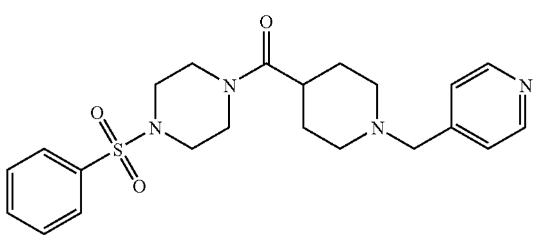 |
| 358 | 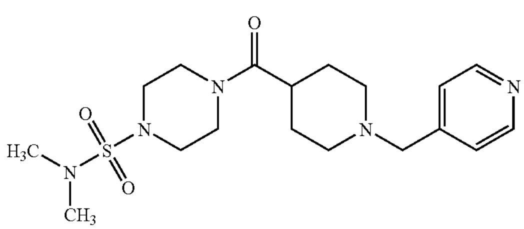 |
| 359 | 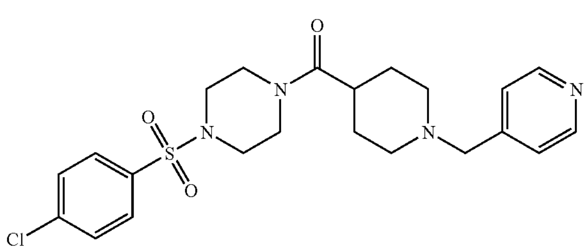 |

TABLE 5-continued

| Compound No. | Structure |
| --- | --- |
| 360 | (structure) |
| 361 | (structure) |
| 363 | (structure) |
| 364 | (structure) |
| 365 | (structure) |

TABLE 5-continued

| Compound No. | Structure |
|---|---|
| 366 | 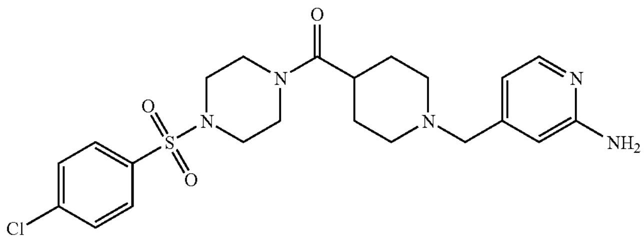 |
| 367 | 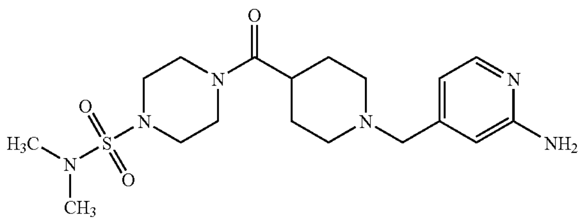 |
| 368 | 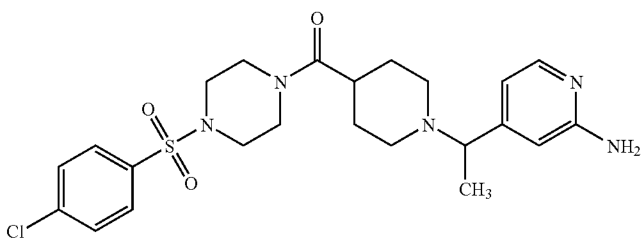 |
| 369 | 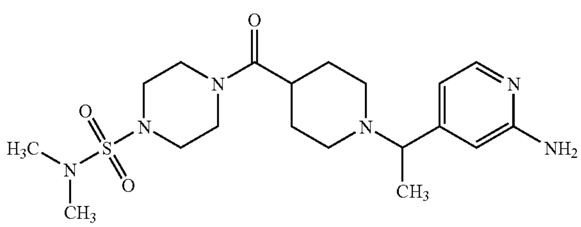 |
| 370 | 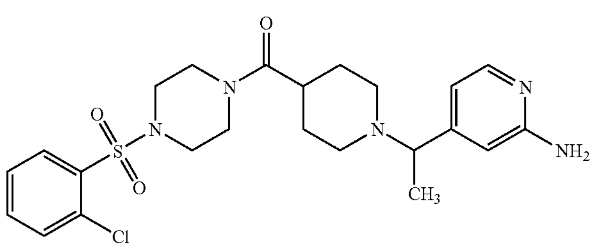 |
| 371 | 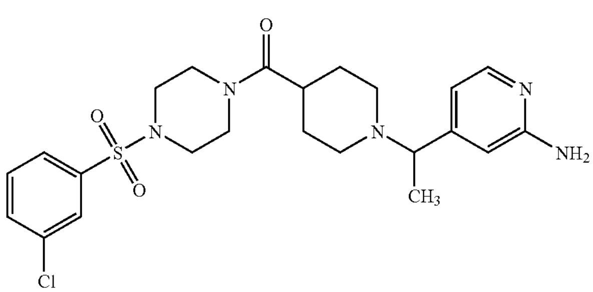 |

TABLE 5-continued

| Compound No. | Structure |
|---|---|
| 374 | 2-chlorophenylsulfonyl-piperazine-carbonyl-piperidine-CH2-(2-aminopyridin-4-yl) |
| 375 | 3-chlorophenylsulfonyl-piperazine-carbonyl-piperidine-CH2-(2-aminopyridin-4-yl) |
| 376 | 3,5-dichlorophenylsulfonyl-piperazine-carbonyl-piperidine-CH2-(2-aminopyridin-4-yl) |
| 377 | 3,4-dichlorophenylsulfonyl-piperazine-carbonyl-piperidine-CH2-(2-aminopyridin-4-yl) |
| 380 | 4'-fluorobiphenyl-4-sulfonyl-piperazine-carbonyl-piperidine-CH2-(2-aminopyridin-4-yl) |

TABLE 5-continued
| Compound No. | Structure |
|---|---|
| 381 | 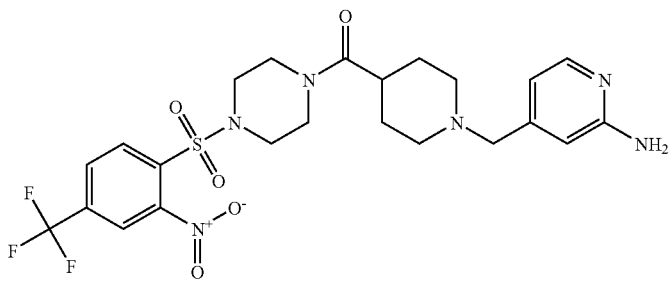 |
| 382 | 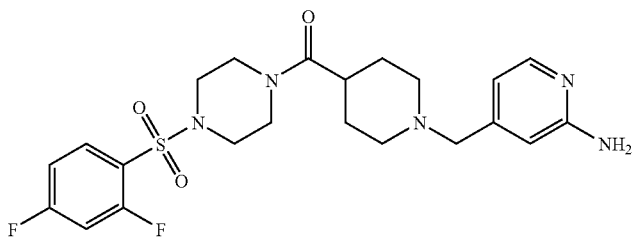 |
| 383 | 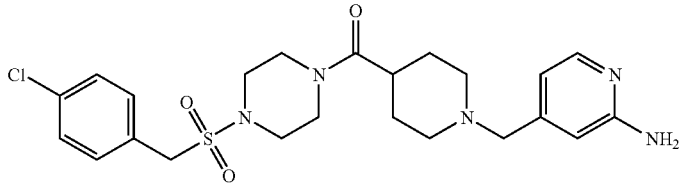 |
| 387 | 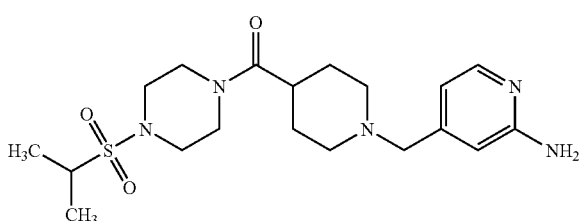 |
| 388 | 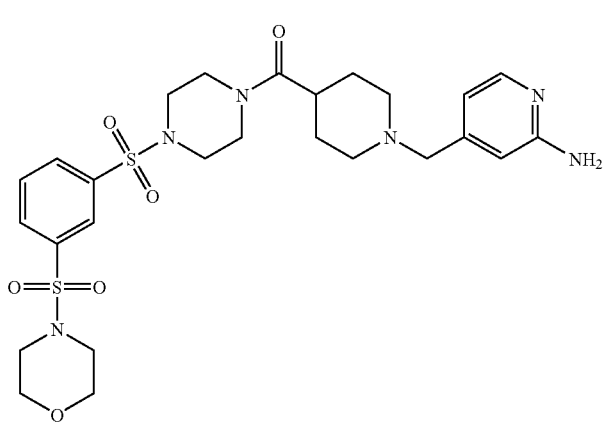 |

TABLE 5-continued

| Compound No. | Structure |
|---|---|
| 389 | 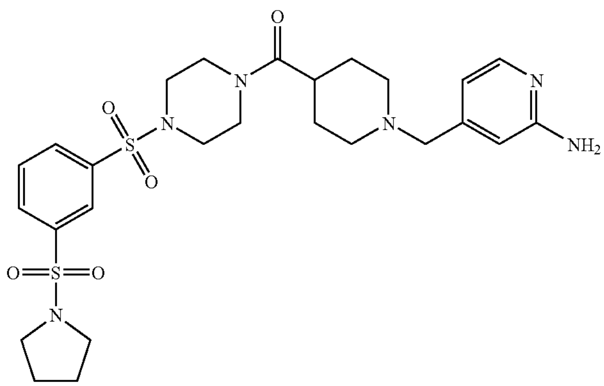 |
| 390 | 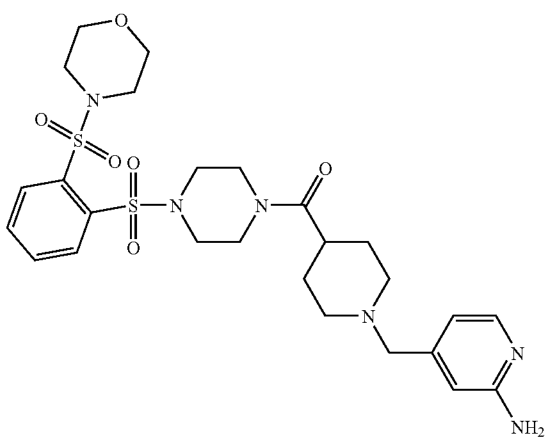 |
| 392 | 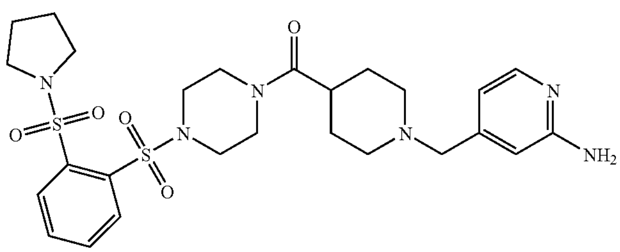 |
| 393 | 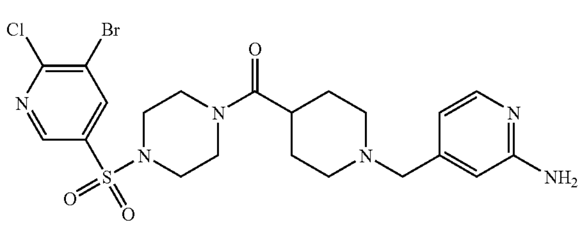 |

TABLE 5-continued

| Compound No. | Structure |
| --- | --- |
| 394 | 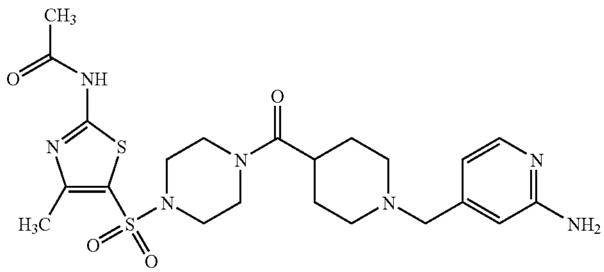 |
| 395 | 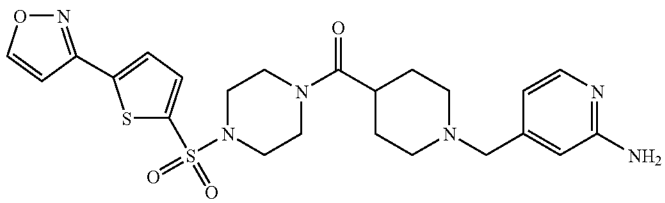 |
| 396 | 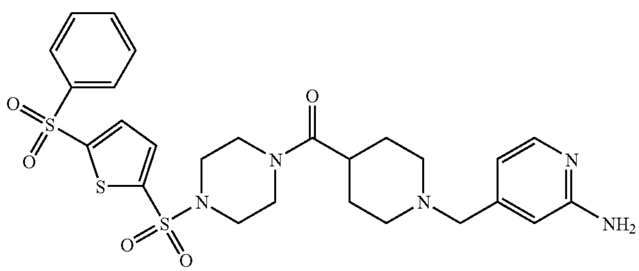 |
| 397 | 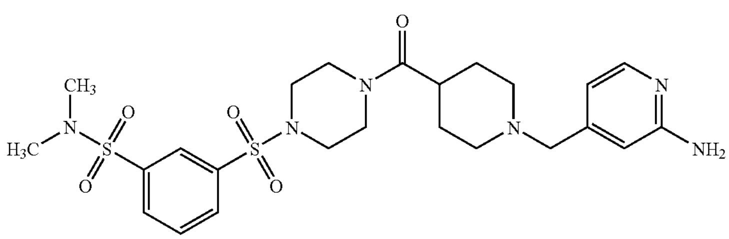 |
| 398 | 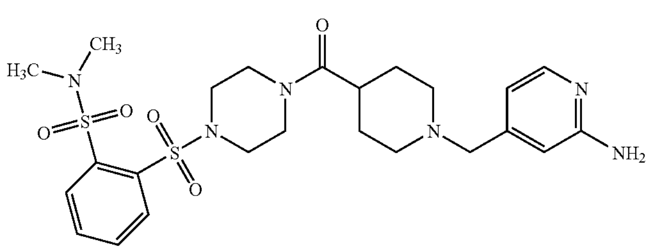 |
| 399 | 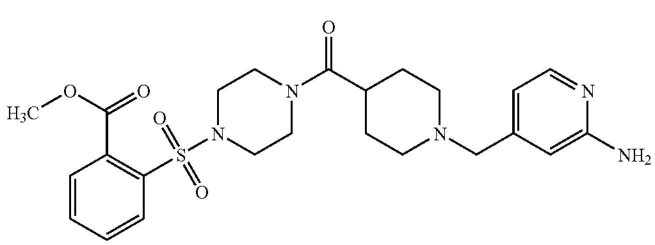 |

TABLE 5-continued
| Compound No. | Structure |
| --- | --- |
| 400 | 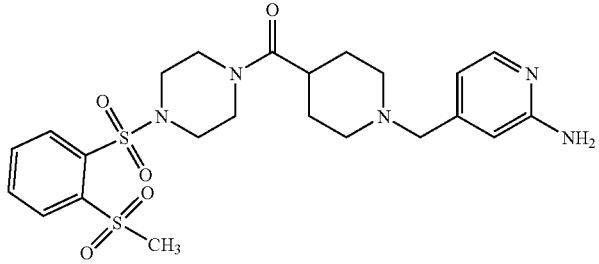 |
| 401 | 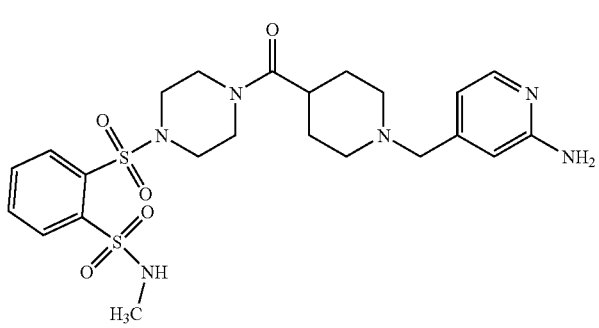 |
| 402 | 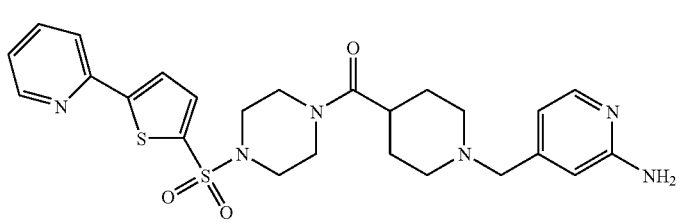 |
| 403 | 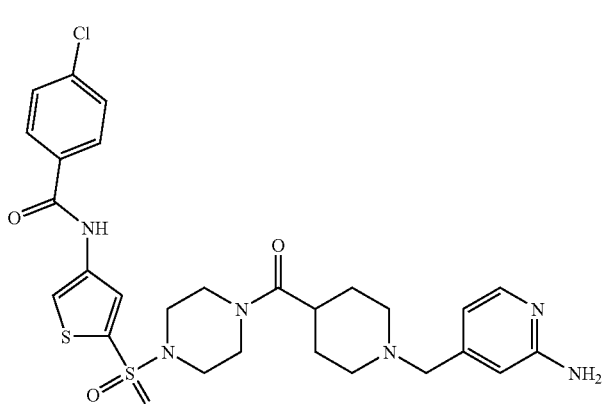 |
| 404 | 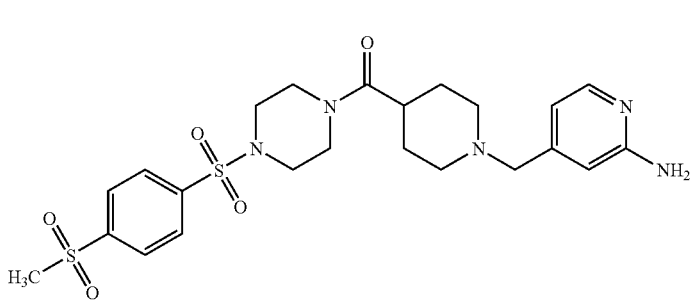 |

TABLE 5-continued

| Compound No. | Structure |
|---|---|
| 405 | 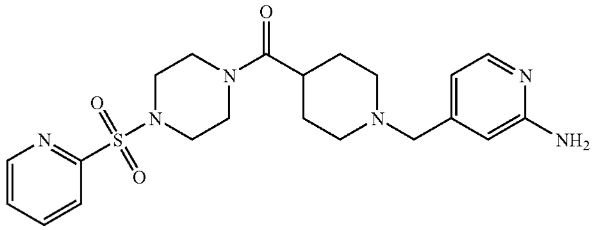 |
| 406 | 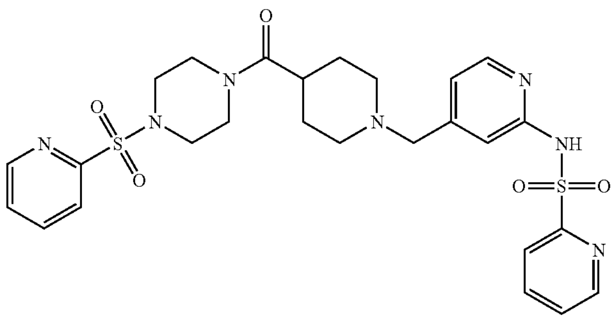 |
| 408 | 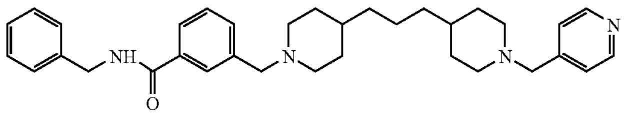 |
| 409 | 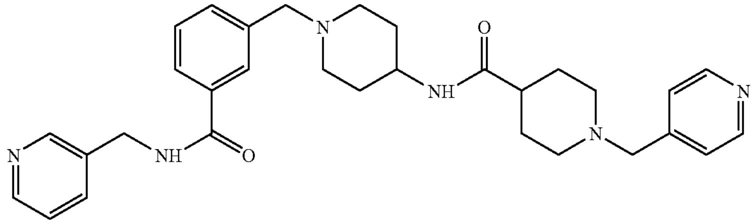 |
| 410 | 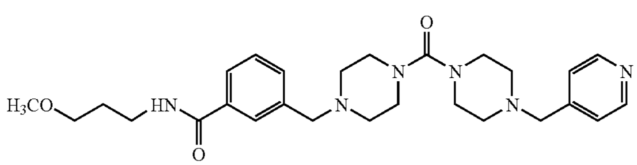 |

General Procedure for $H_3$-Receptor Binding Assay

The source of the $H_3$ receptors in this experiment was guinea pig brain. The animals weighed 400–600 g. The brain tissue was homogenized with a solution of 50 mM Tris, pH 7.5. The final concentration of tissue in the homogenization buffer was 10% w/v. The homogenates were centrifuged at 1,000×g for 10 min. in order to remove clumps of tissue and debris. The resulting supernatants were then centrifuged at 50,000×g for 20 min. in order to sediment the membranes, which were next washed three times in homogenization buffer (50,000×g for 20 min. each). The membranes were frozen and stored at −70° C. until needed.

All compounds to be tested were dissolved in DMSO and then diluted into the binding buffer (50 mM Tris, pH 7.5) such that the final concentration was 2 μg/ml with 0.1% DMSO. Membranes were then added (400 μg of protein) to the reaction tubes. The reaction was started by the addition of 3 nM[$^3$H]R-α-methyl histamine (8.8 Ci/mmol) or 3 nM [$^3$H]N$^{60}$ -methyl histamine (80 Ci/mmol) and continued under incubation at 30° C. for 30 min. Bound ligand was separated from unbound ligand by filtration, and the amount of radioactive ligand bound to the membranes was quantitated by liquid scintillation spectrometry. All incubations were performed in duplicate and the standard error was always less than 10%. Compounds that inhibited more than 70% of the specific binding of radioactive ligand to the receptor were serially diluted to determine a $K_i$ (nM).

Compounds 89 to 157, 159 to 168, 276 to 279, 282, 284, 285, 287 to 300, 306, 309 to 319, 321 to 336, 338 to 340, 342 to 349, 351 to 361, 363 to 371, 374 to 377, 380 to 383, 387 to 390, 392 to 406, and 408 to 410 had a $K_i$ within the range of about 0.2 to about 600 nM.

Preferred Compounds 93, 276, 306, 317, 328, 331, 332, 333, 336, 343, 366, 367, 374 and 376 had a $K_i$ within the range of about 0.2 to about 35 nM.

More preferred Compounds 306, 332, 333, 336, 366, 374 and 374 had a $K_i$ within the range of about 2 to about 22 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 150 mg, preferably from about 1 mg to about 75 mg, more preferably from about 1 mg to about 50 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 75 mg/day, in two to four divided doses.

While the present has been described in conjunction with the specific embodiments set forth above, many alternatives, modifications and variations thereof will be apparent to those of ordinary skill in the art. All such alternatives, modifications and variations are intended to fall within the spirit and scope of the present invention.

What is claimed is:

1. A compound of the formula:

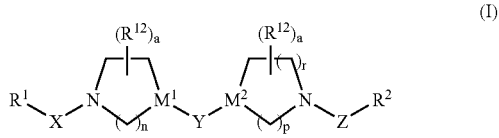

or a pharmaceutically acceptable salt or solvate thereof, wherein:

(A) $R^1$ is selected from:
(1) aryl;
(2) heteroaryl;
(3) heterocycloalkyl
(4) alkyl;
(5) —C(O)N($R^{4B}$)$_2$;
(6) cycloalkyl;
(7) arylalkyl;
(8) heteroarylheteroaryl; or
(9) a group selected from:

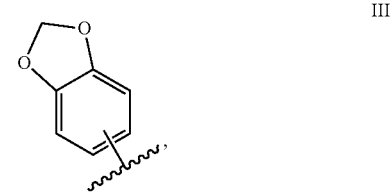

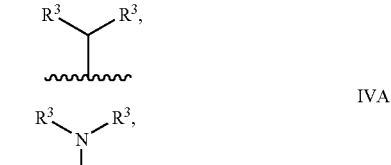

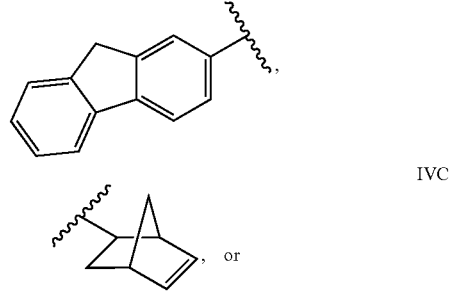

-continued

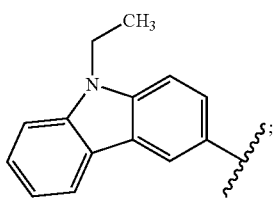

IVD said aryl, heteroaryl, aryl portion of arylalkyl, phenyl ring of formula II, phenyl ring of formula III, phenyl rings of formula IVB, or phenyl rings of formula IVD are optionally substituted with 1 to 3 substituents independently selected from:
(1) halogen;
(2) hydroxyl;
(3) lower alkoxy;
(4) -Oaryl;
(5) —$SR^{22}$;
(6) —$CF_3$;
(7) —$OCF_3$;
(8) —$OCHF_2$;
(9) —$NR^4R^5$;
(10) phenyl;
(11) $NO_2$,
(12) —$CO_2R^4$;
(13) —$CON(R^4)_2$ wherein each $R^4$ is the same or different;
(14) —$S(O)_2R^{22}$;
(15) —$S(O)_2N(R^{20})_2$ wherein each $R^{20}$ is the same or different;
(16) —$N(R^{24})S(O)_2R^{22}$;
(17) —CN;
(18) —$CH_2OH$;
(19) —$OCH_2CH_2OR^{22}$;
(20) alkyl;
(21) substituted phenyl wherein said phenyl has 1 to 3 substituents independently selected from alkyl, halogen, —CN, —$NO_2$, —$OCHF_2$, -Oalkyl; or
(22) -Oalkylaryl wherein said aryl group is optionally substituted with 1 to 3 independently selected halogens;
(B) X is selected from alkyl or —$S(O)_2$—;
(C) Y is selected from —C(O)—, —C(S)—, or —$NR^4C(O)$—; with the proviso that when $M^1$ is N, then Y is not —$NR^4C(O)$—;
(D) $M^1$ is CH or N and $M^2$ is N;
(E) Z is selected from: $C_1$–$C_6$ alkyl, —$SO_2$—, —C(O)— or —$C(O)NR^4$—;
(F) $R^2$ is selected from:
(1) a six-membered heteroaryl ring having 1 or 2 heteroatoms independently selected from N or N—O, with the remaining ring atoms being carbon;
(2) a five-membered heteroaryl ring having 1 to 3 heteroatoms selected from nitrogen, oxygen, or sulfur with the remaining ring atoms being carbon; or
(3) an alkyl group;
(4) substituted phenyl wherein said substituted phenyl is substituted with 1 to 3 substituents independently selected from: halogen, -Oalkyl, —$OCF_3$, —$CF_3$, —CN, —$NO_2$, —$NHC(O)CH_3$, or —$O(CH_2)_qN(R^{10A})_2$;
(5) —$N(R^{11A})_2$ wherein each $R^{11A}$ is independently selected from: H, alkyl or aryl;

(6) a group of the formula:

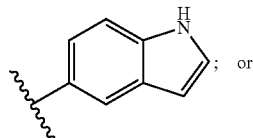

; or (7) a heteroarylheteroaryl group; said five membered heteroaryl ring ((F)(2) above) or six-membered heteroaryl ring ((F)(1) above) is optionally substituted with 1 to 3 substituents selected from:
(a) halogen;
(b) hydroxyl;
(c) lower alkyl;
(d) lower alkoxy;
(e) —$CF_3$;
(f) —$NR^4R^5$;
(g) phenyl;
(h) —$NO_2$;
(i) —$C(O)N(R^4)_2$ (wherein each $R^4$ is the same or different);
(j) —$C(O)_2R^4$; or
(k) phenyl substituted with 1 to 3 substituents independently selected from: halogen, -Oalkyl, —$OCF_3$, —$CF_3$, —CN, —$NO_2$ or —$O(CH_2)_qN(R^{10A})_2$;
(G) $R^3$ is is selected from:
(1) aryl;
(2) heteroaryl;
(3) heterocycloalkyl
(4) alkyl; or
(5) cycloalkyl;
wherein said aryl or heteroaryl $R^3$ groups is optionally substituted with 1 to 3 substituents independently selected from:
(a) halogen;
(b) hydroxyl;
(c) lower alkoxy;
(d) -Oaryl;
(e) —$SR^{22}$;
(f) —$CF_3$;
(g) —$OCF_3$;
(h) —$OCHF_2$;
(i) —$NR^4R^5$;
phenyl;
(k) —$NO_2$,
(l) —$CO_2R^4$;
(m) —$CON(R^4)_2$ wherein each $R^4$ is the same or different;
(n) —$S(O)_2R^{22}$;
(o) —$S(O)_2N(R^{20})_2$ wherein each $R^{20}$ is the same or different;
(p) —$N(R^{24})S(O)_2R^{22}$;
(q) —CN;
(r) —$CH_2OH$;
(s) —$OCH_2CH_2OR^{22}$; or
(t) alkyl;
(H) $R^4$ is selected from:
(1) hydrogen;
(2) $C_1$–$C_6$alkyl;
(3) cycloalkyl;
(4) cycloalkylalkyl;
(5) heterocycloalkylalky;
(6) bridged bicyclic cycloalkyl ring;

(7) aryl having a fused heterocycloalkyl ring bound to said aryl ring;
(8) aryl;
(9) arylalkyl:
(10) alkylaryl;
(11) —$(CH_2)_d CH(R^{124})_2$ wherein d is 1 to 3, and each $R^{124}$ is independently selected from phenyl or substituted phenyl, said substituted phenyl being substituted with 1 to 3 substituents independently selected from: halogen, -Oalkyl, —$OCF_3$, —$CF_3$, —CN, or —$NO_2$;
(12) heterocycloalkylheteroaryl; or
(13) —($C_1$ to $C_6$)alkylene-O—$R^{22}$;
wherein the aryl $R^4$ group, the aryl portion of the arylalkyl $R^4$ group, or the aryl portion of the alkylaryl $R^4$ group is optionally substituted with 1 to 3 substituents independently selected from:
(a) halogen;
(b) hydroxyl;
(c) lower alkyl;
(d) lower alkoxy
(e) —$CF_3$;
(f) —$N(R^{20})(R^{24})$,
(g) phenyl;
(h) —$NO_2$;
(i) —$C(O)N(R^{20})_2$ (wherein each $R_{20}$ is the same or different),
(j) —$C(O)R^{22}$;
(i) —$(CH_2)_k$-cycloalkyl;
(j) —$(CH_2)_q$-aryl; or
(k) —$(CH_2)_m$—$OR^{22}$;
(I) each $R^{4B}$ is independently selected from; H, heteroaryl, alkyl, alkenyl, a group of the formula

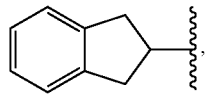

arylalkyl, or arylalkyl wherein the aryl moiety is substitued with 1–3 substituents independently selected from: halogen;
(J) $R^5$ is selected from: hydrogen, $C_1$–$C_6$ alkyl, —$C(O)R^{20}$, —$C(O)_2R^{20}$, —$C(O)N(R^{20})_2$ (wherein each $R^{20}$ is the same or different);
(K) each $R^{10A}$ is independently selected from H or $C_1$ to $C_6$ alkyl, or each $R^{10A}$, taken together with the nitrogen atom to which they are bound, forms a 4 to 7 membered heterocycloalkyl ring;
(L) $R^{12}$ is
(1) selected from alkyl, hydroxyl, alkoxy, or fluoro, provided that when $R^{12}$ is hydroxy or fluoro then $R^{12}$ is not bound to a carbon adjacent to a nitrogen; or
(2) $R^{12}$ forms an alkyl bridge from one ring carbon to another ring carbon;
(M) $R^{13}$ is
(1) selected from alkyl, hydroxyl, alkoxy, or fluoro, provided that when $R^{13}$ is hydroxy or fluoro then $R^{13}$ is not bound to a carbon adjacent to a nitrogen; or
(2) $R^{13}$ forms an alkyl bridge from one ring carbon to another ring carbon;
(N) $R^{20}$ is selected from hydrogen, alkyl, or aryl, wherein said aryl group is optionally substituted with from 1 to 3 groups independently selected from: halogen, —$CF_3$, —$OCF_3$, hydroxyl, or methoxy; or when two $R^{20}$ groups are present, said two $R^{20}$ groups taken together with the nitrogen to which they are bound form a five or six membered heterocyclic ring;
(O) $R^{22}$ is selected from: heterocycloalkyl, alkyl or aryl, wherein said aryl group is optionally substituted with 1 to 3 groups independently selected from halogen, —$CF_3$, —$OCF_3$, hydroxyl, or methoxy;
(P) $R^{24}$ is selected from: hydrogen, alkyl, —$SO_2R^{22}$, or aryl, wherein said aryl group is optionally substituted with 1 to 3 groups independently selected from halogen, —$CF_3$, —$OCF_3$, hydroxyl, or methoxy;
(Q) a is 0 to 2;
(R) b is 0 to 2;
(S) k is 1 to 5;
(T) m is 2 to 5;
(U) n is 1, 2 or 3 with the proviso that when $M^1$ is N, then n is not 1;
(V) p is 2; and
(W) r is 1.

2. The compound of claim 1 wherein $R^1$ is selected from:
(1) substituted aryl;
(2) substituted heteroaryl; or
(3) formula IVA wherein each $R^3$ is independently selected.

3. The compound of claim 2 wherein $R^1$ is selected from:
(1) substituted phenyl;
(2) substituted isoxazolyl; or
(3) —$N(CH_3)_2$.

4. The compound of claim 3 wherein $R^1$ is selected from:
(1) substituted phenyl wherein said phenyl group has 1 to 3 groups selected independently from:
(a) —$C(O)N(R^4)_2$;
(b) halo;
(c) —$S(O)_2R^{22}$;
(d) —$OCF_3$;
(e) —$OCHF_2$; or
(f) —$S(O)_2N(R^{20})_2$; or
(2) substituted isoxazolyl wherein said isoxazolyl group has 1 or 2 substituents independently selected from:
(a) alkyl; or
(b) substituted phenyl.

5. The compound of claim 1 wherein $R^1$ is selected from:

(a)
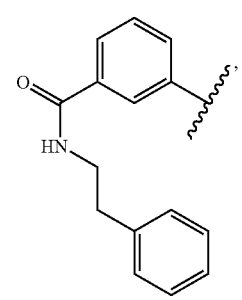

(b)
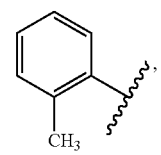

-continued
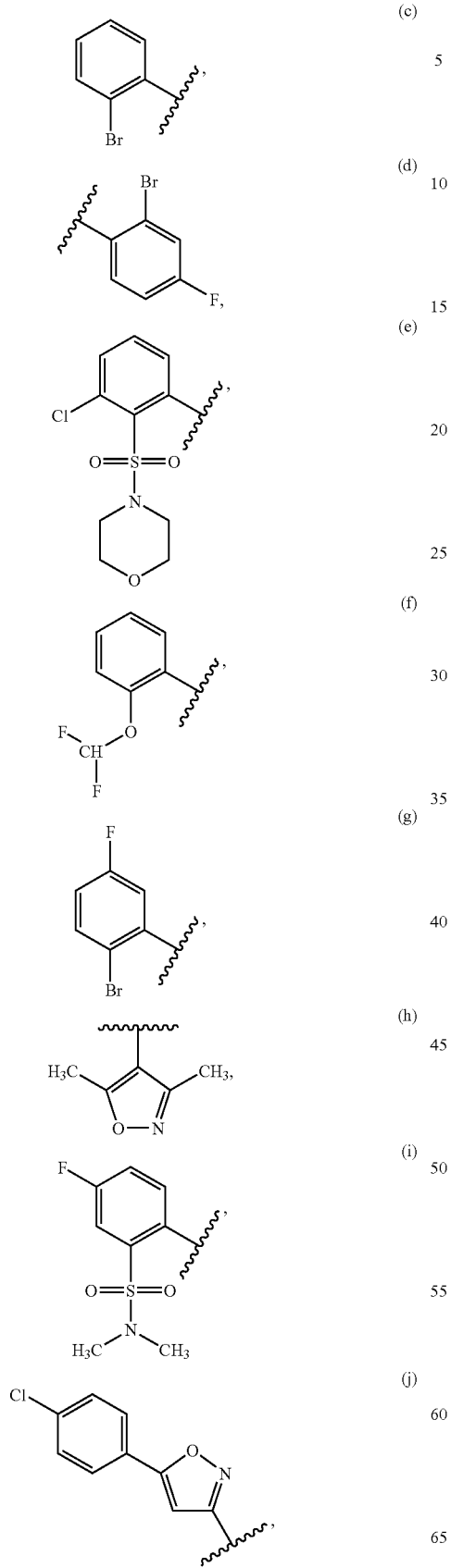
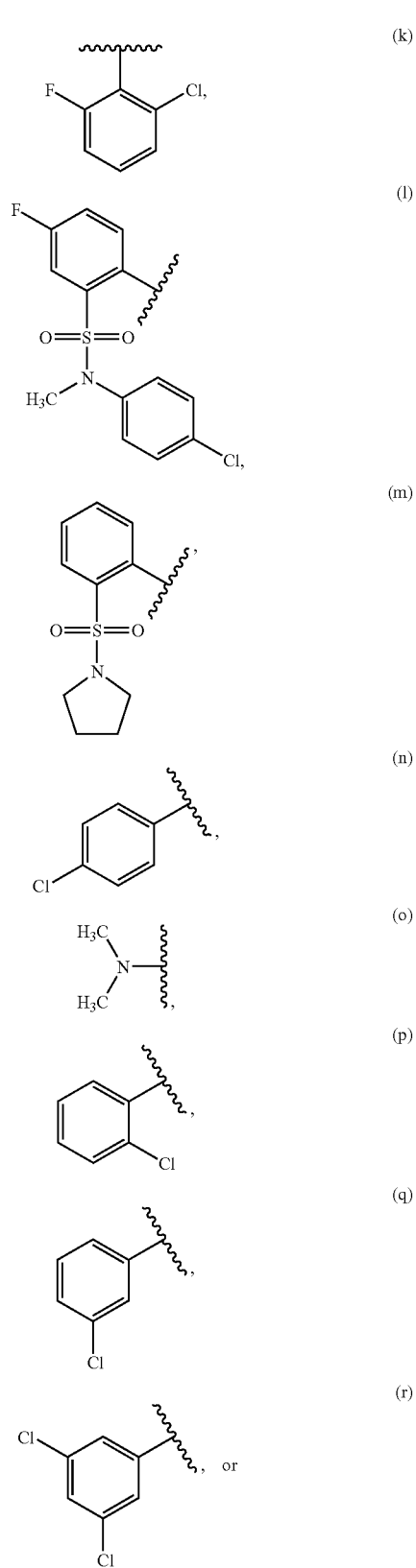

(s)
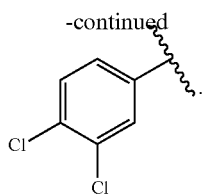

6. The compound of claim 1 wherein X is —CH$_2$— or —SO$_2$—.
7. The compound of claim 1 wherein M$^1$ is nitrogen.
8. The compound of claim 7 wherein n is 2.
9. The compound of claim 1 wherein Y is —C(O)—.
10. The compound of claim 1 wherein Z is an alkyl group.
11. The compound of claim 10 wherein Z is —CH$_2$— or

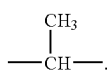

12. The compound of claim 1 wherein R$^2$ is a six membered heteroaryl ring or a substituted six membered heteroaryl ring.
13. The compound of claim 12 wherein R$^2$ is pyridyl or substituted pyridyl.
14. The compound of claim 13 wherein said substituted pyridyl is substituted with —NH$_2$.
15. The compound of claim 13 wherein R$^2$ is selected from:

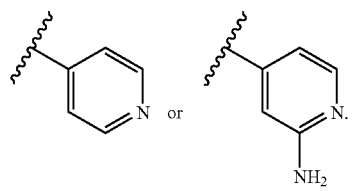

16. The compound of claim 1 wherein a is 0 and b is 0.
17. The compound of claim 1 wherein:
(A) R$^1$ is selected from:
  (1) substituted aryl;
  (2) substituted heteroaryl; or
  (3) formula IVA wherein each R$^3$ is independently selected;
(B) X is —CH$_2$— or —SO$_2$—;
(C) M$^1$ is nitrogen;
(D) n is 2;
(E) Y is —C(O)—;
(F) Z is an alkyl group;
(G) R$^2$ is a six membered heteroaryl ring or a substituted six membered heteroaryl ring;
(H) a is 0; and
(I) b is 0.
18. The compound of claim 17 wherein R$^1$ is selected from:
(1) substituted phenyl;
(2) substituted isoxazolyl; or
(3) —N(CH$_3$)$_2$.
19. The compound of claim 18 wherein R$^2$ is pyridyl or substituted pyridyl.
20. The compound of claim 19 wherein Z is selected from: —CH$_2$— or

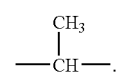

21. The compound of claim 20 wherein R$^1$ is selected from:

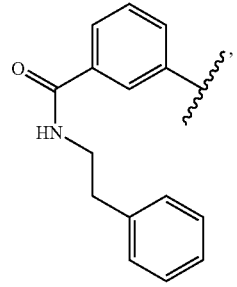
(a)

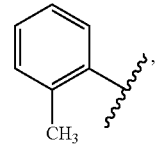
(b)

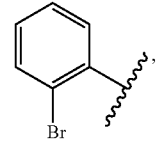
(c)

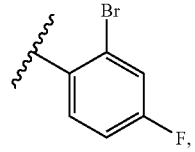
(d)

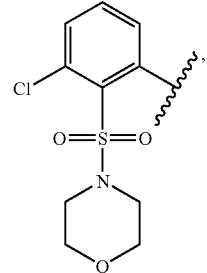
(e)

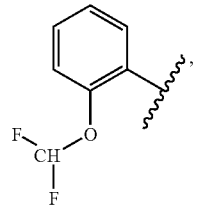
(f)

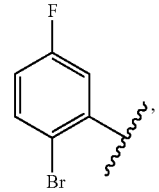
(g)

-continued (h) 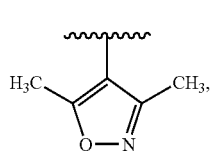

(i) 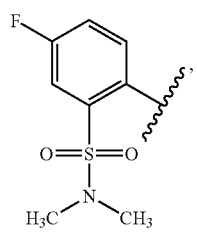

(j) 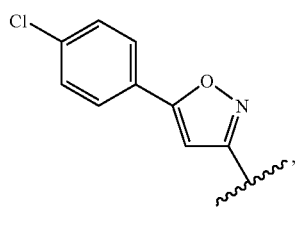

(k) 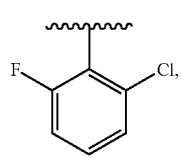

(l) 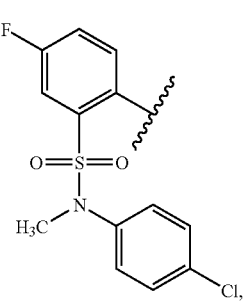

(m) 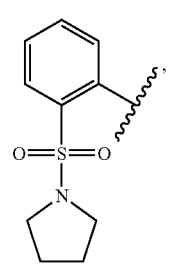

(n) 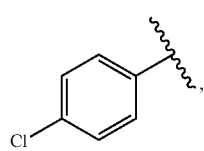

(o) 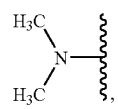

-continued (p) 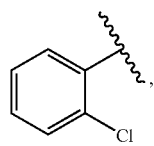

(q) 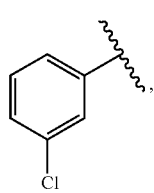

(r) 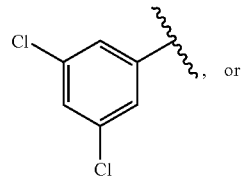, or (s) 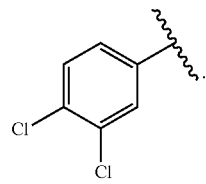.

22. The compound of claim 20 wherein $R^2$ is selected from:

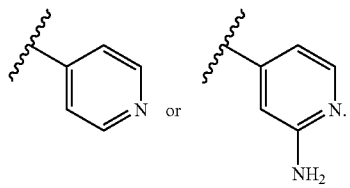

23. The compound of claim 21 wherein $R^2$ is selected from:

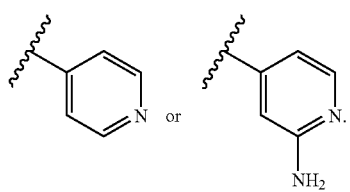

24. A pharmaceutical composition comprising an effective amount of a compound of claim 1 and a pharmaceutically effective carrier.

25. A method of treating obesity comprising administering to a patient in need of such treatment an effective amount of a compound of claim 1.

26. The compound of claim 1 having the structure
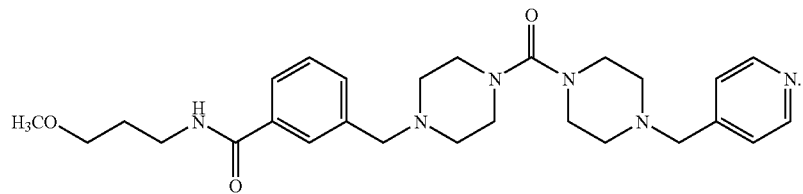
* * * * *

UNITED STATES PATENT AND TRADEMARK OFFICE
CERTIFICATE OF CORRECTION

PATENT NO. : 7,238,688 B2
APPLICATION NO. : 10/974329
DATED : July 3, 2007
INVENTOR(S) : Stuart B Rosenblum Page 1 of 1

It is certified that error appears in the above-identified patent and that said Letters Patent is hereby corrected as shown below:

Column 150
Claim 1, Lines 10-15, replace "$(R^{12})a$" with -- $(R^{13})b$ --

Column 153
Claim 1, Line 26, replace "$R_{20}$" with -- $R^{20}$ --

Signed and Sealed this

Twenty-first Day of October, 2008

JON W. DUDAS
*Director of the United States Patent and Trademark Office*